United States Patent
Moberg et al.

(10) Patent No.: US 8,062,257 B2
(45) Date of Patent: *Nov. 22, 2011

(54) METHOD AND APPARATUS FOR DETECTING OCCLUSIONS IN AN AMBULATORY INFUSION PUMP

(75) Inventors: Sheldon B. Moberg, Thousand Oaks, CA (US); Ian B. Hanson, Northridge, CA (US); Cary D. Talbot, Santa Clarita, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/775,353

(22) Filed: May 6, 2010

(65) Prior Publication Data

US 2010/0217192 A1 Aug. 26, 2010

Related U.S. Application Data

(63) Continuation of application No. 11/602,417, filed on Nov. 20, 2006, now Pat. No. 7,766,873, which is a continuation-in-part of application No. 11/323,104, filed on Dec. 30, 2005, now Pat. No. 7,621,893, which is a continuation-in-part of application No. 10/691,187, filed on Oct. 22, 2003, now Pat. No. 7,193,521, which is a continuation-in-part of application No. 09/698,783, filed on Oct. 27, 2000, now Pat. No. 6,800,071, which is a continuation-in-part of application No. 09/429,352, filed on Oct. 28, 1999, now Pat. No. 6,248,093.

(60) Provisional application No. 60/106,237, filed on Oct. 29, 1998.

(51) Int. Cl.
*A61M 1/00* (2006.01)

(52) U.S. Cl. .................................. 604/151; 700/282
(58) Field of Classification Search ............... 604/65, 604/67, 131, 151–155; 700/282
See application file for complete search history.

(56) References Cited

U.S. PATENT DOCUMENTS 4,433,072 A 2/1984 Pusineri et al.
(Continued)

FOREIGN PATENT DOCUMENTS
EP 0335385 A2 10/1989
(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.

(Continued)

*Primary Examiner* — Nicholas D Lucchesi
*Assistant Examiner* — Gerald Landry, II
(74) *Attorney, Agent, or Firm* — Pillsbury Winthrop Shaw Pittman LLP

(57) ABSTRACT

An improved pump, reservoir and reservoir piston are provided for controlled delivery of fluids. A motor is operably coupled to a drive member, such as a drive screw, which is adapted to advance a plunger slide in response to operation of the motor. The plunger slide is removably coupled to the piston. A method, system, and an article of manufacture for automatically detecting an occlusion in a medication infusion pump is provided. The electrical current to an infusion pump is measured. Based on a series of measurements of one or more variables, the infusion pump detects whether there is an occlusion in the system.

19 Claims, 33 Drawing Sheets

U.S. PATENT DOCUMENTS

| | | | |
|---|---|---|---|
| 4,460,355 A | 7/1984 | Layman | |
| 4,494,950 A | 1/1985 | Fischell | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,726 A | 3/1988 | Allen, III | |
| 4,781,798 A | 11/1988 | Gough | |
| 4,871,351 A | 10/1989 | Feingold | |
| 4,882,575 A | 11/1989 | Kawahara | |
| 5,080,653 A | 1/1992 | Voss et al. | |
| 5,096,385 A * | 3/1992 | Georgi et al. | 417/18 |
| 5,097,122 A | 3/1992 | Colman et al. | |
| 5,101,814 A | 4/1992 | Palti | |
| 5,108,819 A | 4/1992 | Heller et al. | |
| 5,165,407 A | 11/1992 | Wilson et al. | |
| 5,190,522 A | 3/1993 | Wojcicki et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,292,306 A | 3/1994 | Wynkoop et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,356,786 A | 10/1994 | Heller et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,497,772 A | 3/1996 | Schulman et al. | |
| 5,543,326 A | 8/1996 | Heller et al. | |
| 5,569,186 A | 10/1996 | Lord et al. | |
| 5,586,553 A | 12/1996 | Halili et al. | |
| 5,593,852 A | 1/1997 | Heller et al. | |
| 5,660,163 A | 8/1997 | Schulman et al. | |
| 5,665,065 A | 9/1997 | Colman et al. | |
| 5,665,222 A | 9/1997 | Heller et al. | |
| 5,750,926 A | 5/1998 | Schulman et al. | |
| 5,779,665 A | 7/1998 | Mastrototaro et al. | |
| 5,791,344 A | 8/1998 | Schulman et al. | |
| 5,803,712 A | 9/1998 | Davis et al. | |
| 5,904,708 A | 5/1999 | Goedeke | |
| 5,917,346 A | 6/1999 | Gord et al. | |
| 5,965,380 A | 10/1999 | Heller et al. | |
| 5,972,199 A | 10/1999 | Heller et al. | |
| 5,989,222 A | 11/1999 | Cole et al. | |
| 5,999,848 A | 12/1999 | Gord et al. | |
| 5,999,849 A | 12/1999 | Gord et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,146,109 A * | 11/2000 | Davis et al. | 417/244 |
| 6,162,611 A | 12/2000 | Heller et al. | |
| 6,175,752 B1 | 1/2001 | Say et al. | |
| 6,248,093 B1 | 6/2001 | Moberg | |
| 6,259,937 B1 | 7/2001 | Schulman et al. | |
| 6,329,161 B1 | 12/2001 | Heller et al. | |
| 6,472,122 B1 | 10/2002 | Schulman et al. | |
| 6,484,046 B1 | 11/2002 | Say et al. | |
| 6,485,465 B2 | 11/2002 | Moberg et al. | |
| 6,503,381 B1 | 1/2003 | Gotoh et al. | |
| 6,514,718 B2 | 2/2003 | Heller et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,654,625 B1 | 11/2003 | Say et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,733,471 B1 | 5/2004 | Ericson et al. | |
| 6,746,582 B2 | 6/2004 | Heller et al. | |
| 6,749,740 B2 | 6/2004 | Liamos et al. | |
| 6,809,653 B1 | 10/2004 | Mann et al. | |
| 6,881,551 B2 | 4/2005 | Heller et al. | |
| 6,893,545 B2 | 5/2005 | Gotoh et al. | |
| 6,916,159 B2 | 7/2005 | Rush et al. | |
| 6,932,894 B2 | 8/2005 | Mao et al. | |
| 6,942,518 B2 | 9/2005 | Liamos et al. | |
| 7,267,665 B2 | 9/2007 | Steil et al. | |
| 7,402,153 B2 | 7/2008 | Steil et al. | |
| 7,702,574 B2 * | 4/2010 | Lawrence | 705/38 |
| 2001/0025189 A1 | 9/2001 | Haueter et al. | |
| 2002/0082665 A1 | 6/2002 | Haller et al. | |
| 2002/0161288 A1 | 10/2002 | Shin et al. | |
| 2003/0078560 A1 | 4/2003 | Miller et al. | |
| 2003/0088166 A1 | 5/2003 | Say et al. | |
| 2003/0152823 A1 | 8/2003 | Heller | |
| 2003/0168338 A1 | 9/2003 | Gao et al. | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0074785 A1 | 4/2004 | Holker et al. | |
| 2004/0093167 A1 | 5/2004 | Braig et al. | |
| 2004/0111017 A1 | 6/2004 | Say et al. | |
| 2004/0133166 A1 | 7/2004 | Moberg et al. | |
| 2005/0214585 A1 | 9/2005 | Li et al. | |
| 2006/0184154 A1 | 8/2006 | Moberg et al. | |
| 2007/0062251 A1 | 3/2007 | Anex | |
| 2007/0093753 A1 * | 4/2007 | Krulevitch et al. | 604/131 |

FOREIGN PATENT DOCUMENTS

| | | | |
|---|---|---|---|
| EP | 1338295 A1 | 8/2003 | |
| EP | 1529546 A1 | 5/2005 | |
| WO | WO 93/04284 A1 | 3/1993 | |
| WO | WO 96/37246 A1 | 11/1996 | |
| WO | WO 02/058537 A2 | 8/2002 | |
| WO | WO 2005/102417 A2 | 11/2005 | |
| WO | WO 2005/102417 A3 | 11/2005 | |
| WO | WO 2007/035567 A2 | 3/2007 | |

OTHER PUBLICATIONS

Abel et al., "A Method for Evaluating in vivo the Functional Characteristics of Glucose Sensors," Biosensors, 1986, pp. 211-220, vol. 2.

Boguslavsky et al., "Applications of redox polymers in biosensors," Solid State Ionics, 1993, pp. 189-197, vol. 60.

Geise et al., "Electropolymerized 1,3-diaminobenzene for the construction of a 1-1'dimethylferrocene mediated glucose biosensor,"Analytica Chim. Acta.,1993, pp. 467-473, v18.

Gernet et al., "A planar glucose enzyme electrode," Sensors and Actuators, 1989, pp. 537-540, vol. 17, Elsevier Sequoia, Netherlands.

Gernet et al., "Fabrication and Characterization of a Planar Electrochemical Cell and Its Applications as a Glucose Sensor," Sensors and Actuators, 1989, pp. 49-70, vol. 18.

Gorton et al., "Amperometric glucose senosrs based on immobilized glucose-oxidizing enzymes and chemically modified electrodes," Analytica Chim Acta., 1991, pp. 43-54, v. 249.

Gorton et al., "Amperometric biosensors based on an apparent direct electron transfer between electrodes and immobilized peroxidases," Analyst, 1992, pp. 1235-41, vol. 117.

Gough et al., "Two-Dimensional Enzyme Electrode Sensor for Glucose," Analytical Chemistry, 1985, pp. 2351-57, vol. 57.

Gregg et al., "Redox polymer films containing enzymes," J. Phys. Chem., 1991, pp. 5970-5975.

Gregg et al., "Cross-Linked Redox Gels Containing Glucose Oxidase for Amperometric Biosensor Applications," Anal. Chem., 1990, pp. 258-263, vol. 62.

Heller et al., "Electrical Wiring of Redox Enzymes," Accounts of Chemical Research, 1990, pp. 128-134, vol. 23, No. 5.

Johnson et al., "In vivo evaluation of an electroenzymatic glucose sensor implanted in subcutaneous tissue," Biosensors & Bioelectronics, 1992, pp. 709-714, vol. 7.

Jonsson et al., "An Electrochemical Sensor for Hydrogen Peroxide Based on Peroxidase Adsorbed on a Spectrographic Graphite Electrode," Electroanalysts, 1989, pp. 465-468, v. 1.

Kanapieniene et al., "Miniature glucose biosensor with extended linearity," Sensors and Actuators, 1992, pp. 37-40, vol. B, No. 10.

Kawamori et al., "Perfect Normalization of Excessive Glucagon Responses to Intravenous Arginine in Human Diabetes Mellitus With . . . ," Diabetes, 1980, pp. 762-765, vol. 29.

Kimura et al., "An immobilized Enzyme Membrane Fabrication Method using an Ink Jet Nozzle," Biosensors, 1988, pp. 41-52, vol. 4.

Koudelka et al., "In-vivio Behaviour of Hypodermically Implanted Microfabricated Glucose Sensors," Biosensors & Bioelectronics, 1991, pp. 31-36, vol. 6.

Mastrototaro et al., "An electroenzymatic glucose sensor fabricated on a flexible substrate," Sensors and Actuators, 1991, pp. 139-144, vol. 5.

Mastrototaro et al., "An Electroenzymatic Sensor Capable of 72 Hour Continuous Monitoring of Subcutaneous Glucose," 14th Int'l Diabetes Federation Congress, 1991.

McKean et al., "A Telemetry-Instrumentation System for Chronically Implanted Glucose and Oxygen Sensors," IEEE Transactions on Biomedical Eng., 1988, pp. 526-532, vol. 35, No. 7.

Monroe, "Novel implantable glucose sensors," ACL, 1989, pp. 8-16.

Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n. 2.

Nakamato et al., "A Lift-Off Method for Patterning Enzyme-Immobilized Membranes in Multi-Biosensors," Sensors and Actuators, 1988, pp. 165-172, vol. 13.

Nishida et al., "Clinical applications of the wearable artificial endocrine pancreas with the newly designed . . . ," Path. and Treat. Of NIDDM . . . , 1994, p. 353-358, No. 1057.

Shichiri et al., "An artificial endocrine pancrease—problems awaiting solutions for long term clinical applications of . . . ," Frontiers Med. Biol. Eng., 1991, pp. 283-292, v.3.

Shichiri et al., "Wearable Artificial Endocrine Pancreas with Needle-Type Glucose Sensor," The Lancet, 1982, pp. 1129-1131, vol. 2 (8308).

Shichiri et al., "Telemetry Glucose Monitoring Device with Needle-Type Glucose Sensor," Diabetes Care, May-Jun. 1986, pp. 298-301, vol. 9, No. 3.

Shichiri et al., "Normalization of the Paradoxic Secretion of Glucagen in Diabetics Who Were Controlled by the Artificial Beta Cell," Diabetes, 1979, pp. 272-275, vol. 28.

Shichiri et al., "Closed-Loop Glycemic Control with a Wearable Artificial Endocrine Pancreas," Diabetes, 1984, pp. 1200-1202, vol. 33.

Shichiri et al., "In Vivo Characteristics of Needle-Type Glucose Sensor," Hormone and Metabolic Research, 1988, pp. 17-20, vol. 20.

Shichiri et al., "A Needle-Type Glucose Sensor," Life Support Systems: The Journal of the European Society for Artificial Organs, 1984, pp. 7-9, vol. 2, supplement 1.

Shichiri et al., "The Wearable Artificial Endocrine Pancreas with a Needle-Type Glucose Sensor," Acta Pediatr, Jpn, 1984, pp. 358-370, vol. 26.

Shichiri et al., "Glycaemic Control in Pancreatectomized Dogs with a Wearable Artificial Endocrine Pancreas," Diabetologica, 1983, pp. 179-184, vol. 24.

Shichiri et al., "Membrane design for extending the long-life of an implantable glucose sensor," Diab. Nutr. Metab., 1989, pp. 309-313, vol. 2.

Shinkai et al., "Molecular Recognition of Mono- and Di-Saccharides by Phenylboronic Acids in Solvent Extraction and as a Monolayer," J. Chem. Soc., 1991, pp. 1039-1041.

Tamiya et al., "Micro Glucose Sensors Using Electron Mediators Immobilized on a Polypyrrole-Modified Electrode," Sensors and Actuators, 1989, pp. 297-307, v.18.

Tsukagoshi et al., "Specific Complexation with Mono- and Disaccharides That Can Be Detected by Circular Dichroism," J. Org. Chem., 1991, pp. 4089-4091, vol. 56.

Urban et al., "Minaturized multi-enzyme biosensors integrated with pH sensors on flexible polymer carriers . . . ," Biosensors & Bioelectronics, 1992, pp. 733-739, vol. 7.

Urban et al., "Miniaturized thin-film biosensors using covalently immobilized glucose oxidase," Biosensors & Bioelectronics, 1991, pp. 555-562, vol. 6.

Velho et al., "In vivo calibration of a subcutaneous glucose sensor for determination of subcutaneous glucose kinetics," Diab. Nutr. Metab., 1988 pp. 227-233, v.3.

Yokoyama et al., "Integrated Biosensor for Glucose and Galactose," Analytica Chimica Acta., 1989, pp. 137-142, vol. 218.

Nishida et al., "Development of a ferrocene—mediated needle-type glucose sensor . . . ," Medical Process Through Technology, 1995, pp. 91-103, vol. 21.

Koudelka et al., "Planar Amperometric Enzyme-Based Glucose Microelectrode," Sensors and Actuators, 1989, pp. 157-165, vol. 18.

Yamasaki et al., "Direct measurement of whole blood glucose by a needle-type sensor," Clinica Chimica Acta., 1989, pp. 93-98, vol. 93.

Sternberg et al., "Study and Development of Multilayer Needle-type Enzyme-based Glucose Microsensors," Biosensors, 1988, pp. 27-40, vol. 4.

Shaw et al., "In vitro testing of a simply constructed, highly stable glucose sensor suitable for implantation . . . ," Biosensors & Bioelectronics, 1991, pp. 401-406, vol. 6.

Poitout et al., "A glucose monitoring system for on line estimation in man of blood glucose concentration using a miniaturized . . . ," Diabetologia, 1993, pp. 658-663, vol. 36.

Hashigushi et al., "Development of a Miniaturized Glucose Monitoring System by Combining a Needle-Type Glucose Sensor . . . ," Diabetes Care, 1994, pp. 387-389, v.17, n. 5.

Jobst et al., "Thin-Film Microbiosensors for Glucose-Lactate Monitoring," Anal. Chem., 1996, p. 3173-3179, vol. 68.

Shults et al., "A Telemetry-Instrumentation System for Monitoring Multiple Subcutaneously Implanted Glucose Sensors," IEEE Trans. On Biomed. Eng., 1994, pp. 937-942, v41, n. 10.

Wang et al., "Needle-Type Dual Microsensor for the Simultaneous Monitoring of Glucose and Insulin," Anal. Chem., 2001, pp. 844-847, vol. 73.

Moussey et al., "Performance of Subcutaneously Implanted Needle-Type Glucose Sensors Employing a Novel Trilayer Coating," Anal. Chem., 1993, 2072-77, vol. 65.

Bindra et al., "Design and in Vitro Studies of a Needle-Type Glucose Sensor for Subcutaneous Monitoring," Anal. Chem., 1991, pp. 1692-96, vol. 63.

PCT International Search Report, (PCT/US2007/023569) Jul. 8, 2008, (6-pgs).

International Preliminary Report on Patentability, (PCT/US2007/023569) May 26, 2009, (8-pgs).

PCT International Search Report, (PCT/US2006/048951) Sep. 24, 2007, (7-pgs).

* cited by examiner

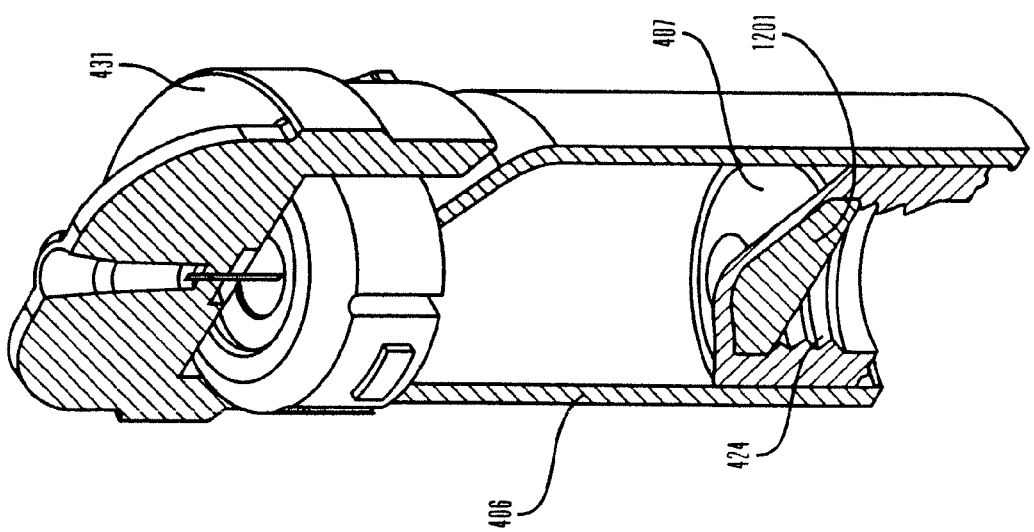

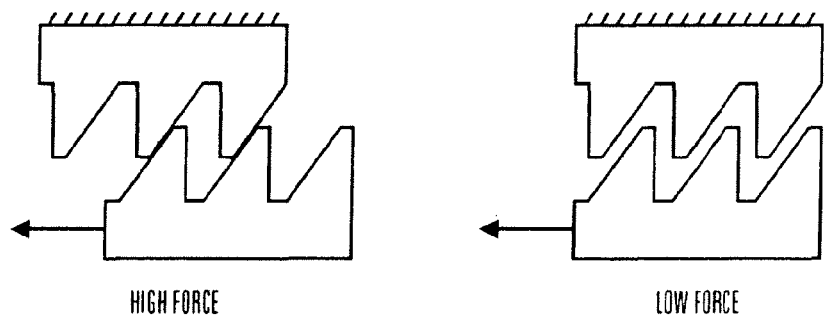
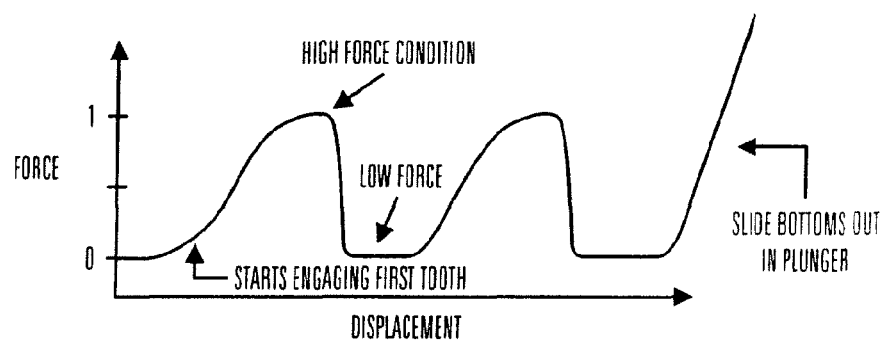
FIG. 13a
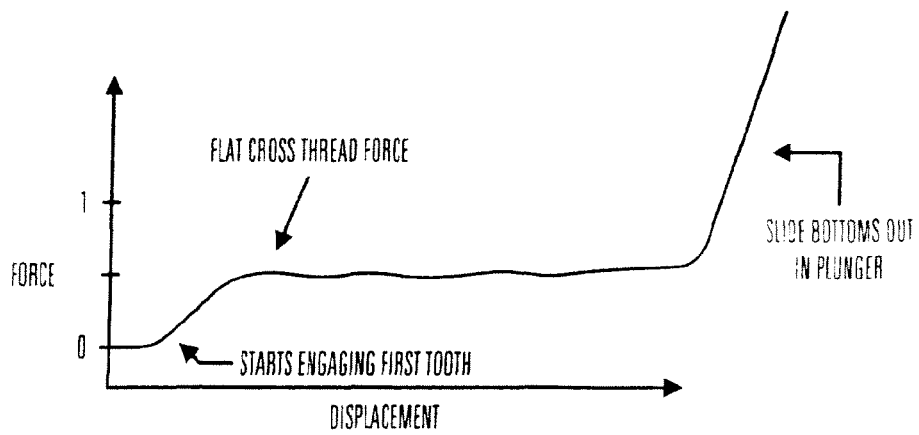
FIG. 13b

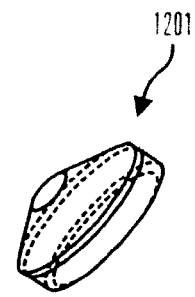
FIG. 16a
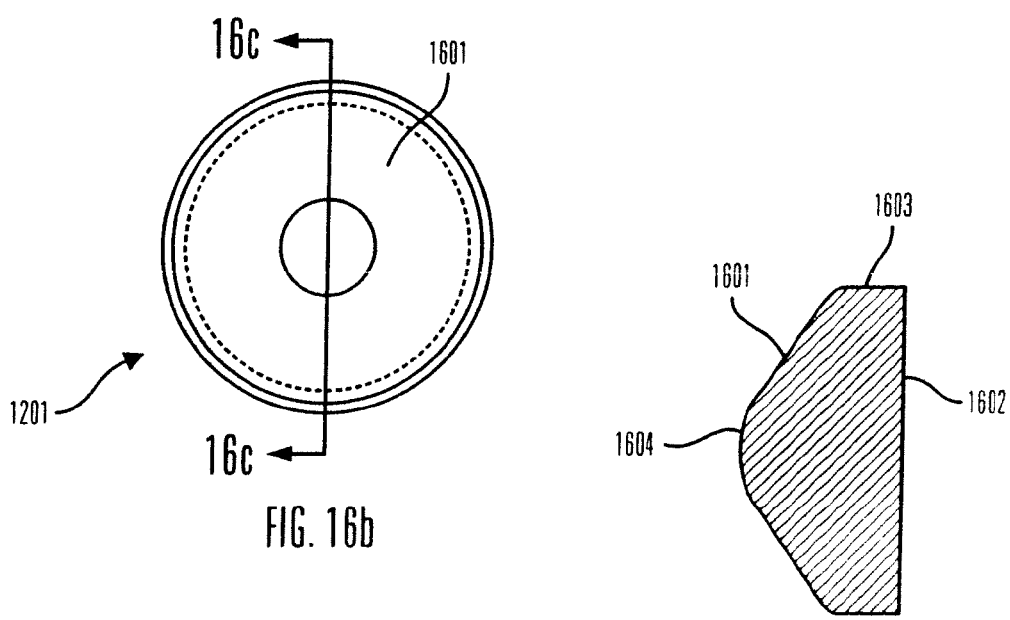
FIG. 16b
FIG. 16c

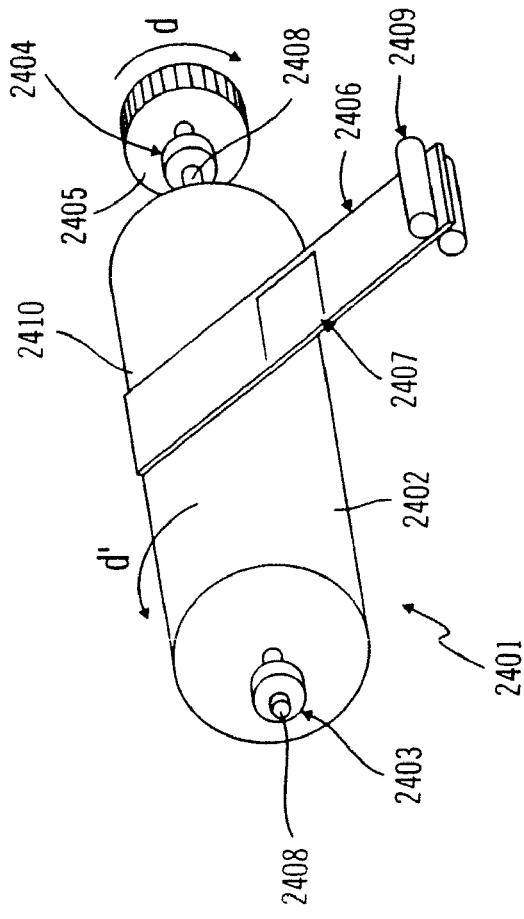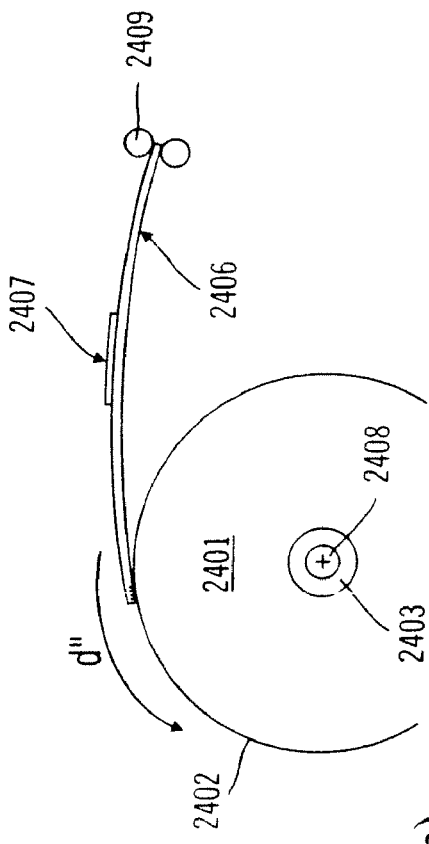
FIG. 23(a)
FIG. 23(b)

METHOD AND APPARATUS FOR DETECTING OCCLUSIONS IN AN AMBULATORY INFUSION PUMP

RELATED APPLICATION DATA

This is a continuation application of U.S. patent application Ser. No. 11/602,417, filed Nov. 20, 2006, now U.S. Pat. No. 7,766,873, which is a continuation-in-part application claiming priority from U.S. patent application Ser. No. 11/323,104, filed Dec. 30, 2005, now U.S. Pat. No. 7,621,893, which is a continuation-in-part application claiming priority from U.S. patent application Ser. No. 10/691,187, filed Oct. 22, 2003, now U.S. Pat. No. 7,193,521, which is a continuation-in-part application claiming priority from U.S. patent application Ser. No. 09/698,783, filed Oct. 27, 2000, now U.S. Pat. No. 6,800,071, which is a continuation-in-part application claiming priority from U.S. patent application Ser. No. 09/429,352, filed Oct. 28, 1999, now U.S. Pat. No. 6,248,093, which claims priority from provisional patent application Ser. No. 60/106,237, filed Oct. 29, 1998, all of which are incorporated herein by reference.

BACKGROUND OF THE INVENTION

1. Field of the Invention

This invention relates generally to improvements in infusion pumps such as those used for controlled delivery of medication to a patient. More specifically, this invention relates to improved methods and apparatuses for detecting errors in detecting fluid pressure and occlusions in fluid delivery paths of infusion pump systems.

2. Description of Related Art

Infusion pump devices and systems are relatively well-known in the medical arts, for use in delivering or dispensing a prescribed medication such as insulin to a patient. In one form, such devices comprise a relatively compact pump housing adapted to receive a syringe or reservoir carrying a prescribed medication for administration to the patient through infusion tubing and an associated catheter or infusion set.

The infusion pump includes a small drive motor connected via a lead screw assembly for motor-driven advancement of a reservoir piston to administer the medication to the user. Programmable controls can operate the drive motor continuously or at periodic intervals to obtain a closely controlled and accurate delivery of the medication over an extended period of time. Such infusion pumps are used to administer insulin and other medications, with exemplary pump constructions being shown and described in U.S. Pat. Nos. 4,562,751; 4,678,408; 4,685,903; 5,080,653 and 5,097,122, which are incorporated by reference herein.

Infusion pumps of the general type described above have provided significant advantages and benefits with respect to accurate delivery of medication or other fluids over an extended period of time. The infusion pump can be designed to be extremely compact as well as water resistant, and may thus be adapted to be carried by the user, for example, by means of a belt clip or the like. As a result, important medication can be delivered to the user with precision and in an automated manner, without significant restriction on the user's mobility or life-style, including in some cases the ability to participate in water sports.

These pumps often incorporate drive systems which uses a lead screw coupled to motors. The motors can be of the DC, stepper or solenoid varieties. These drive systems provide an axial displacement of the syringe or reservoir piston thereby dispensing the medication to the user. Powered drive systems are advantageous since they can be electronically controlled to deliver a predetermined amount of medication by means well known in the art.

In the operation of these pump systems, the reservoir piston will be fully advanced when virtually all of the fluid in the reservoir has been dispensed. Correspondingly, the axial displacement of the motor lead screw is also typically fully displaced. In order to insert a new reservoir, which is full of fluid, it is necessary to restore the lead screw to its original position. Thus the lead screw will have to be rewound or reset.

DC motors and stepper motors are advantageous over solenoid motors in that the former are typically easier to operate at speeds that allow rewinding the drive system electronically. Solenoid based drive systems, on the other hand, often must be reset manually, which in turn makes water resistant construction of the pump housing more difficult.

Lead screw drive systems commonly use several gears which are external to the motor. FIG. 1 shows such a lead screw arrangement which is known in the art. A motor 101 drives a lead screw 102 which has threads which are engaged with a drive nut 103. Thus the rotational force of the lead screw 102 is transferred to the drive nut 103 which causes it to move in an axial direction d. Because the drive nut 103 is fixably attached to a reservoir piston 104 by a latch arm 110, it likewise will be forced in an axial direction d', parallel to direction d, thus dispensing the fluid from a reservoir 105 into an infusion set 106. The lead screw 102 is mounted on a bearing which provides lateral support. The lead screw 102 extends through the bearing and comes in contact with the occlusion detector. One known detector uses an "on/off" pressure limit switch.

Should an occlusion arise in the infusion set 106 tubing, a back pressure will build up in the reservoir 105 as the piston 104 attempts to advance. The force of the piston 104 pushing against the increased back pressure will result in an axial force of the lead screw 102 driving against the detector. If the detector is a pressure limit switch, then an axial force that exceeds the set point of the pressure limit switch will cause the switch to close thus providing an electrical signal through electrical leads and to the system's electronics. This, in turn, can provide a system alarm. The entire assembly can be contained in a water resistant housing 107.

FIG. 2 shows a different drive system and lead screw arrangement which also is known in the art. In this arrangement, a motor 201 (or a motor with an attached gear box) has a drive shaft 201a which drives a set of gears 202. The torque is then transferred from the gears 202 to a lead screw 203. The threads of the lead screw 203 are engaged with threads [not shown] in a plunger slide 204. Thus the torque of the lead screw 203 is transferred to the slide 204 which causes it to move in an axial direction d', parallel to the drive shaft 201a of the motor 201. The slide 204 is in contact with a reservoir piston 205 which likewise will be forced to travel in the axial direction d' thus dispensing fluid from a reservoir 206 into an infusion set 207. The lead screw 203 is mounted on a bearing 209 which provides lateral support. The lead screw 203 can extend through the bearing to come in contact with an occlusion detector. As before, if the detector is a pressure limit switch, then an axial force that exceeds the set point of the pressure limit switch will cause the switch to close thus providing an electrical signal through electrical leads and to the system's electronics. This, in turn, can provide a system alarm. The assembly can be contained in a water resistant housing 208.

As previously noted, these lead screw drive systems use gears which are external to the motor. The gears are in combination with a lead screw with external threads which are used to drive the reservoir's piston. This external arrangement occupies a substantial volume which can increase the overall size of the pump. Moreover, as the number of drive components, such as gears and lead screw, increases, the torque required to overcome inherent mechanical inefficiencies can also increase. As a result, a motor having sufficient torque also often has a consequent demand for increased electrical power.

Yet another known drive is depicted in FIGS. 3a and 3b. A reservoir 301 fits into the unit's housing 302. Also shown are the piston member 303 which is comprised of an elongated member with a substantially circular piston head 304 for displacing the fluid in the reservoir 301 when driven by the rotating drive screw 305 on the shaft (not visible) of the drive motor 306.

As is more clearly shown in FIG. 3b, the reservoir 301, piston head 304 and piston member 303 comprise an integrated unit which is placed into the housing 302 (FIG. 3a). The circular piston head 304 displaces fluid in the reservoir upon axial motion of the piston member 303. The rearward portion of the piston member 303 is shaped like a longitudinal segment of a cylinder as shown in FIG. 3b and is internally threaded so that it may be inserted into a position of engagement with the drive screw 305. The drive screw 305 is a threaded screw gear of a diameter to mesh with the internal threads of the piston member 303. Thus the motor 306 rotates the drive screw 305 which engages the threads of the piston member 303 to displace the piston head 304 in an axial direction d.

While the in-line drive system of FIG. 3a achieves a more compact physical pump size, there are problems associated with the design. The reservoir, piston head and threaded piston member constitute an integrated unit. Thus when the medication is depleted, the unit must be replaced. This results in a relatively expensive disposable item due to the number of components which go into its construction.

Moreover the drive screw 305 and piston head 304 of FIG. 3a are not water resistant. Because the reservoir, piston head and threaded piston member are removable, the drive screw 305 is exposed to the atmosphere. Any water which might come in contact with the drive screw 305 may result in corrosion or contamination which would affect performance or result in drive failure.

The design of FIG. 3a further gives rise to problems associated with position detection of the piston head 304. The piston member 303 can be decoupled from the drive screw 305. However, when another reservoir assembly is inserted, it is not known by the system whether the piston head 304 is in the fully retracted position or in some intermediate position. Complications therefore are presented with respect to providing an ability to electronically detect the position of the piston head 304 in order to determine the extent to which the medication in reservoir 301 has been depleted.

The construction of pumps to be water resistant can give rise to operational problems. As the user travels from various elevations, such as might occur when traveling in an air plane, or as the user engages in other activities which expose the pump to changing atmospheric pressures, differential pressures can arise between the interior of the air tight/water-resistant pump housing and the atmosphere. Should the pressure in the housing exceed external atmospheric pressure, the resulting forces could cause the reservoir piston to be driven inward thus delivering unwanted medication.

Thus it is desirable to have an improved, compact, water resistant drive system which permits safe user activity among various atmospheric pressures and other operating conditions. Moreover it is desirable to have improved medication reservoir pistons for use with such drive systems.

SUMMARY OF THE PREFERRED EMBODIMENTS

An improved apparatus for dispensing a medication fluid is provided. This comprises a reservoir adapted to contain the fluid and a movable piston adapted to vary the size of the reservoir and to discharge the liquid from the reservoir through an outlet. In a certain aspect of the present inventions, the reservoir and piston are adapted for use with a pump drive system having a linear actuation member wherein the piston can be releasably coupled to the linear actuation member.

The piston comprises a first member adapted to be slidably mounted within the reservoir and to form at least part of a fluid-tight barrier therein. The first member has an external proximate side and an external distal side. The external proximate side is adapted to contact the fluid and is made of a material having a first stiffness. A second member has a first side and a second side. At least a portion of the second member is disposed within the first member. The first side of the second member is adjacent to the external proximate side of the first member and is made of a material having a stiffness which is greater than the first stiffness.

In alternative embodiments, the second member first side is in a generally parallel, spaced-apart relationship with the first member external proximate side.

In yet further embodiments, the first member external proximate side is made of an elastomeric material and the second member first side is made of stainless steel or plastic.

In yet further embodiments, the second member is substantially contained within the first member.

In yet further embodiments, the second member extends past the external proximate side of the first member and is adapted for contact with the fluid to complete the fluid-tight barrier within the reservoir.

In yet further embodiments, a method of coupling an actuator to a reservoir piston is provided. Electrical power is provided to a pump motor which is operably coupled to a plunger slide. The power is provided when the plunger slide is in a position other than fully inserted in a reservoir piston cavity. A first value corresponding to the axial force on the plunger slide is measured. A determination is made whether the first value exceeds a second value corresponding to the axial force on the plunger slide when the plunger slide is fully inserted in the piston cavity. Electrical power to the pump motor is terminated after determining that the first value exceeds the second value.

In yet further embodiments of the present invention, a method, system and article of manufacture to detect a malfunction with a force sensor in the infusion pump is described. In preferred embodiments, current measurements to the motor are taken. Based on the current measurements, the infusion pump detects when the plunger slide is seated in the reservoir, and detects a problem with the force sensor when the force sensor independently fails to register a value indicating that the plunger slide is seated in the reservoir. In particular embodiments, the infusion pump detects when the plunger slide is seated in the reservoir by calculating an average current based on the current measurements, comparing the average current to a threshold current; and detecting when the plunger slide is seated in the reservoir when the average current exceeds the threshold current.

In further embodiments, an encoder measures movement of the plunger slide as encoder counts and the infusion pump signals an error with the force sensor when the force sensor independently fails to recognize that the plunger slide is seated in the reservoir after a preset encoder count threshold is exceeded. In yet further embodiments, the time since the plunger slide was seated in the reservoir as indicated by the current measurements is also measured and an error with the force sensor is signaled when the force sensor independently fails to recognize that the plunger slide is seated in the reservoir after a preset time threshold is exceeded.

In further embodiments, occlusions are detected using at least two values of the pump system. For example, these variables can include pressure, delivery volume, force, drive current, drive voltage, motor drive time, motor coast time, delivery pulse energy, motor drive count, motor coast count, and delta encoder count. In yet further embodiments, algorithms to detect occlusions based on one or more values are dynamic, and the values are calculated periodically, and may be calculated continuously, throughout delivery of each pulse.

In further embodiments, occlusions are detected using a series of two or more measurements of a particular value, for example, force. The series of measurements are filtered and/or weighed. In particular embodiments, the series of measurements may be filtered by removing the highest and lowest values. In further embodiments, the weighing of the series of measurements may weight more heavily the most recent readings. If the weighted average is greater than a threshold value, the system determines that an occlusion exists and notifies the user, for example by alarm. The threshold value may be varied based on the drive count.

BRIEF DESCRIPTION OF THE DRAWINGS

FIG. 3b shows the details of a disposable reservoir with the piston and drive member withdrawn of the lead-screw drive mechanism of FIG. 3a.

FIG. 12 is a partial, cross sectional view of a reservoir and a reservoir connector.

FIGS. 13a and 13b are plunger slide force profile diagrams.

FIG. 15b is an elevation view of the reservoir piston of FIG. 15a.

FIG. 16a is a perspective view of a piston insert.

FIG. 16b is a top plan view of the piston insert of FIG. 16a.

FIG. 16c is a cross-sectional view of the insert along lines 16c-16c of FIG. 16b.

FIG. 23(a) is a perspective view of a sensor in a portion of a drive system according to another embodiment of the present invention.

FIG. 23(b) is a rear view of the sensor and pump drive system of FIG. 23(a).

DETAILED DESCRIPTION OF THE PREFERRED EMBODIMENTS

Figure 1:
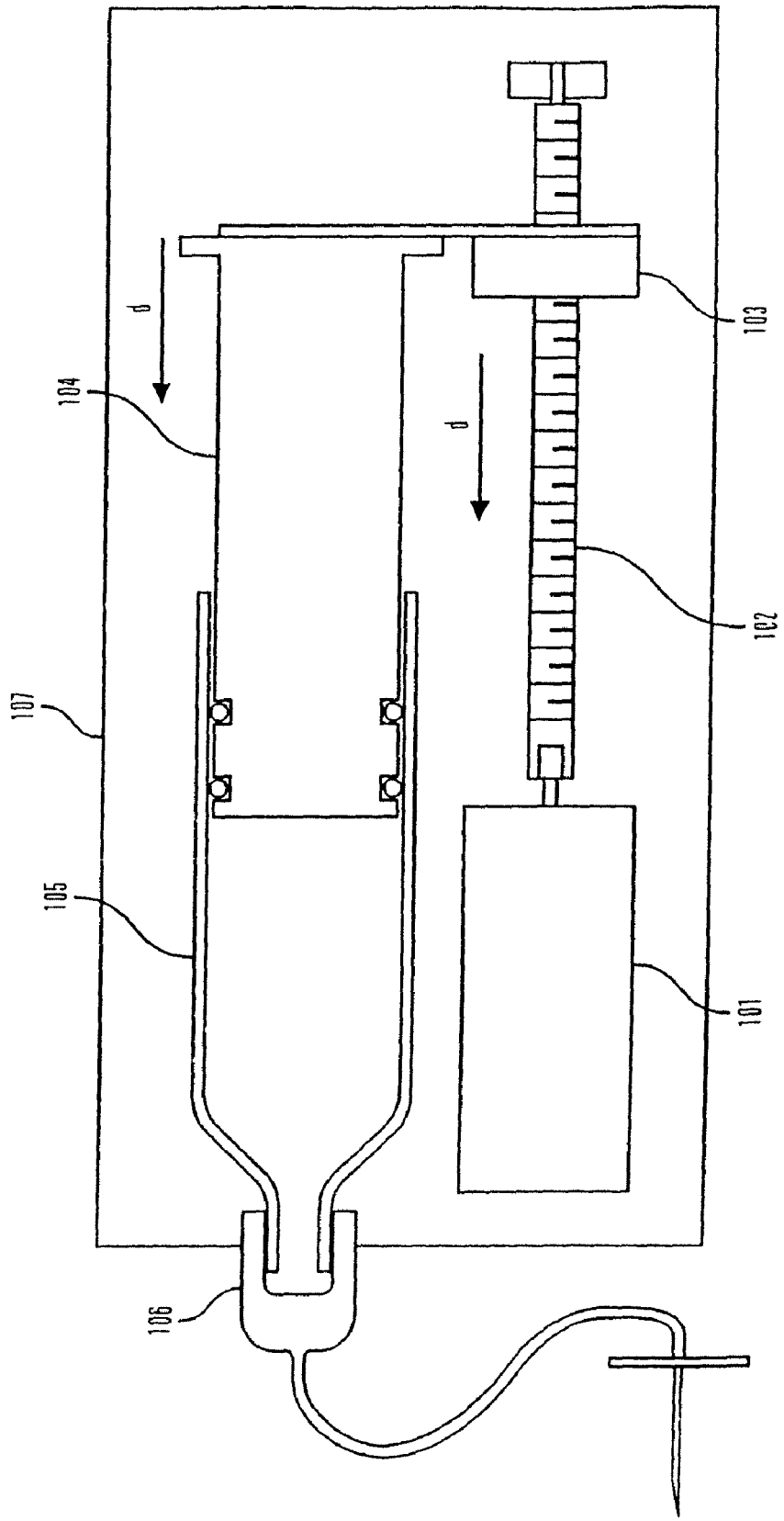
FIG. 1 is a side plan view of a conventional lead-screw drive mechanism.

In the following description, reference is made to the accompanying drawings which form a part hereof and which illustrate several embodiments of the present inventions. It is understood that other embodiments may be utilized and structural and operational changes may be made without departing from the scope of the present inventions.

As shown in the drawings for purposes of illustration, some aspects of the present inventions are directed to a drive mechanism for an infusion pump for medication or other fluids. In preferred embodiments, a releasable coupler couples an in-line drive to a plunger or piston of a reservoir to dispense fluids, such as medications, drugs, vitamins, vaccines, hormones, water or the like. However, it will be recognized that further embodiments of the invention may be used in other devices that require compact and accurate drive mechanisms. Details of the inventions are further provided in co-pending U.S. patent application Ser. No. 09/429,352, filed Oct. 29, 1999, now issued U.S. Pat. No. 6,248,093 and U.S. provisional patent application Ser. No. 60/106,237, filed Oct. 29, 1998, both of which are incorporated herein by reference in their entireties.

In addition, the reservoir piston includes features which provide greater stiffness against fluid back pressure thus reducing system compliance. The piston further includes a threaded attachment feature which permits a releasable yet secure coupling between the reservoir piston and the in-line drive.

Figure 4:
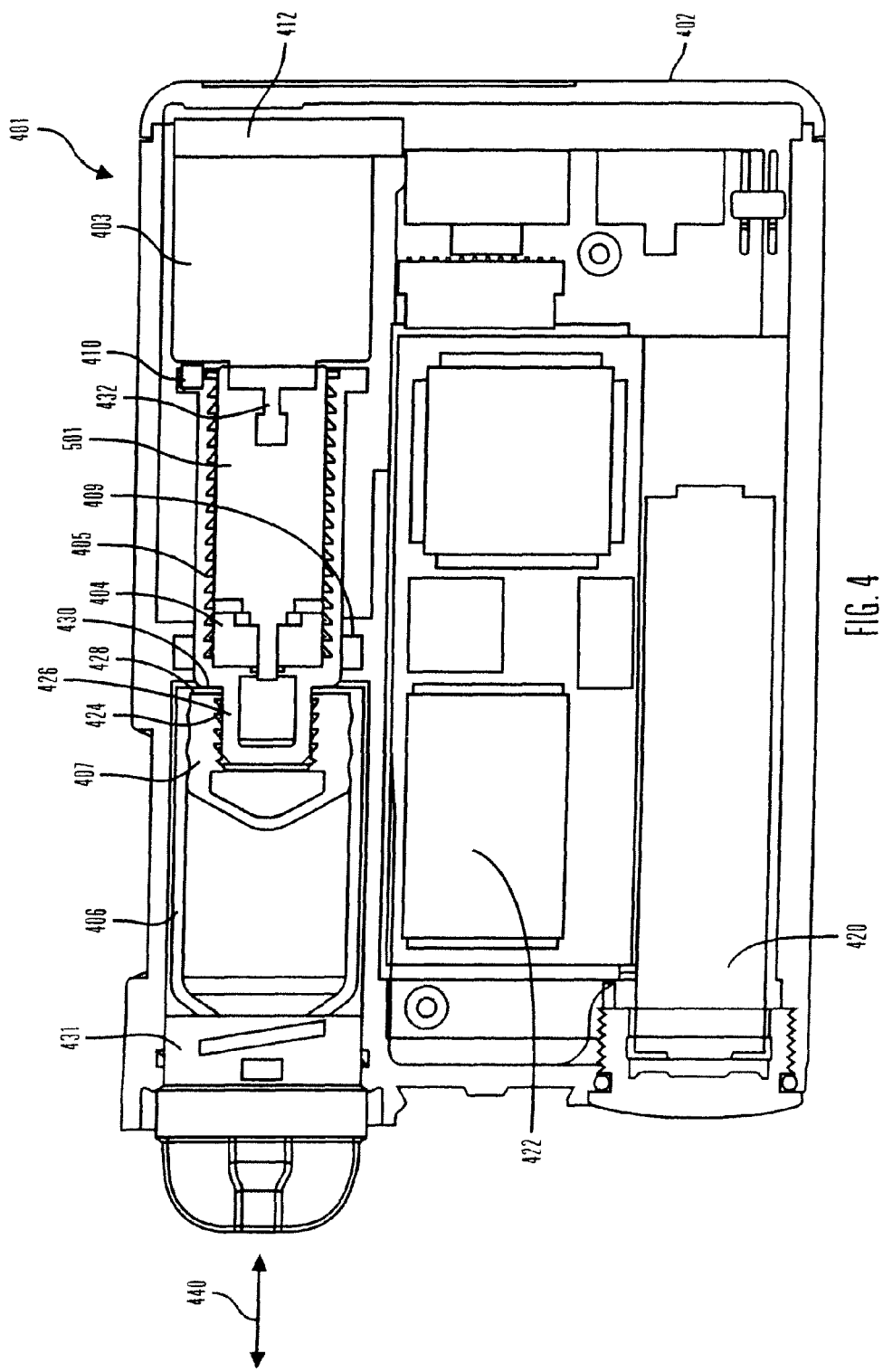
FIG. 4 is a side plan, cut-away view of a drive mechanism in a retracted position in accordance with an embodiment of the present invention.

FIG. 4 shows a side plan, cut-away view of an infusion pump drive mechanism according to one embodiment of the inventions, in which a housing 401, containing a lower section 402 for a power supply 420 and electronic control circuitry 422, accommodates a driving device, such as a motor 403 (e.g., a solenoid, stepper or d.c. motor), a first drive member, such as an externally threaded drive gear or screw 404, a second drive member, such as an internally threaded plunger gear or slide 405, and a removable vial or reservoir 406. The reservoir 406 includes a plunger or piston assembly 407 with O-rings or integral raised ridges for forming a water and air tight seal. The reservoir 406 is secured into the housing 401 with a connector 431 which also serves as the interface between the reservoir 406 and the infusion set tubing (not shown). In one embodiment, the reservoir piston assembly 407 is coupled to a linear actuation member, such as the plunger slide 405, by a releasable coupler. In the illustrated embodiment, the coupler includes a female portion 424 which receives a male portion 426 carried by the plunger slide 405. The female portion 424 is positioned at the end face 428 of the piston assembly 407 and includes a threaded cavity which engages the threads of a male screw extending from the end 430 of the plunger slide 405.

While certain embodiments of the present inventions are directed to disposable, pre-filled reservoirs, alternative embodiments may use refillable cartridges, syringes or the like. The cartridge can be pre-filled with insulin (or other drug or fluid) and inserted into the pump. Alternatively, the cartridge could be filled by the user using an adapter handle on the syringe-piston. After being filled, the handle is removed (such as by unscrewing the handle) so that the cartridge can be placed into the pump.

Referring again to FIG. 4, as the drive shaft 432 of the motor 403 rotates in the gear box 501, the drive screw 404 drives the plunger slide 405 directly to obtain the axial displacement against the reservoir piston assembly 407 to deliver the predetermined amount of medication or liquid. When using a DC or stepper motor, the motor can be rapidly rewound when the reservoir is emptied or as programmed by the user. A sealing device, such as an O-ring seal 409 is in contact with the plunger slide 405 thus allowing it to move axially while maintaining a water resistant barrier between the cavity holding the reservoir 406 and the motor 403. This prevents fluids and other contaminants from entering the drive system.

An anti-rotation key 410 is affixed to the plunger slide 405 and is sized to fit within a groove (not shown) axially disposed in the housing 401. This arrangement serves to prevent motor and plunger slide rotation which might otherwise result from the torque generated by the motor 403 in the event that the friction of the O-ring seal 409 is not sufficient alone to prevent rotation.

The motor 403 is a conventional motor, such as a DC or stepper motor, and is journal mounted in the housing 401 by a system compliance mounting 412. A system compliance mount can be useful in aiding motor startup. Certain types of motors, such as stepper motors, may require a great deal of torque to initiate rotor motion when the rotor's initial at-rest position is in certain orientations with respect to the motor's housing. A motor which is rigidly mounted may not have enough power to develop the necessary starting torque. Including system compliance mounting permits the motor housing to turn slightly in response to high motor torque. This alters the orientation between the rotor and the housing such that less torque is required to initiate rotor motion. A compliance mount can include a rubberized mounting bracket. Alternatively, the mounting could be accomplished using a shaft bearing and leaf spring or other known compliance mountings.

Figure 5:
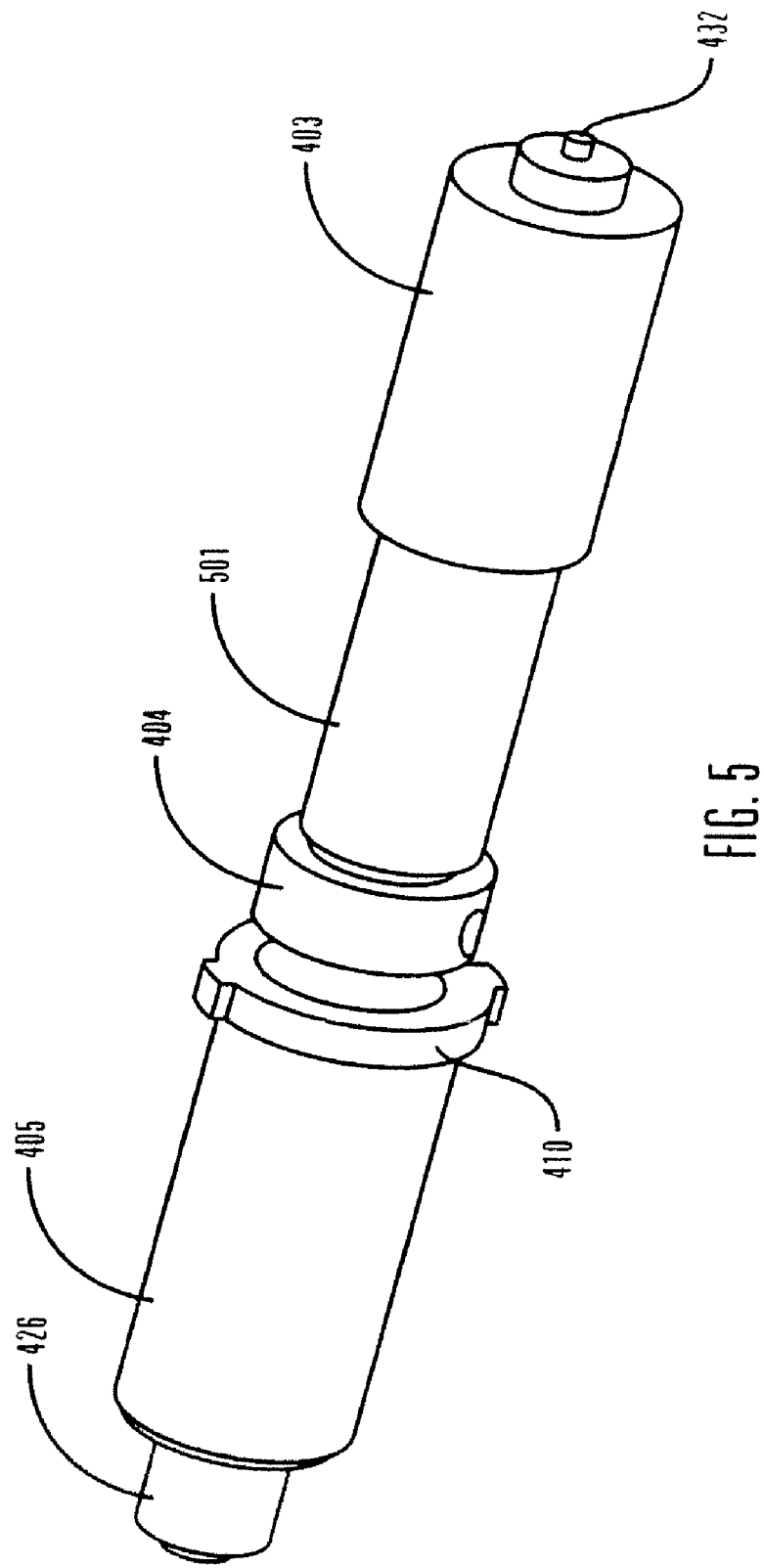
FIG. 5 is a perspective view of the in-line drive mechanism of FIG. 4 outside of the housing.

FIG. 5 shows a perspective view of the in-line drive mechanism of FIG. 4 outside of the housing. The plunger slide 405 (internal threads not shown) is cylindrically shaped and has the screw-shaped male portion 426 of the coupler attached to one end thereof. The anti-rotation key 410 is affixed to the opposite end of the slide 405. The drive screw 404 is of such a diameter as to fit within and engage the internal threads of the plunger slide 405 as shown in FIG. 4. A conventional gear box 501 couples the drive screw 404 to the drive shaft 432 of the motor 403.

Figure 6:
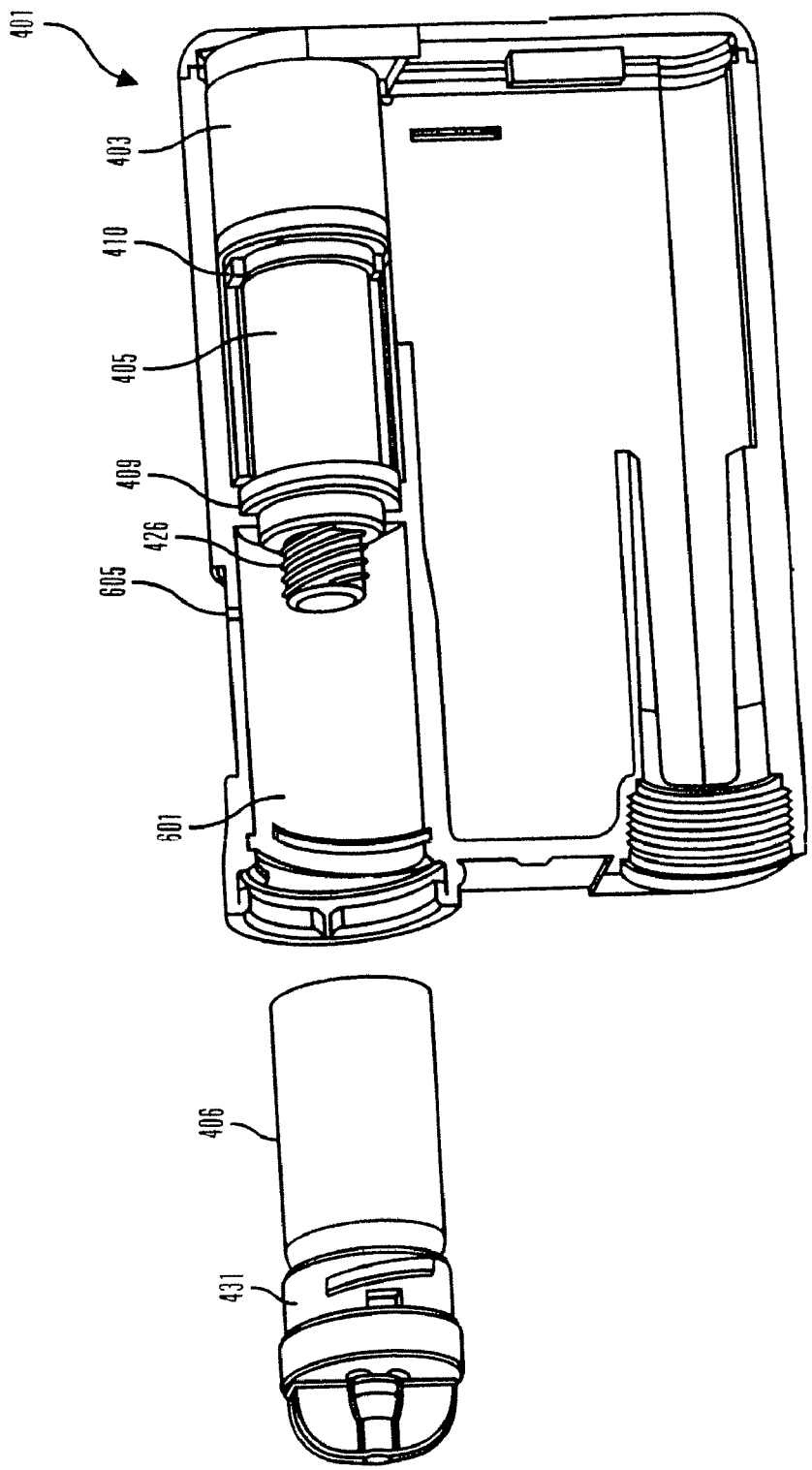
FIG. 6 is a cut-away perspective view of the drive mechanism of FIG. 4 in a retracted position.

FIGS. 4 and 6 show the infusion pump assembly with the plunger slide 405 in the retracted position. The reservoir 406 which may be full of medication or other fluid is inserted in a reservoir cavity 601 which is sized to receive a reservoir or vial. In the retracted position, the plunger slide 405 encloses the gear box 501 (not visible in FIG. 6) while the drive screw 404 (not visible in FIG. 6) remains enclosed within the plunger slide 405 but is situated close to the coupler.

The motor 403 may optionally include an encoder (not shown) which in conjunction with the system electronics can monitor the number of motor rotations. This in turn can be used to accurately determine the position of the plunger slide 405 thus providing information relating to the amount of fluid dispensed from the reservoir 406.

Figure 7A:
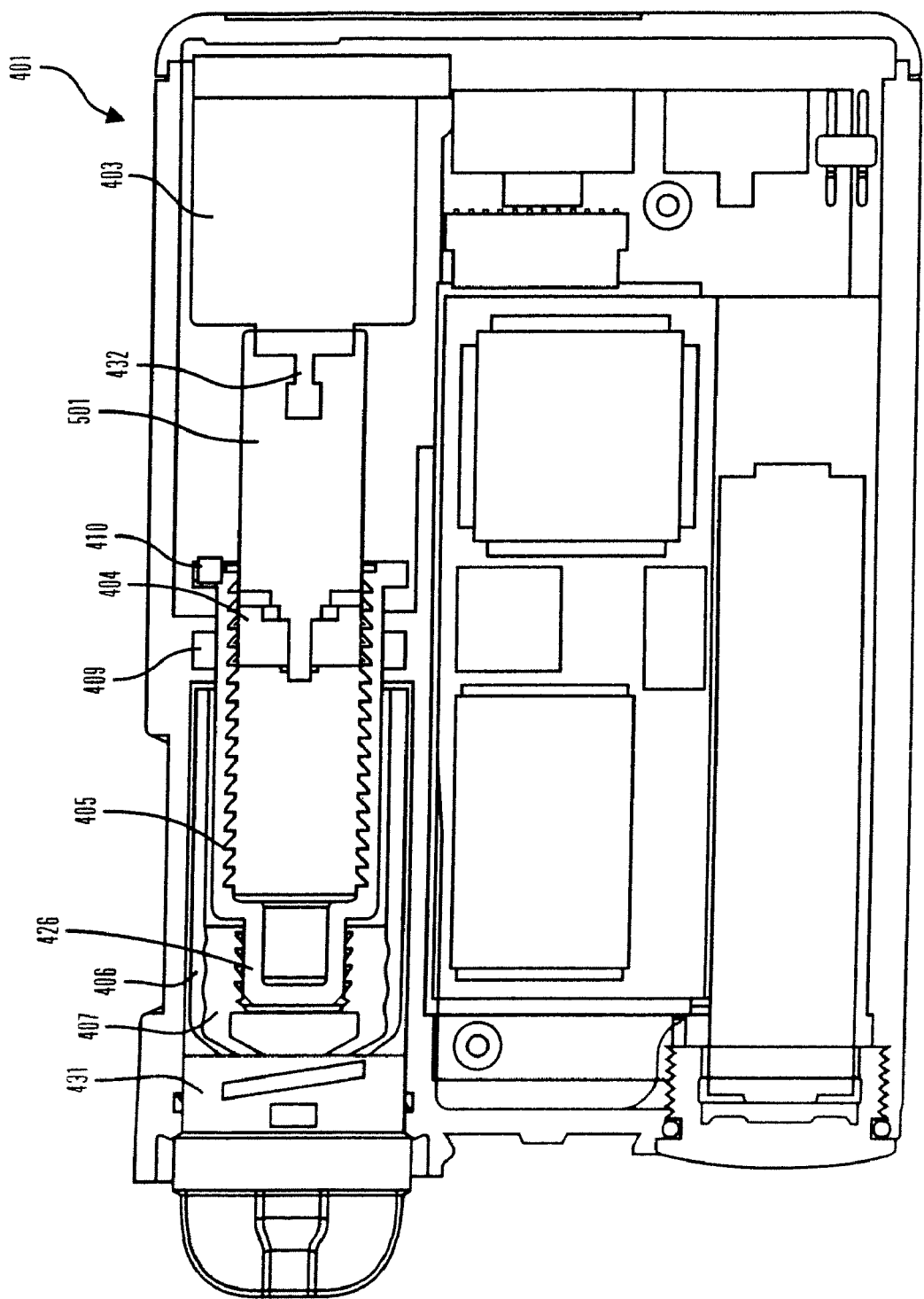
FIG. 7a is a side plan, cut-away view of the drive mechanism of FIG. 4 in an extended position.
Figure 7B:
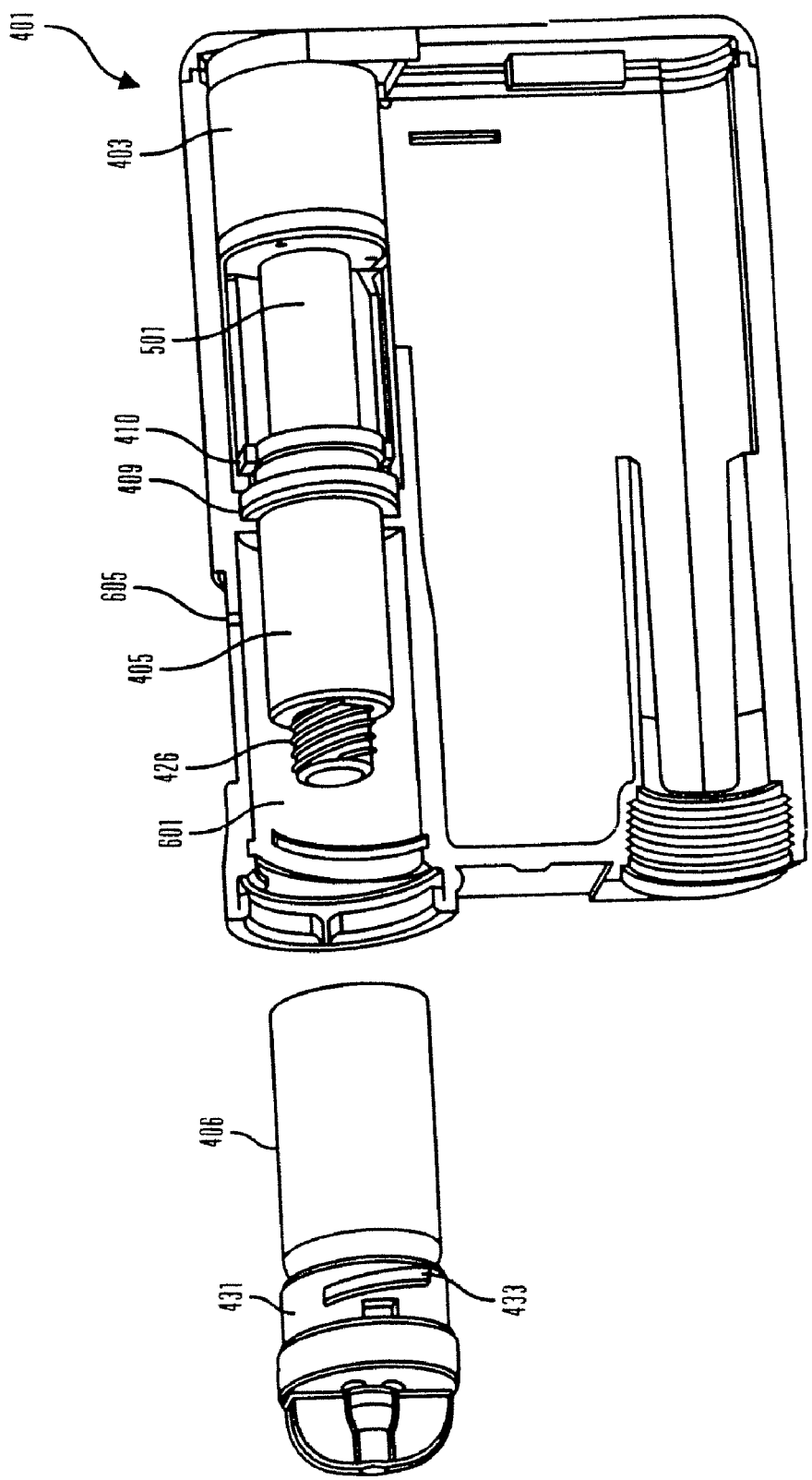
FIG. 7b is a cut-away perspective view of the drive mechanism of FIG. 4 in an extended position.

FIGS. 7a and 7b show the infusion pump assembly with the plunger slide 405 in the fully extended position. In this position, the plunger slide 405 has withdrawn from over the gear box 501 and advanced into the reservoir 406 behind the reservoir piston assembly 407. Accordingly, the plunger slide 405 is sized to fit within the housing of the reservoir 406, such that when the reservoir piston assembly 407 and the plunger slide 405 are in the fully extended position as shown, the reservoir piston assembly 407 has forced most, if not all, of the liquid out of the reservoir 406. As explained in greater detail below, once the reservoir piston assembly 407 has reached the end of its travel path indicating that the reservoir has been depleted, the reservoir 406 may be removed by twisting such that the threaded reservoir piston assembly 407 (not shown in FIG. 7b) disengages from the male portion 426 of the coupler.

In one embodiment, the motor drive shaft 432, gear box 501, drive screw 404, and plunger slide 405 are all coaxially centered within the axis of travel 440 (FIG. 4) of the reservoir piston assembly 407. In certain of the alternative embodiments, one or more of these components may be offset from the center of the axis of travel 440 and yet remain aligned with the axis of travel which has a length which extends the length of the reservoir 406.

Figure 8:
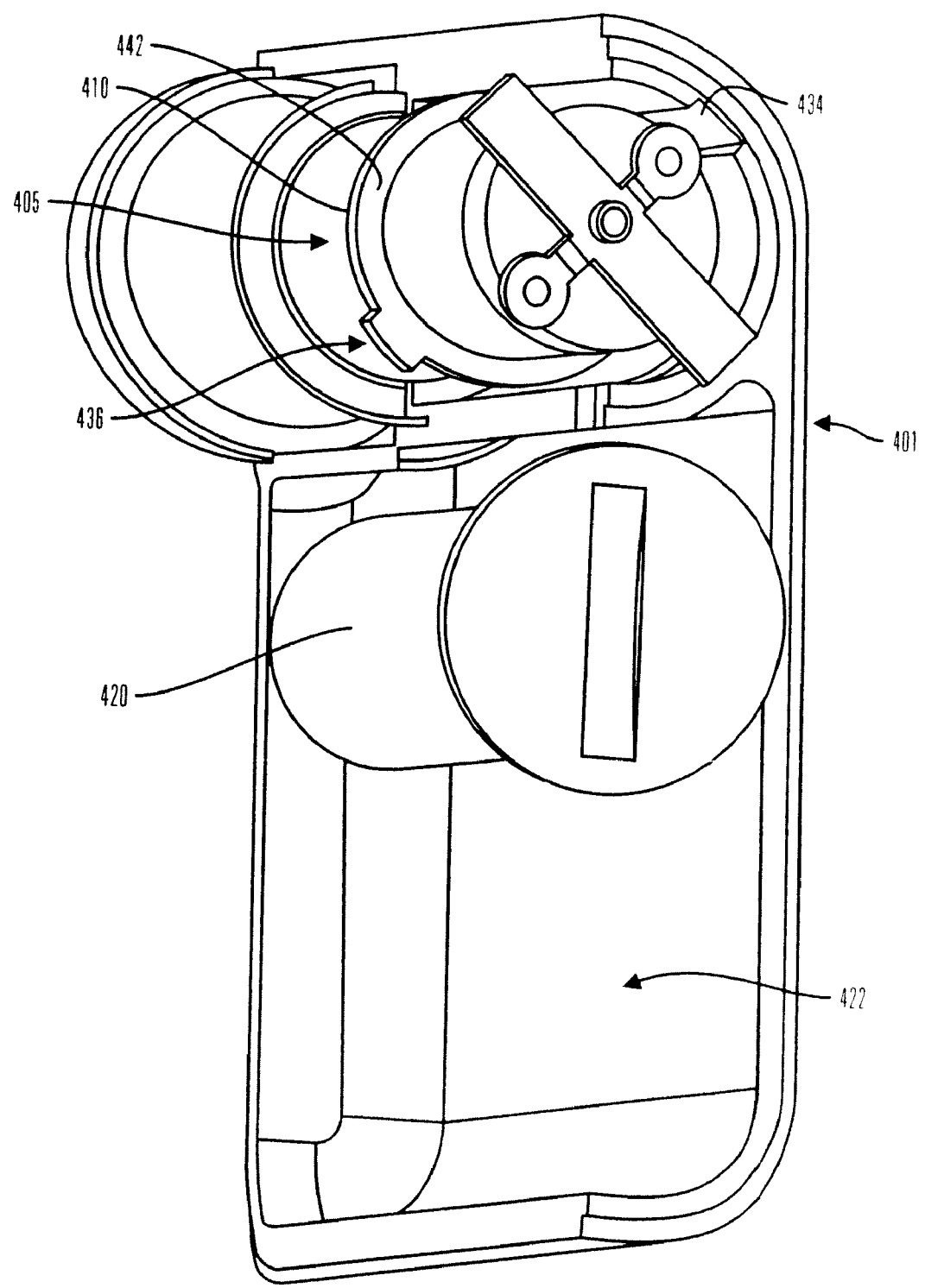
FIG. 8 is a cut-away perspective view of an anti-rotation device for use with the drive mechanism shown in FIG. 4.

FIG. 8 is a cut away perspective view of an anti-rotation device. The anti-rotation key 410 consists of a ring or collar 442 with two rectangular tabs 436 which are spaced 180° apart. Only one tab is visible in FIG. 8. The ring portion 442 of the key 410 surrounds and is attached to the end of the plunger slide 405 which is closest to the motor. Disposed in the housing 401 are two anti-rotation slots 434, only one of which is visible in FIG. 8. The anti-rotation slots 434 are sized to accept the rectangular tabs of the key 410. As the plunger slide 405 moves axially in response to the motor torque as previously described, the slots 434 will permit the key 410 to likewise move axially. However the slots 434 and the tabs 436 of the key 410 will prevent any twisting of the plunger slide 405 which might otherwise result from the torque generated by the motor.

Figure 9:
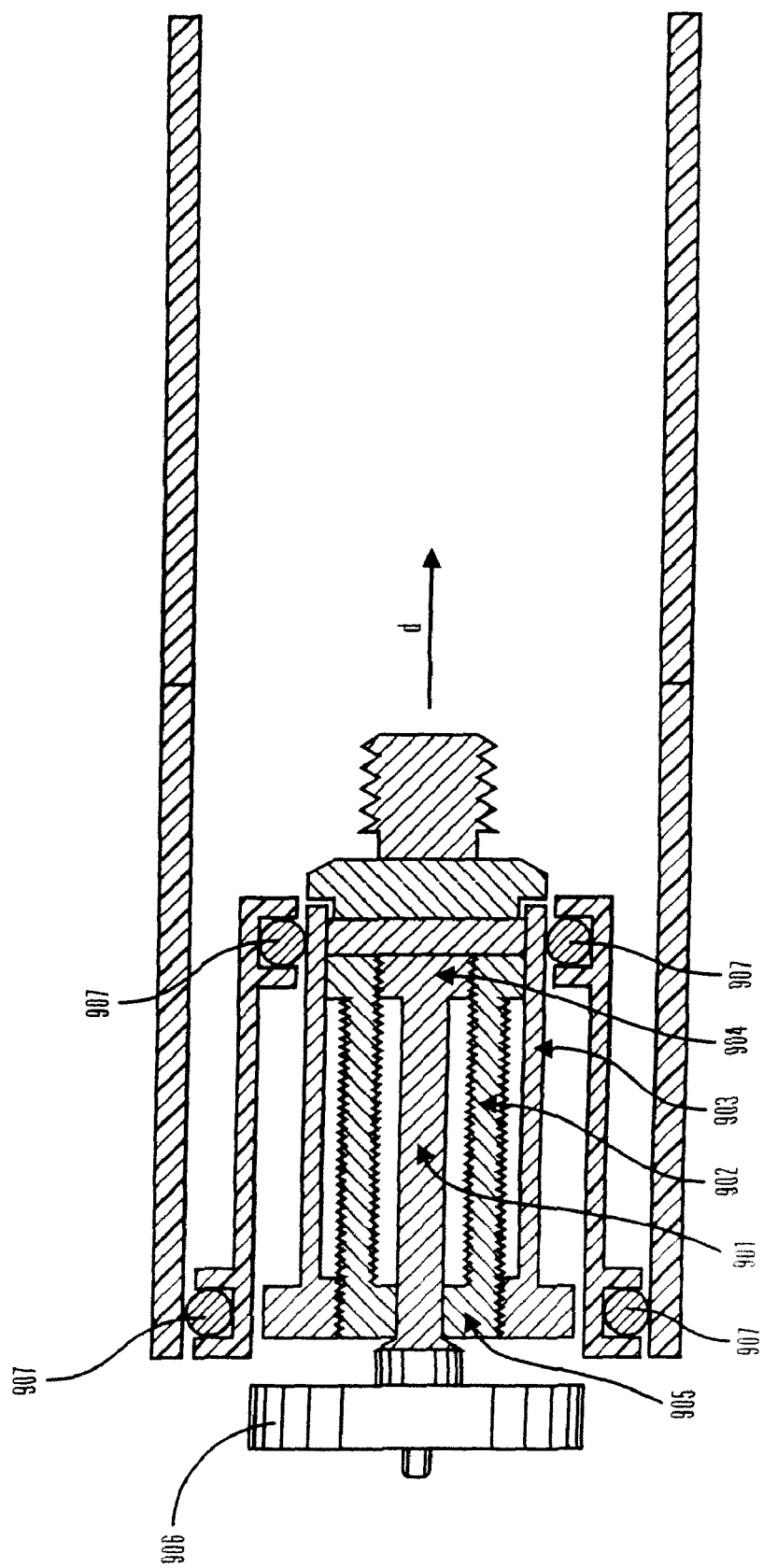
FIG. 9 is a cross-sectional view of a segmented (or telescoping) lead screw in accordance with an embodiment of the present invention.

FIG. 9 illustrates a split lead-screw (or plunger slide) design for use with a pump drive mechanism. The use of a split lead-screw or telescoping lead screw allows the use of an even smaller housing for the drive mechanism. A telescoping lead-screw formed from multiple segments allows the pump to minimize the dimensions of the drive mechanism, in either in-line or gear driven drive mechanisms.

An interior shaft 901 is rotated by a gear 906 which is coupled to a drive motor (not shown). This in turn extends a middle drive segment 902 by engaging with the threads of an internal segment 904. The middle segment 902 carries an outer segment 903 forward with it in direction d as it is extended to deliver fluid. When the middle segment 902 is fully extended, the internal segment 904 engages with a stop 905 on the middle segment 902 and locks it down from pressure with the threads between the middle and internal segments. The locked middle segment 902 then rotates relative to the outer segment 903 and the threads between the middle segment 902 and the outer segment 903 engage to extend the outer segment 903 in direction d to its full length.

The use of multiple segments is not limited to two or three segments; more may be used. The use of three segments reduces the length of the retracted lead-screw portion of the drive mechanism by half. In alternative embodiments, the outer segment may be connected to the motor and the inner segment may be the floating segment. In preferred embodiments, O-rings 907 are used to seal each segment relative to the other and to form a seal with the housing to maintain water sealing and integrity.

As previously noted, the construction of these pumps to be water resistant can give rise to operational problems. As the user engages in activities which expose the pump to varying atmospheric pressures, differential pressures can arise between the interior of the air tight/water-resistant housing and the atmosphere. Should the pressure in the housing exceed external atmospheric pressure, the resulting forces could cause the reservoir piston to be driven inward thus delivering unwanted medication. On the other hand, should the external atmospheric pressure exceed the pressure in the housing, then the pump motor will have to work harder to advance the reservoir piston.

To address this problem, a venting port is provided which resists the intrusion of moisture. Referring to FIG. 7b, venting is accomplished through the housing 401 into the reservoir cavity 601 via a vent port 605. The vent port can be enclosed by a relief valve (not shown) or covered with hydrophobic material. Hydrophobic material permits air to pass through the material while resisting the passage of water or other liquids from doing so, thus permitting water resistant venting. One embodiment uses a hydrophobic material such as Gore-Tex®, PTFE, HDPE, and UHMW polymers from sources such as W.I. Gore & Associates, Flagstaff, Ariz Porex Technologies, Fairburn, Ga., or DeWAL Industries, Saunderstown, R.I. It is appreciated that other hydrophobic materials may be used as well.

Figure 10A:
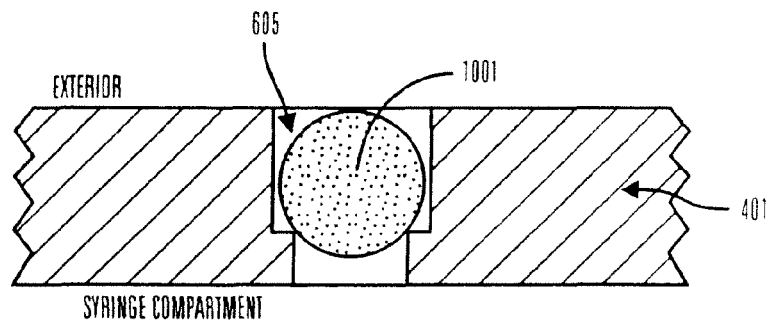
FIGS. 10a, 10b and 10c are cross-sectional views of various embodiments of venting ports for use with the drive mechanism of FIG. 4.
Figure 10B:
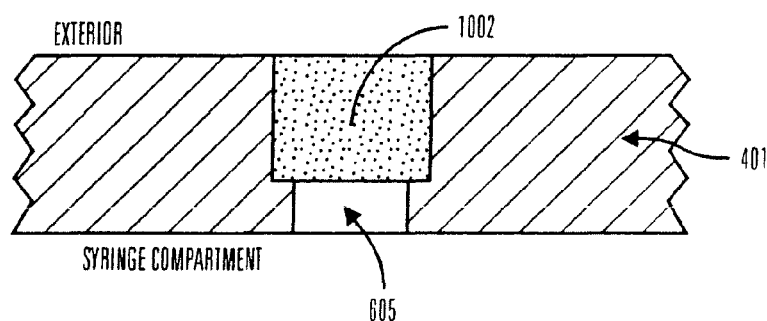
Figure 10C:
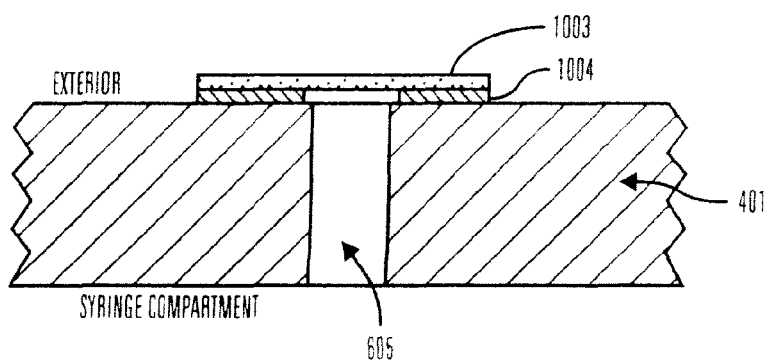

These materials are available in sheet form or molded (press and sintered) in a geometry of choice. Referring to FIGS. 10a-10c, preferred methods to attach this material to the housing 401 include molding the hydrophobic material into a sphere 1001 (FIG. 10a) or a cylinder 1002 (FIG. 10b) and pressing it into a cavity in the pre-molded plastic housing. Alternatively, a label 1003 (FIG. 10c) of this material could be made with either a transfer adhesive or heat bond material 1004 so that the label could be applied over the vent port 605. Alternatively, the label could be sonically welded to the housing. In either method, air will be able to pass freely, but water will not.

In an alternative embodiment (not shown), the vent port could be placed in the connector 431 which secures the reservoir 406 to the housing 401 and which also serves to secure and connect the reservoir 406 to the infusion set tubing (not shown). As described in greater detail in copending application Ser. No. 09/428,818, filed on Oct. 28, 1999, which application is incorporated by reference in its entirety, the connector and infusion set refers to the tubing and apparatus which connects the outlet of the reservoir to the user of a medication infusion pump.

An advantage of placing the vent port and hydrophobic material in this location, as opposed to the housing 401, is that the infusion set is disposable and is replaced frequently with each new reservoir or vial of medication. Thus new hydrophobic material is frequently placed into service. This provides enhanced ventilation as compared with the placement of hydrophobic material in the housing 401. Material in this location will not be replaced as often and thus is subject to dirt or oil build up which may retard ventilation. In yet another alternative embodiment however, vent ports with hydrophobic material could be placed in both the pump housing and in the connector portion of the infusion set.

Figure 11:
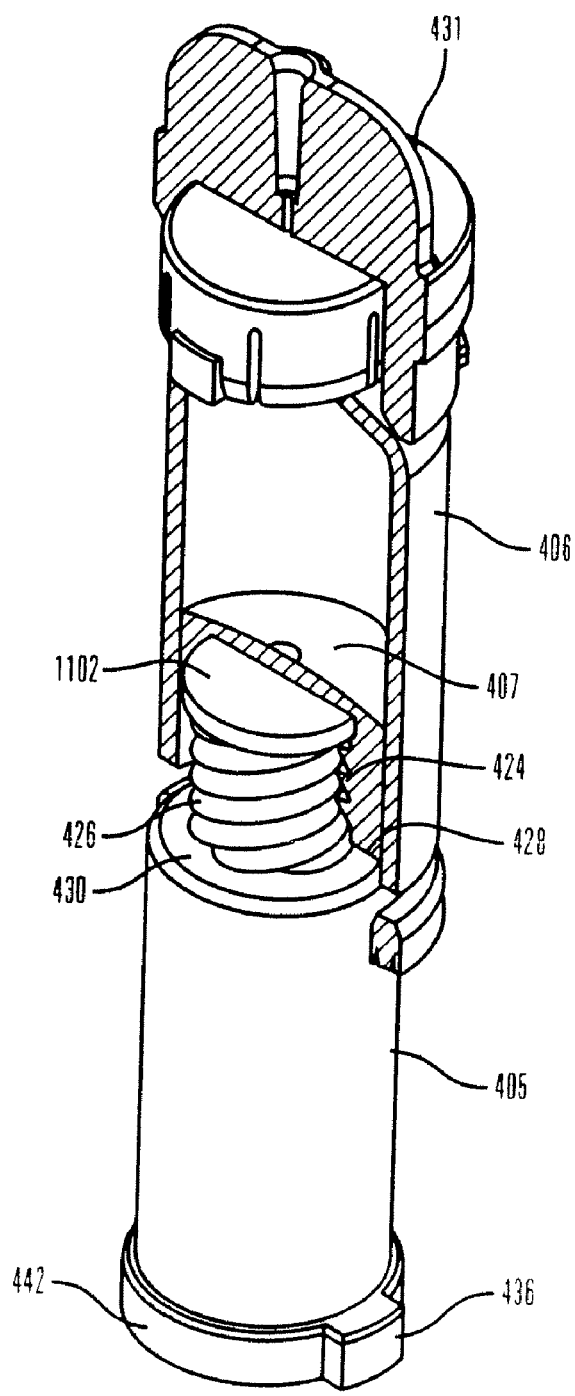
FIG. 11 is a partial, cross-sectional view of a reservoir and plunger slide assembly.

Regardless of the location of the vent port, there remains the possibility that the vent port can become clogged by the accumulation of dirt, oil, etc. over the hydrophobic material. In another feature of certain embodiments of the present invention, the releasable coupler can act to prevent unintentional medication delivery in those instances when the internal pump housing pressure exceeds atmospheric pressure. Referring to FIG. 11, the coupler includes threads formed in a cavity within the external face of the reservoir piston assembly 407. The threaded cavity 424 engages the threads of the male portion 426 which in turn is attached to the end 430 of the plunger slide 405.

This thread engagement reduces or prevents the effect of atmospheric pressure differentials acting on the water resistant, air-tight housing 401 (not shown in FIG. 11) from causing inadvertent fluid delivery. The threads of the male portion 426 act to inhibit or prevent separation of the reservoir piston assembly 407 from the plunger slide 405 which, in turn, is secured to the drive screw 404 (not shown in FIG. 11) by engagement of the external threads of the drive screw 404 with the internal threads of the plunger slide 405. As a result, the coupler resists movement of the reservoir piston assembly 407 caused by atmospheric pressure differentials.

When the reservoir 406 is to be removed, it is twisted off of the coupler male portion 426. The system electronics then preferably cause the drive motor 403 to rapidly rewind so that the plunger slide 405 is driven into a fully retracted position (FIGS. 4 and 6). A new reservoir 406, however, may not be full of fluid. Thus the reservoir piston assembly 407 may not be located in the furthest possible position from the reservoir outlet. Should the reservoir piston assembly 407 be in such an intermediate position, then it may not be possible to engage the threads of the male portion 426 of the coupler (which is in a fully retracted position) with those in the female portion 424 of the coupler in the reservoir piston assembly 407 upon initial placement of the reservoir.

In accordance with another feature of certain embodiments, the illustrated embodiment provides for advancement of the plunger slide 405 upon the insertion of a reservoir into the pump housing. The plunger slide 405 advances until it comes into contact with the reservoir piston assembly 407 and the threads of the coupler male portion 426 of the coupler engage the threads in the female portion 424 in the reservoir piston assembly 407. When the threads engage in this fashion in the illustrated embodiment, they do so not by twisting. Rather, they ratchet over one another.

In the preferred embodiment, the threads of the coupler male portion 426 have a 5 start, 40 threads per inch ("TPI") pitch or profile while the threads of the coupler female portion 424 have a 2 start, 40 TPI pitch or profile as illustrated in FIG. 11. Thus these differing thread profiles do not allow for normal tooth-to-tooth thread engagement. Rather, there is a cross threaded engagement.

The purpose of this intentional cross threading is to reduce the force necessary to engage the threads as the plunger slide 405 seats into the reservoir piston assembly 407. In addition, the 2 start, 40 TPI threads of the coupler female portion 424 are preferably made from a rubber material to provide a degree of compliance to the threads. On the other hand, the 5 start, 40 TPI threads of the male coupler portion 426 are preferably made of a relatively hard plastic. Other threading arrangements and profiles could be employed resulting in a similar effect.

If on the other hand, the threads had a common thread pitch with an equal number of starts given the same degree of thread interference (i.e., the OD of the male feature being larger than the OD of the female feature), then the force needed to insert the male feature would be pulsatile. Referring to FIG. 13a, as each thread tooth engages the next tooth, the insertion force would be high as compared to the point where the thread tooth passes into the valley of the next tooth. But with the cross threaded arrangement of the preferred embodiment, not all of the threads ride over one another at the same time. Rather, they ratchet over one another individually due to the cross-threaded profile. This arrangement results in less force required to engage the threads when the plunger slide moves axially, but still allows the reservoir to easily be removed by a manual twisting action.

While the advantage of utilizing a common thread pitch would be to provide a maximum ability to resist axial separation of the reservoir piston assembly 407 from the plunger slide 405, there are disadvantages. In engaging the threads, the peak force is high and could result in excessive delivery of fluids as the plunger slide 405 moves forward to seat in the cavity of the reservoir piston assembly 407. As described in greater detail in copending U.S. patent application Ser. No. 09/428,411 filed on Oct. 28, 1999, now issued U.S. Pat. No. 6,362,591, which application is incorporated by reference in its entirety, the pump may have an occlusion detection system which uses axial force as an indicator of pressure within the reservoir. If so, then a false alarm may be generated during these high force conditions.

It is desirable therefore to have an insertion force profile which is preferably more flat than that shown in FIG. 13a. To accomplish this, the cross threading design of the preferred embodiment causes the relatively soft rubber teeth of the female portion 424 at the end of the reservoir piston assembly 407 to ratchet or swipe around the relatively hard plastic teeth of the coupler resulting in a significantly lower insertion force for the same degree of thread interference. (See FIG. 13b) This is due to the fact that not all of the thread teeth ride over one another simultaneously. Moreover, the cross-sectional shape of the threads are ramped. This makes it easier for the threads to ride over one another as the plunger slide is being inserted into the reservoir piston. However, the flat opposite edge of the thread profile makes it much more difficult for the plunger slide to be separated from the reservoir piston.

When the plunger slide is fully inserted into the reservoir piston, the slide bottoms out in the cavity of the piston. At this point the presence of the hydraulic load of the fluid in the reservoir as well as the static and kinetic friction of the piston will act on the plunger slide. FIG. 13b shows the bottoming out of the plunger slide against a piston in a reservoir having fluid and the resulting increase in the axial force acting on the piston and the plunger slide. This hydraulic load in combination with the static and kinetic friction is so much higher than the force required to engage the piston threads that such a disparity can be used to advantage.

Figure 2:
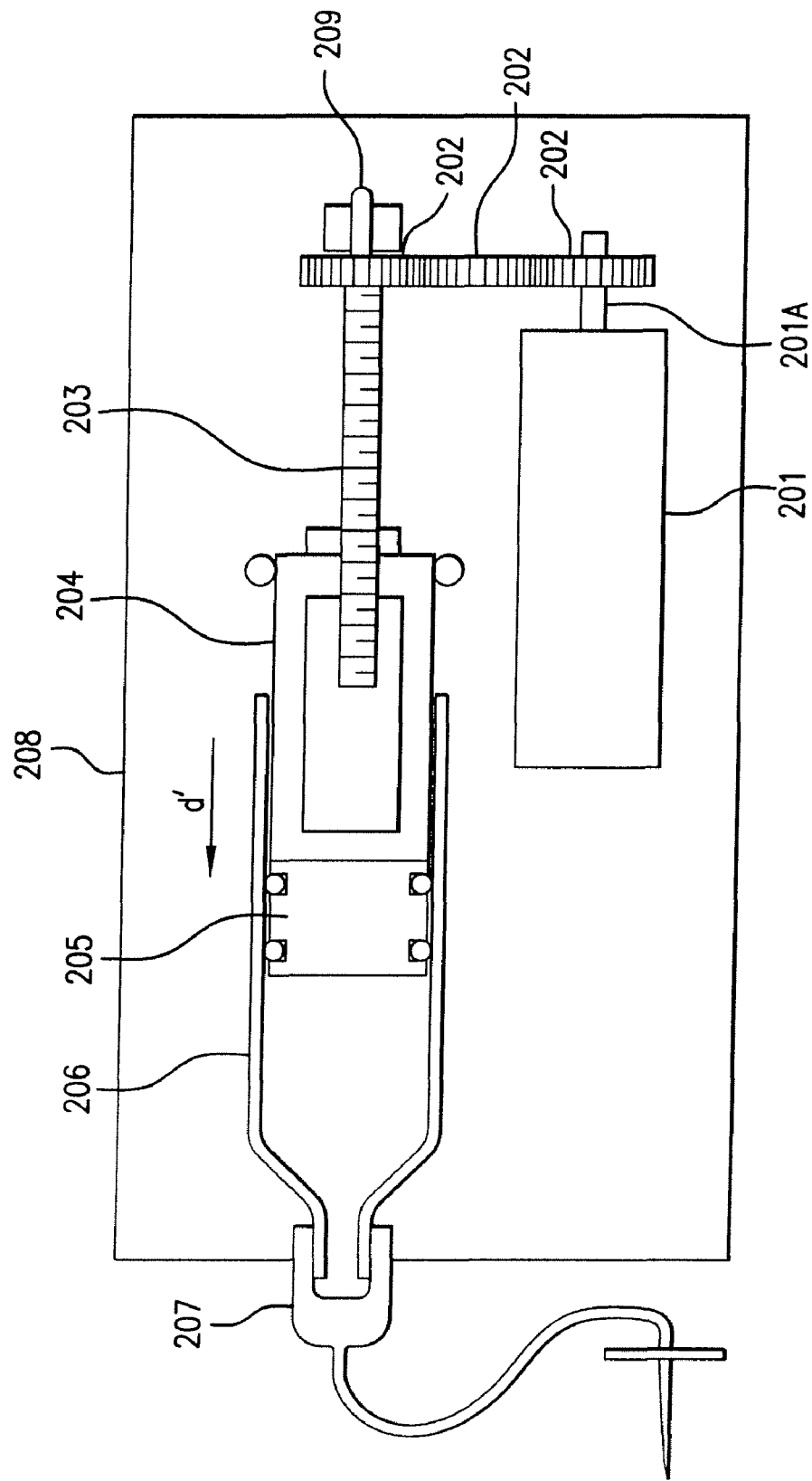
FIG. 2 is a side plan view of another conventional lead-screw drive mechanism.
Figure 3A:
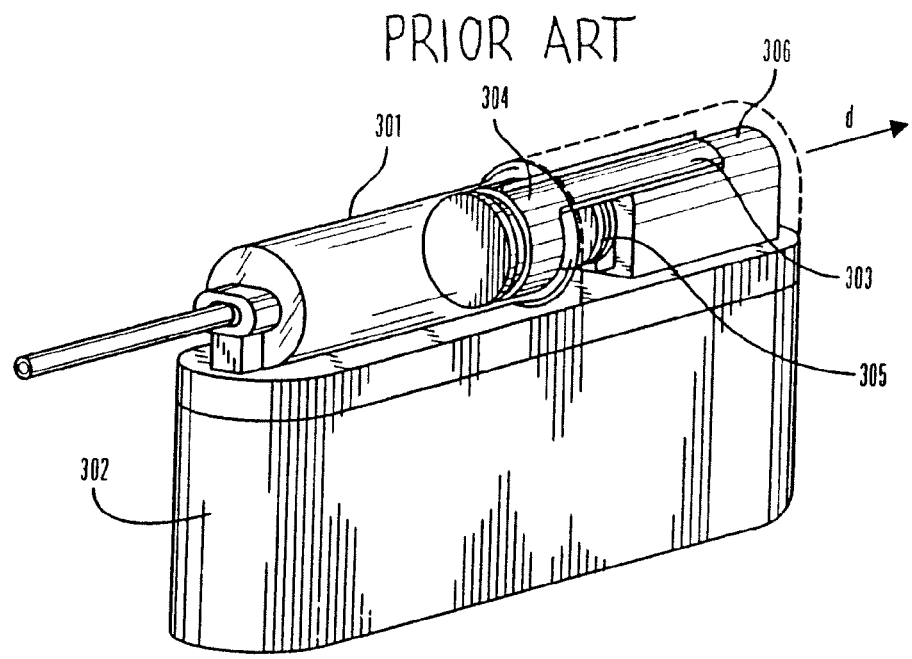
FIG. 3a is a perspective view of another conventional lead-screw drive mechanism.
Figure 3B:
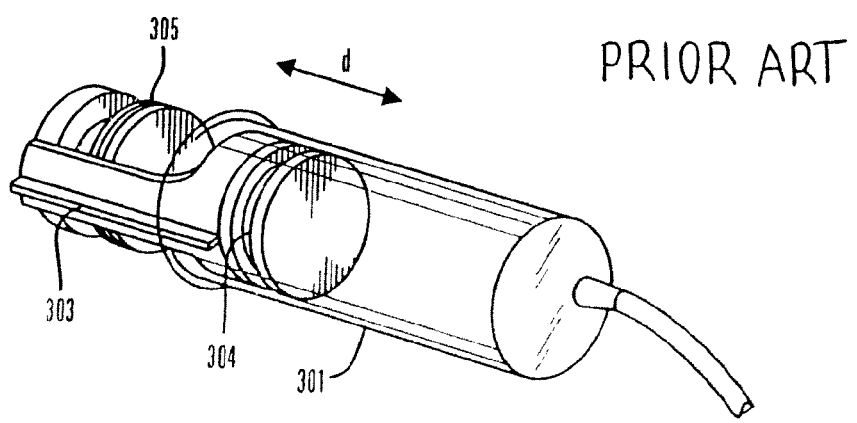

The fluid pressure and occlusion detection systems described it U.S. provisional patent application Ser. No. 60/243,392 filed Oct. 26, 2000, later filed as a regular U.S. application Ser. No. 09/819,208 filed on Mar. 27, 2001, now issued as U.S. Pat. No. 6,485,465 or in U.S. patent application Ser. No. 09/428,411, filed Oct. 28, 1999, now issued U.S. Pat. No. 6,362,591 (all of which are incorporated herein by reference in their entireties) or known pressure switch detectors, such as those shown and described with reference to FIGS. 1 and 2, can be used to detect the fluid back pressure associated with the bottoming out of the plunger slide against the piston. Certain sections of the incorporated references will be discussed below with regards to the error detection of the fluid force sensor and occlusion detection systems below in reference to FIGS. 19-23(a & b), which is related to the fluid back pressure associated with the bottoming out of the plunger slide against the piston.

A high pressure trigger point of such a pressure switch or occlusion detection system can be set at a point above the relatively flat cross thread force as shown in FIG. 13b. Alternatively, the ramping or the profiles of such back pressure forces can be monitored. When an appropriate limit is reached, the pump system electronics can send a signal to stop the pump motor. Thus the pump drive system is able to automatically detect when the plunger slide has bottomed out and stop the pump motor from advancing the plunger slide.

Referring to FIGS. 11 and 12, the 5 start, 40 TPI (0.125" lead) thread profile of the coupler male portion 426 was chosen in consideration of the thread lead on the preferred embodiment of the connector 431. The connector 431 is secured into the pump housing with threads 433 (FIG. 7b) having a 2 start, 8 TPI (0.250" lead) profile. Therefore the 0.250" lead on the connector is twice that of the reservoir piston assembly 407 which is 0.125". This was chosen to prevent inadvertent fluid delivery during removal of the reservoir from the pump housing, or alternatively, to prevent separation of the reservoir piston assembly 407 from the reservoir 406 during removal from the pump housing. When the connector 431 is disengaged from the pump, the connector 431 as well as the reservoir 406 will both travel with the 0.250" lead. Since the threaded coupler lead is 0.125", the plunger slide 405 will disengage somewhere between the 0.125" lead of the threaded coupler and the 0.250" lead of the infusion set 1103. Therefore, the rate that the reservoir piston assembly 407 is removed from the pump is the same down to half that of the reservoir 406/connector 431. Thus any medication, which may be present in the reservoir 406 will not be delivered to the user. Additionally, the length of the reservoir piston assembly 407 is sufficient such that it will always remain attached to the reservoir 406 during removal from the pump. Although the preferred embodiment describes the plunger slide 405 having a coupler male portion 426 with an external thread lead that is different from the connector 431, this is not necessary. The thread leads could be the same or of an increment other than what has been described.

The 2 start thread profile of the coupler female portion 424 on the reservoir piston assembly 407 of the preferred embodiment provides another advantage. Some versions of these reservoirs may be designed to be filled by the user. In such an instance, a linear actuation member comprising a handle (not shown) will need to be screwed into the threaded portion of the reservoir piston assembly 407 in order for the user to retract the reservoir piston assembly 407 and fill the reservoir. The number of rotations necessary to fully insert the handle depends upon the distance the handle thread profile travels to fully engage the reservoir piston assembly 407 as well as the thread lead.

For example, a single start, 40 TPI (0.025" lead) thread requires 4 complete rotations to travel a 0.10" thread engagement. However, a 2 start, 40 TPI (0.050" lead) thread only requires 2 complete rotations to travel the 0.10" thread engagement. Therefore, an additional advantage of a 2 start thread as compared to a single start thread (given the same pitch) is that half as many rotations are needed in order to fully seat the handle.

In alternative embodiments which are not shown, the end of the plunger slide 405 may include a détente or ridge to engage with a corresponding formation in the reservoir piston assembly 407 to resist unintended separation of the plunger slide 405 from the reservoir piston assembly 407. In other embodiments, the plunger slide 405 is inserted and removed by overcoming a friction fit. Preferably, the friction fit is secure enough to resist movement of the reservoir piston assembly 407 relative to the plunger slide 405 due to changes in air pressure, but low enough to permit easy removal of the reservoir 406 and its reservoir piston assembly 407 from the plunger slide 405 once the fluid has been expended. In other embodiments, the détente or ridge may be spring loaded or activated to grasp the reservoir piston assembly 407 once the drive mechanism has been moved forward (or extended), but is retracted by a switch or cam when the drive mechanism is in the rearmost (or retracted) position. The spring action could be similar to those used on collets. In other embodiments of the inventions, the threaded coupler may be engaged with the threaded cavity of the reservoir piston by twisting or rotating the reservoir as it is being manually placed into the housing.

As previously mentioned, some pump systems may have an occlusion detection system which uses the axial force on the drive train as an indicator of pressure within a reservoir. One problem faced by such occlusion detection systems, however, is the system compliance associated with reservoir fluid back pressures. As previously mentioned, the force on a piston assembly resulting from increased back pressures can deform a piston which is constructed of relatively flexible material such as rubber. Should an occlusion arise in the fluid system, this deformation can reduce the rate at which fluid back pressures increase. This in turn can increase the amount of time required for the system to detect an occlusion—a situation which may be undesirable.

To address this problem, an insert 1201 which is made of hard plastic, stainless steel or other preferably relatively stiff material is disposed in the upper portion of the reservoir piston assembly 407. (FIG. 12) The insert 1201 of the illustrated embodiment provides stiffness to the rubber reservoir piston assembly 407. This can reduce undesirable compliance which is associated with the reservoir.

Figure 14:
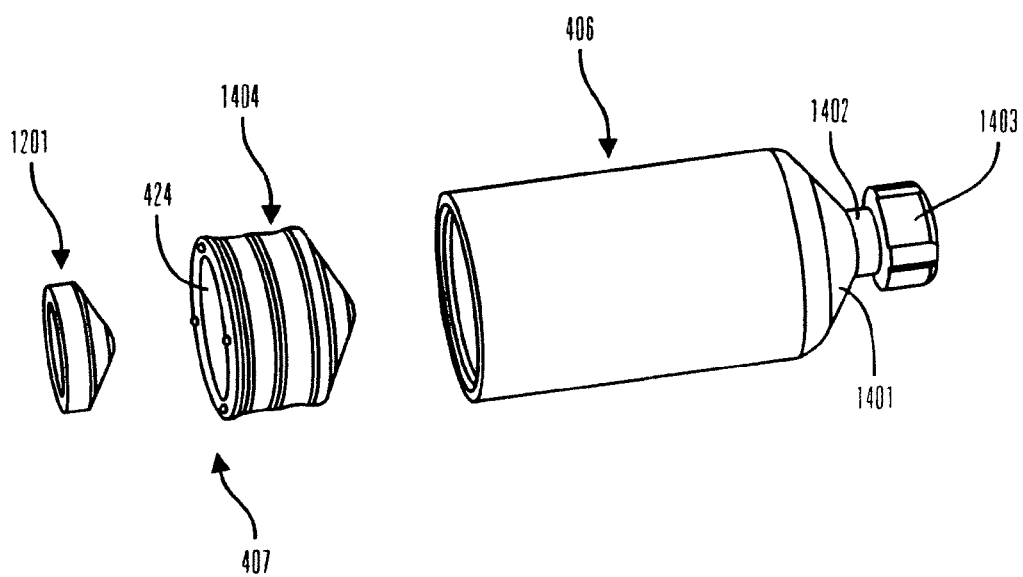
FIG. 14 is an exploded view of a reservoir, a piston, and an insert.

FIG. 14 shows an industry standard reservoir 406 and the piston assembly 407 comprising a piston member 1404 and an insert 1201. One end of the reservoir 406 has a generally conical-shaped end portion 1401 which tapers to a neck 1402. A swage 1403 is secured to the neck thereby forming a fluid-tight seal. The insert 1201 is placed in the cavity 424 of the piston member 1404 which in turn is placed in the opposite end of the reservoir 406.

Figure 15A:
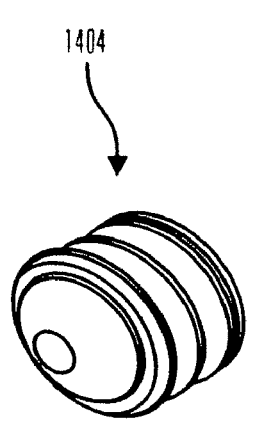
FIG. 15a is a perspective view of a reservoir piston.
Figure 15B:
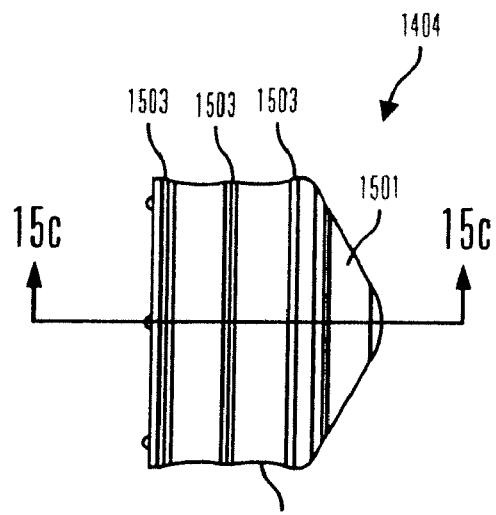

FIGS. 15a and 15b show the piston member 1404 which is adapted to receive the insert 1201 (FIG. 14). The piston member 1404 is further adapted to be slidably mounted within the reservoir 1401 and to form a fluid-tight barrier therein. The exterior of the piston member 1404 includes a generally cylindrical side wall 1502 and an external proximate side 1501 having a generally conical convex shape which is adapted to conform to the conical-shaped end portion 1401 of the reservoir 406 (FIG. 14). This geometry reduces the residual volume of fluid remaining in the reservoir 406 after the piston assembly 407 is fully advanced. The piston member's side wall 1502 has a plurality of ridges 1503 which form a friction fit with the interior of the reservoir side wall thereby forming a fluid-resistant seal.

Figure 15C:
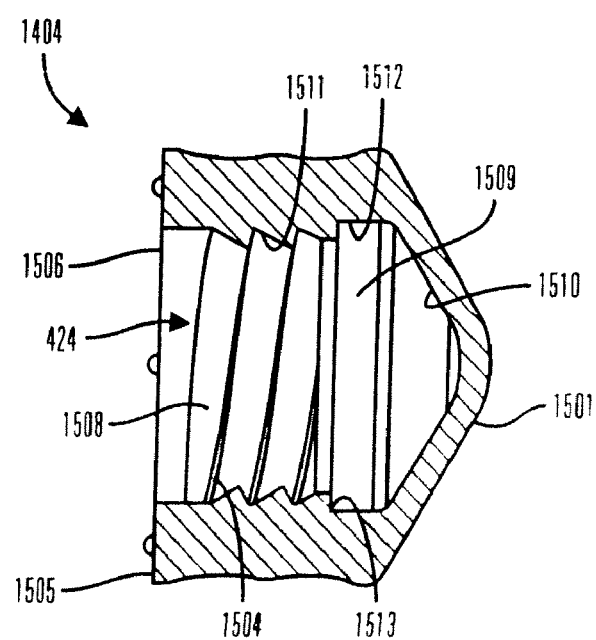
FIG. 15c is a cross-sectional view of the piston along lines 15c-15c of FIG. 15b.

Referring to FIG. 15c, the piston member 1404 has an external distal side 1505 which is opposite to the external proximate side 1501 which in turn is adapted to contact any fluid which might be present in the reservoir. The external distal side 1505 has an opening 1506 leading into the threaded cavity 424. The cavity 424 comprises a first chamber 1508 extending from the external distal side 1505 into the cavity 424 and a second chamber 1509 extending from the first chamber 1508 to an internal proximate wall 1510 which is disposed adjacent to the external proximate side 1501 of the piston member 1404.

The first chamber 1508 is defined by a generally cylindrically-shaped first wall 1511 extending axially from the external distal side 1505 into the cavity 424. The first wall 1511 includes threads 1504 formed on the wall which are adapted to couple with any linear actuator member, such as for example, the threads of the male portion 426 of the plunger slide 405 as previously described (FIG. 11). The second chamber 1509 is defined by a generally cylindrically-shaped second wall 1512 extending axially from the generally cylindrically-shaped first wall 1511 into the cavity 424 and by the internal proximate wall 1510. The generally cylindrically-shaped second wall 1512 has a radius which is greater than that of the generally cylindrically-shaped first wall 1511. A ledge 1513 extends from the generally cylindrically-shaped first wall 1511 to the generally cylindrically-shaped second wall 1512. The internal proximate wall 1510 forms the end of the second chamber 1509 and is generally concave conical in shape. Thus the thickness of that portion of the first member which is between the internal proximate wall 1510 and the external proximate side 1501 is generally uniform.

Referring to FIGS. 16a-16c, the insert 1201 is a solid member which has a planar back wall 1602, a generally cylindrical side wall 1603, and a conical face portion 1601 which terminates in a spherically-shaped end portion 1604. In one embodiment, the planar back wall 1602 is 0.33 inches in diameter, the cylindrical side wall 1603 is approximately 0.054 inches in length, the conical face portion 1601 is approximately 0.128 inches in length, and the spherically-shaped end portion 1604 has a radius of curvature of approximately 0.095 inches.

The face portion 1601 and the end portion 1604 are adapted to mate with the internal proximate wall 1510 and the back wall 1602 is adapted to seat against the ledge 1513 of the piston member 1404 (FIG. 15c). When inserted, the insert face portion 1601 and the external proximate side 1501 are in a generally parallel spaced-apart relationship. The insert 1201 is a relatively incompressible member which can be made of stainless steel or relatively stiff plastic or any other material which preferably has stiffness properties which are greater than that of the external proximate side 1501 of the piston member 1404. If a hard plastic material is selected, however, it preferably should be a grade of plastic which can withstand the high temperatures associated with an autoclave.

Figure 17:
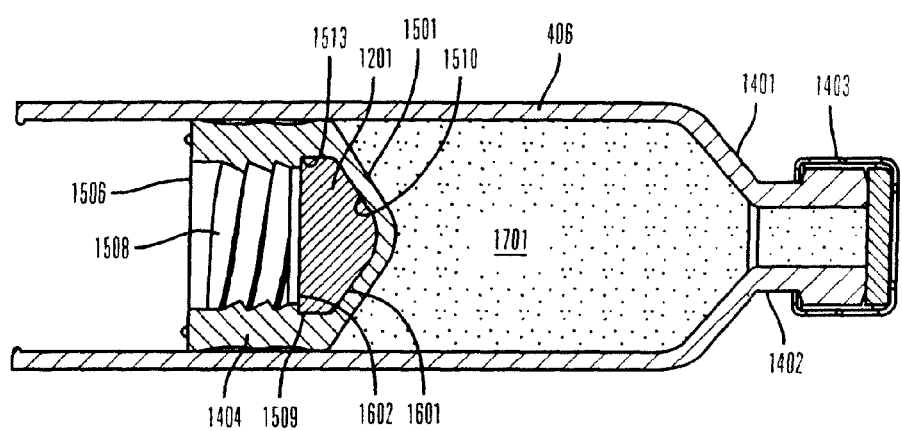
FIG. 17 is a cross-sectional view of a reservoir, reservoir piston, and insert.

FIG. 17 shows the reservoir 406 with the piston member 1404 and the insert 1201 as assembled. As previously mentioned, the ledge 1513 supports the planar back 1602 of the insert 1201 and secures it into place. Because the piston member 1404 is constructed of rubber or other relatively flexible material, it can deflect sufficiently during assembly to permit the insert 1201 to be inserted in the opening 1506 and through the first chamber 1508 and then positioned in the second chamber 1509. The conical face portion 1601 of the insert 1201 mates with the internal proximate wall 1510 of the piston member 1404, thus permitting a reduced thickness of rubber which is in direct contact with fluid 1701. This reduced thickness of rubber or other flexible material minimizes the compliance which might otherwise be caused by the back pressure of the fluid 1701 acting on the external proximate side 1501 of the piston member 1404.

It should be appreciated that although the insert member 1201 depicted in FIGS. 14-17 is removable from the piston member 1404, alternative embodiments of the present invention include a piston assembly in which there are no openings or open cavities and in which an insert member is encased in such a manner so as to be not removable.

Figure 18:
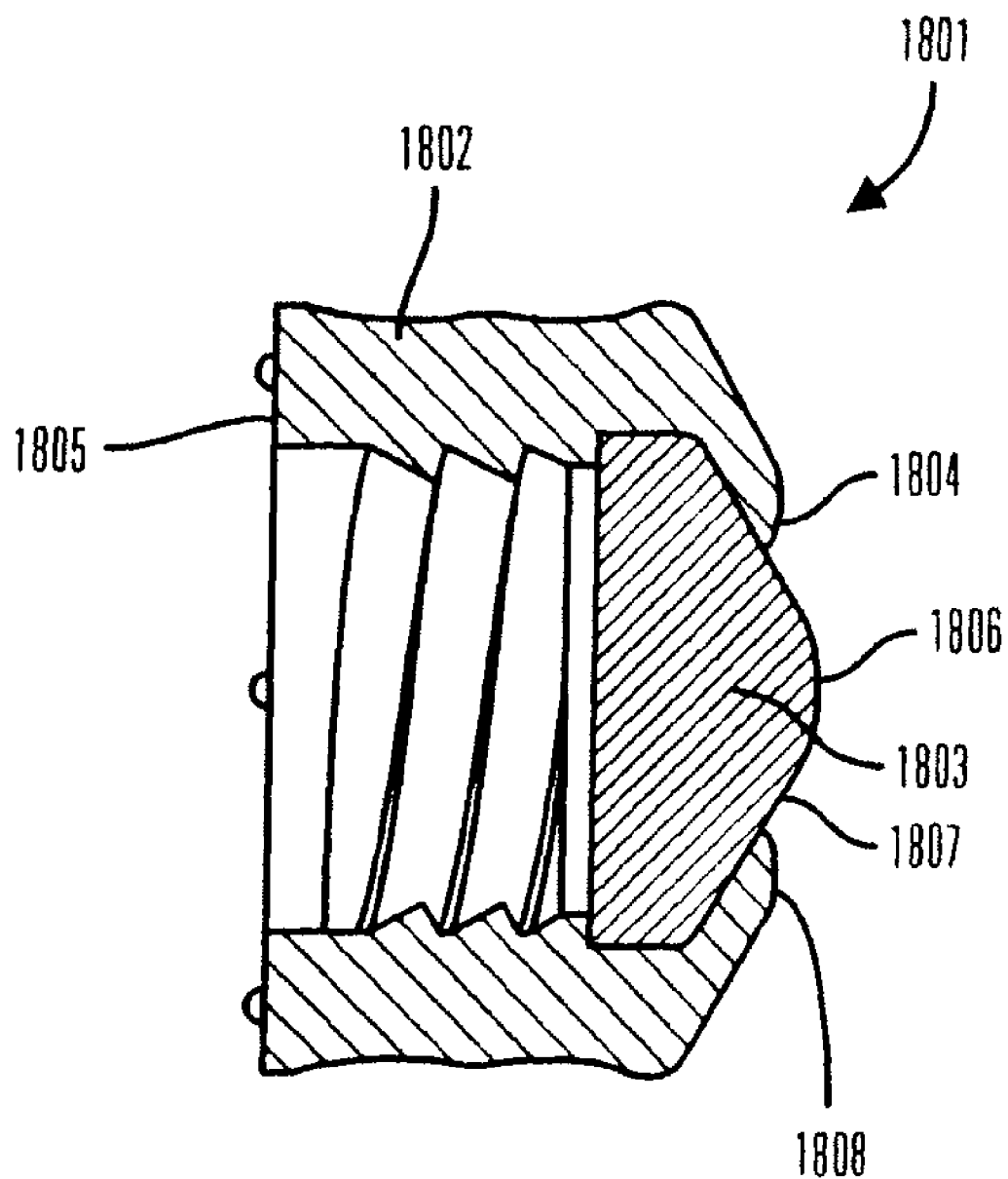
FIG. 18 is a cross-sectional view of a piston and piston insert according to an alternative embodiment of the present invention.

The insert member of the above-described embodiments is not adapted to contact the fluid in a reservoir. However, FIG. 18 shows yet another alternative embodiment where a portion of an insert member is adapted to contact reservoir fluid. A piston assembly 1801 comprises a piston member 1802 and an insert 1803. The piston member 1802 is adapted to be slidably mounted within a reservoir (not shown in FIG. 18) and is further adapted to form part of a fluid-tight barrier within the reservoir. The piston member 1802 has an external proximate side 1804 and an external distal side 1805. The external proximate side 1804 is adapted to contact the reservoir fluid and is made of an elastomeric material, such as rubber.

The insert 1803 is substantially contained within the piston member 1802 and has a face 1806 which is made of a material, such as stainless steel or hard plastic, having a stiffness which is greater than that of the piston member 1802. The insert face 1806 has an exposed portion 1807 and an enclosed portion 1808. The exposed portion 1807 is adapted to contact the fluid within the reservoir whereas the enclosed portion 1808 is enclosed or covered by the external proximate side 1804 of the piston member 1802. Therefore, the insert 1803 extends past the external proximate side of the piston member 1802 and is adapted for contact with the fluid to complete the fluid-tight barrier within the reservoir. Thus the arrangement of the insert 1803 in this fashion provides the necessary stiffness to the piston assembly 1801 to reduce system compliance.

It should be appreciated that while the piston members and inserts described above include conical geometries, other geometries can be used. For example in an alternative embodiment shown in FIG. 11, an insert 1102 has a disc shape with relatively flat faces. This also can provide the necessary stiffness to the piston assembly 407 to reduce system compliance.

In yet further embodiments (not shown), an insert member is an integral part of a male portion of a plunger slide assembly which is adapted to fit within a piston assembly cavity. The male portion of the slide assembly (i.e., the insert member) is further adapted to abut an internal proximate wall within the cavity thus providing increased stiffness to that portion of the piston assembly which is in contact with reservoir fluid.

It can be appreciated that the design of FIGS. 4-18 results in an arrangement where the plunger slide 405 is reliably but releasably coupled to the drive screw 404. When it is time to replace the reservoir 406, it can be detached from the male end of the coupler without affecting the plunger/drive screw engagement. Moreover in one embodiment, the plunger slide 405 is shaped as a hollow cylinder with internal threads. Thus it completely encircles and engages drive screw 404. When the plunger slide 405 is in a relatively retracted position, it encloses any gears which couple the motor 403 with the drive screw 404 thus achieving an extremely compact design. A vent port covered with hydrophobic material as well as a threaded coupler provide redundant means for permitting exposure of the pump to changing atmospheric pressures without the unintended delivery of medication. A reservoir piston assembly 407 includes an insert member 1201 which increases the stiffness of the piston assembly 407 thus reducing fluid system compliance.

In another aspect of the present invention, the above discussed drive system allows for improved occlusion detection and other error detection systems. Relevant text from U.S. patent application Ser. No. 09/428,411, filed Oct. 28, 1999, now issued U.S. Pat. No. 6,362,591, which was incorporated by reference, describes the occlusion detection scheme as follows:

The occlusion detector measures increased reservoir pressure indirectly by monitoring one or more motor parameters, such as voltage, current, running time, or rotational or linear displacement. It is known in the art that torque developed by a brushed DC motor is directly proportional to the current supplied to it at steady state. Therefore, in a screw type drive system, as the axial load increases due to increased fluid pressure within the reservoir, more motor torque is required to drive the system. Should there be an occlusion, the pressure inside the reservoir will exceed a predetermined threshold. Thus the current necessary to drive that load will exceed a predetermined current threshold and the electronics will be flagged to cease further delivering. In addition, an audible, tactile and/or display alarm typically is triggered.

However, care must be employed when clearing this alarm if the occlusion still exists and there is still a high pressure state in the reservoir. Since the motor must operate to obtain an indication of pressure within the reservoir, more and more pressure can potentially be developed within the system. If the motor is not in operation, there is no current flowing and negligible torque on the motor body. Therefore, when an occlusion exits distal from the reservoir due to pinched tubing for example, then the measured property will indicate this only during each motor delivery increment.

If the user clears the alarm and attempts to deliver medication again when the occlusion in fact was not removed, additional pressure will be generated within the fluid system. Assuming that the system is programmed to continue to alarm when the pressure (or motor current) is above the set point, then continued alarming will occur. Thus the user may on several occasions attempt to clear the alarm before locating and correcting the source of the occlusion.

When the occlusion is finally cleared, there could be excess pressure developed in the system which could result in the delivery of a bolus of medication larger than that which should be delivered. The improved occlusion detection system disclosed herein protects against this by causing the pump to rewind by some predetermined amount following each occlusion alarm. By rewinding the pump by, say, one delivery pulse, the occlusion alarm will trigger if the occlusion still exists. However, it will do so at the same maximum pressure as programmed and not at above this value.

On a drive system that is bi-directional, the current measurement can also be used as an indicator of system wear. Over the life of the product, it is expected that the torque required to drive the system will change over time due to wear of the dynamic components and their interfaces. Since the torque required to rewind a bi-directional system is due to the drive system's frictional factors, the current to rewind can be recorded and is proportional to this torque.

As the system wears, the torque and therefore the current to rewind will change. By storing the rewind current, this can be used to calibrate the system. An averaged baseline rewind current can be determined and used to adjust the driving force baseline which is the torque (or current) required to advance the drive system when no other external forces, such as a syringe with fluid, are present. An alternative method would be to rewind the system, and then immediately thereafter, obtain the forward or driving baseline current by driving the system forward for some distance and recording it, after which, the system is rewound again. The advantage of using either method is that the calibration can be automatic and transparent to the user.

Figure 19:
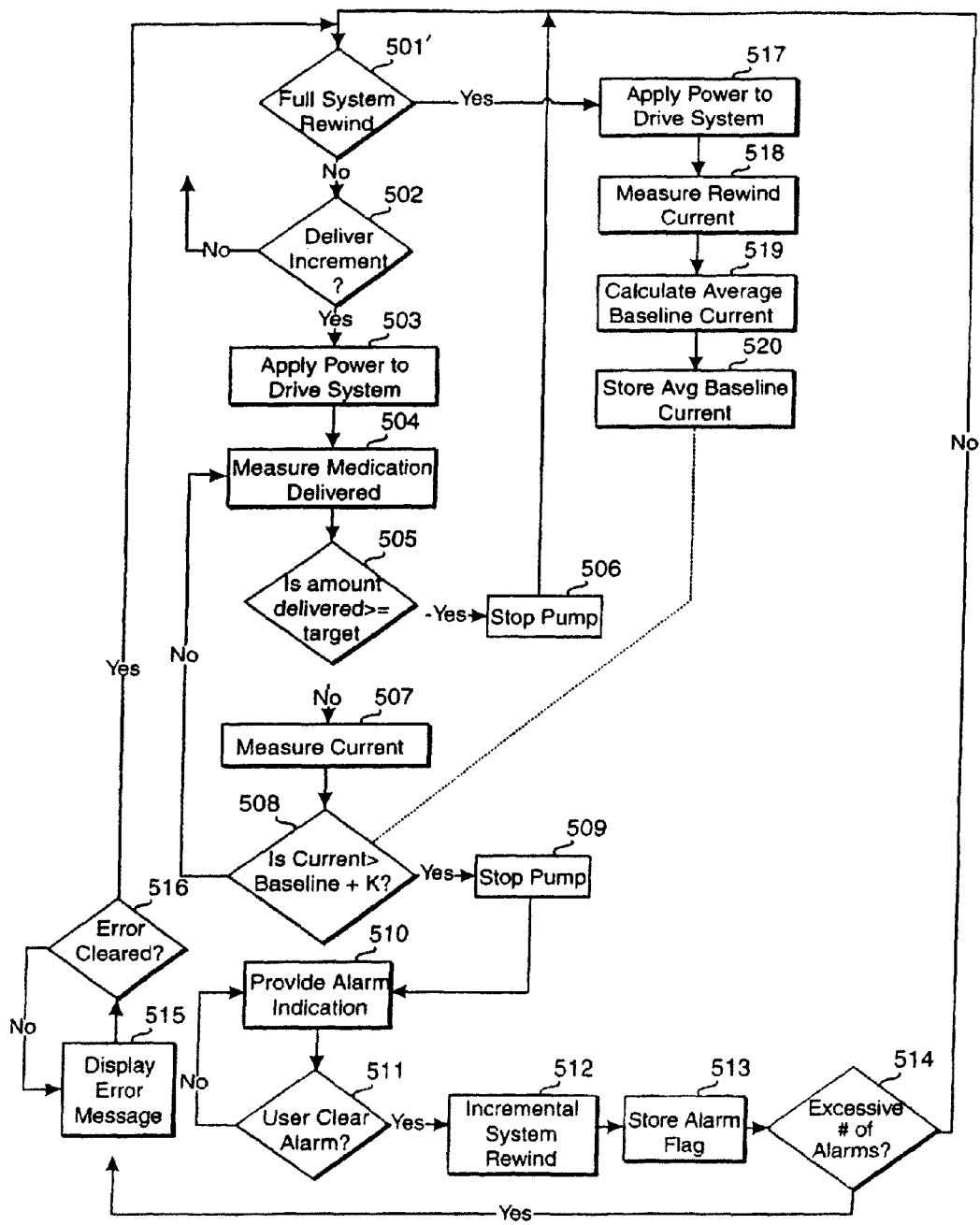
FIG. 19 illustrates logic for detecting occlusions in accordance with an embodiment of the present invention.

FIG. 19 illustrates the logic in one embodiment of the detector wherein motor current is measured for detecting a system occlusion. Control begins at block 501' where the system determines whether it is necessary to fully rewind the pump drive system. Conditions requiring such a rewind of the drive system will be discussed below. If the system is not to be rewound, then a determination is made whether it is time for an increment of medication is to be delivered (block 502). This determination is a function of the programming which is unique to the medical condition of each user, the type of medication being provided, or the like. If it is not time to deliver medication, then the program loops to the start for additional time to elapse or for the receipt of other control commands.

However, if it is time for delivery of an increment of medication, control transfers to block 503 where power is applied to the pump motor thus causing medication to be dispensed from the reservoir. Next, the amount of medication delivered from the reservoir is measured (block 504). This can be accomplished directly or indirectly in several ways, including measuring (1) encoder counts, (2) pump operation time, (3) reservoir plunger position location, velocity or acceleration, (4) the location of any moveable component on the pump drive train, or (5) the mass or volumetric flow of the liquid.

A determination is then made as to whether the amount of medication delivered is sufficient (block 505). If it is sufficient, control is transferred to block 506 where the pump is stopped and the program loops to the beginning. If on the other hand, the pump is continuing to run, but the programmed dosage has not yet been delivered, then the pump motor current is measured (block 507). If there is an occlusion in the system, an increase in reservoir fluid pressure will likely result. This, in turn, can cause greater motor torque and current as the motor attempts to advance the reservoir plunger against this fluid pressure. Thus, if the measured motor current is some amount greater than a known, average baseline motor current, which may be established when there was no occlusion condition, then it is determined that an occlusion condition has likely occurred.

Not only can this current measurement indicate an occlusion condition, this motor current can provide feedback as to drive system characteristics, performance, and functionality, especially with the addition of an encoder. If for example, there was a failure of the gearbox causing the motor to be unable to rotate, the measured current would be high (above predetermined threshold settings) and the encoder would not increment. This would be an indication of a drive system fault. For the inline drive system, a failure of the gearbox, screw, or slide interface would be indicated by this condition.

Referring to FIG. 19, at block 508 the value of the average baseline current is retrieved from a storage location in memory represented by block 520. This value is compared with the current measured at the present time and a determination is made whether the present current exceeds the average baseline by a certain amount. If it does not, then the pump continues to run and control loops to block 504 where the amount of medication delivery is again measured. On the other hand, if the present current exceeds the average baseline by a selected amount, then the pump motor is stopped and an alarm indication, audible, tactile and/or visible, is given (blocks 509 and 510).

Control transfers to block 511 where the system is monitored for clearing of the alarm. If the alarm has not been cleared, then control loops to block 510 where the alarm will continue to display. If the alarm has been cleared by the user, then control transfers to block 512 where the drive system is rewound by an incremental amount. This rewinding serves to decrease the reservoir fluid back pressure which in turn inhibits or prevents the delivery of an excessive bolus of medication should the user experience a series of occlusion alarms before successfully clearing the occlusion.

Control then transfers to block 513 where an alarm flag is stored. A determination is made whether there have been an excessive number of recent alarms (block 514). If there have not, then control loops to the beginning (block 501) where the above described process is repeated. On the other hand, if there have been an excessive number of recent alarms, control transfers to block 515 where an error or reset message is displayed to the user. This message typically would be used to advise the user to contact the manufacturer or some authorized repair facility to determine the cause of the excessive number of alarms. This error message will continue to be displayed until the error is cleared (block 516) at which point control loops to the beginning (block 501) where the process is repeated.

Returning to block 501', there are times when a full rewind of the drive system may be required. One instance would be when the medication reservoir in the pump housing is empty and a new reservoir must be inserted. Thus, when it has been determined that rewinding of the drive system is desired (either by user command or otherwise), control transfers to block 517 where power is applied to the pump motor. As the motor is running in a rewind direction, the pump motor current is measured (block 518). An alternative method would be to obtain the forward or driving baseline current by driving the system forward (possibly immediately following rewind) for some distance and recording it, after which the system may need to be rewound again. Because the motor is running in the opposite direction (or forward following rewind), typically there is little or no fluid pressure against which the pump motor is driving. Thus the current measured during this phase can be used as a baseline for comparison in detecting occlusions.

Control transfers to block 519 where the previous average baseline current value is retrieved from a storage location in memory (block 520) and an updated average baseline current is calculated. This updated value is then placed in the storage location, (block 520), where it will be available for the next current measurement and comparison at block 508.

The value of repeatedly updating the average baseline current is to provide a calibration against changing drive train friction forces. The lead screw mechanism of many pump designs includes seals, a drive nut, a lead screw/motor coupling, and a bearing. All of these components have frictional properties. These properties are known to change over time and thus the motor torque and current required to advance a reservoir plunger are likely to change. This therefore provides a more accurate baseline against which current can be measured for the detection of an occlusion.

Although the foregoing description involved the measurement of motor current, other motor parameters which vary with differing fluid back pressures can be measured with like effect. Such parameters may include motor voltage, linear displacement, rotary displacement, torque, rotor speed, and the like.

For example, one alternative embodiment of the occlusion detector involves the use of a motor position encoder which can detect the motor's linear or rotational displacement. If for example, the encoder has a resolution of 360 counts per motor revolution of a rotary motor, then with each motor revolution, the sensor will provide 360 encoder signal pulses. If the pump system were designed to require one complete motor revolution to deliver the desired increment of medication, then the motor can be controlled to stop when 360 encoder counts are received. Linear displacements of linear motors may be similarly detected by suitable linear encoders or sensors.

Because motors have inertia, the power supplied to them must be removed prior to the actual stopping position in order for the motor to slow and stop. The slowing or deceleration can be accomplished in several ways including: (1) coasting which simply lets the applied and frictional torque slow the motor; or (2) dynamic braking which can be accomplished for example by shorting the motor leads or applying a potential in the opposite direction.

The applied torque affects the total rotational count. Thus as the applied torque varies, so will the error from the desired 360 counts. To account for a deviation from the target encoder count, a feedback loop is provided whereby the input power parameters to the motor, such as motor voltage or current or the time during which power is applied to the motor, may be adjusted.

In one embodiment, the motor is controlled based on the results of the previous encoder count for each cycle. Thus, for example, if 360 encoder counts were desired, but only 350 were measured, then subsequent input motor parameters can be adjusted such that the running encoder average is maintained at 360 counts. If a motor system was used with a DC motor driven with a constant current source or fixed source voltage, then the motor input parameter to be adjusted for maintaining the desired encoder count for the next pump cycle would be power on time.

For example, a motor may be driven such that half of the rotational displacement (or 180 out of 360 counts) is due to power on time and the other half is due to the coasting down of the motor under a specified nominal load (torque). Should the load increase, then the coasting would decrease thereby reducing the total encoder count measured for a constant power input. For example, the system may measure 350 counts rather than the target value of 360 counts. To maintain medication delivery accuracy therefore, the subsequent motor increment during the next pump cycle may be increased above the 180 encoder count for the power on time so that the running average is maintained at 360 for the entire pump cycle.

Yet another embodiment of the occlusion detector uses an encoder count to determine torque. In this embodiment, torque is a function of encoder count and one or more motor input power parameters. Motor load torque can be determined by evaluating the stored encoder count for a known delivered amount of energy. The detector system provides a known amount of energy (i.e., power times motor on-time), and records the motor displacement via the number of encoder counts obtained. Using a look-up table or calculated value, the system determines a corresponding torque that would result from the recorded number of encoder pulses for the amount of energy supplied.

For example, if the motor were running for a certain amount of time, this might result in an encoder count of 360. Later, the motor might run for the same amount of time under the same voltage and current conditions, but an encoder count of 350 may result. Thus the system would have encountered increased torque as reflected by the reduced encoder count. A lookup table or calculated value of torque vs. encoder count and input power parameters can thereby be developed and used to measure motor torque.

In summary, preferred embodiments disclose a method and apparatus for automatically detecting an occlusion or drive system failure in a medication infusion pump system. The electrical current to an infusion pump is measured and compared against a baseline average current. If the current exceeds a threshold amount, an alarm is triggered. Alternatively, pump motor encoder pulses are measured during a pump cycle. If the number of pulses does not correspond to a normal range, an alarm is triggered. Alternatively, a system torque value is determined from the measurement of pump motor encoder pulses during a pump cycle. If the system torque value exceeds a maximum threshold value, an alarm is triggered. In preferred embodiments, after any alarm is triggered, the pump motor is driven in reverse for an incremental distance in order to relieve the fluid pressure in the system. Alternatively, the pump motor is not reversed.

In another aspect of the present invention, the above discussed drive system allows for improved pressure sensing, occlusion detection, and other error detection systems. Relevant text from U.S. application Ser. No. 09/819,208 filed on Mar. 27, 2001, now issued as U.S. Pat. No. 6,485,465, which was incorporated by reference, describes the pressure sensing system and occlusion detection system as follows:

In preferred embodiments, a programmable controller regulates power from a power supply to a motor. The motor actuates a drive train to displace a slide coupled with a stopper inside a fluid filled reservoir. The slide forces the fluid from the reservoir, along a fluid path (including tubing and an infusion set), and into the user's body. In preferred embodiments, the pressure sensing system is used to detect occlusions in the fluid path that slow, prevent, or otherwise degrade fluid delivery from the reservoir to the user's body. In alternative embodiments, the pressure sensing system is used to detect when: the reservoir is empty, the slide is properly seated with the stopper, a fluid dose has been delivered, the infusion pump is subjected to shock or vibration, the infusion device requires maintenance, or the like. In further alternative embodiments, the reservoir may be a syringe, a vial, a cartridge, a bag, or the like.

In general, when an occlusion develops within the fluid path, the fluid pressure increases due to force applied on the fluid by the motor and drive train. As power is provided to urge the slide further into the reservoir, the fluid pressure in the reservoir grows. In fact, the load on the entire drive train increases as force is transferred from the motor to the slide, and the slide is constrained from movement by the stopper pressing against the fluid. An appropriately positioned sensor can measure variations in the force applied to one or more of the components within the drive train. The sensor provides at least three output levels so measurements can be used to detect an occlusion and warn the user.

In preferred embodiments, a sensor is a force sensitive resistor, whose resistance changes as the force applied to the sensor changes. In alternative embodiments, the sensor is a capacitive sensor, piezoresistive sensor, piezoelectric sensor, magnetic sensor, optical sensor, potentiometer, micro-machined sensor, linear transducer, encoder, strain gauge, and the like, which are capable of measuring compression, shear, tension, displacement, distance, rotation, torque, force, pressure, or the like. In preferred embodiments, the sensor is capable of providing an output signal in response to a physical parameter to be measured. And the range and resolution of the sensor output signal provides for at least three levels of output (three different states, values, quantities, signals, magnitudes, frequencies, steps, or the like) across the range of measurement. For example, the sensor might generate a low or zero value when the measured parameter is at a minimum level, a high or maximum value when the measured parameter is at a relatively high level, and a medium value between the low value and the high value when the measured parameter is between the minimum and relatively high levels. In preferred embodiments, the sensor provides more than three output levels, and provides a signal that corresponds to each change in resistance in a sampled, continuous, or near continuous manner. The sensor is distinguished from a switch, which has only two output values, and therefore can only indicate two levels of output such as, 'on' and 'off,' or 'high' and 'low.'

Preferred embodiments of the present invention employ a force sensitive resistor as the sensor, which changes resistance as the force applied to the sensor changes. The electronics system maintains a constant supply voltage across the sensor. The output signal from the sensor is a signal current that passes through a resistive material of the sensor. Since the sensor resistance varies with force, and the supply voltage across the sensor is constant, the signal current varies with force. The signal current is converted to a signal voltage by the electronics system. The signal voltage is used as a measurement of force applied to a drive train component or fluid pressure in the reservoir. In alternative embodiments, a constant supply current is used and the signal voltage across the sensor varies with force (fluid pressure). In further alternative embodiments, other electronics systems and/or other sensors are used to convert fluid pressure or forces into a measurement used by the electronics system to detect occlusions in the fluid path.

In preferred embodiments, the design and method for mounting the sensor must: sufficiently limit unintended movement of the slide with respect to the reservoir; minimize space between components; be rigid enough for the sensor to immediately detect small changes in force; avoid preloading the sensor to the point that the sensor range is insufficient for occlusion, seating, and priming detection; provide sufficient resolution for early occlusion detection; compensate for sensor system and drive train component dimensional tolerance stack-up; allow sufficient movement in components of the drive system to compensate for misalignments, eccentricities, dimensional inconsistencies, or the like; avoid adding unnecessary friction that might increase the power required to run the drive system; and protect the sensor from shock and vibration damage.

Generally, once the infusion set is primed and inserted into the user's body, the slide must not be permitted to move in or out of the reservoir unless driven by the motor. If the motor and/or drive train components are assembled in a loose configuration that allows the slide to move within the reservoir without motor actuation, then if the infusion pump is jolted or bumped, fluid could be inadvertently delivered. Consequently, the sensor and/or components associated with mounting the sensor are generally positioned snugly against the drive train component from which force is being sensed, thus preventing the drive train component from moving when the infusion pump is subjected to shock or vibration.

In preferred embodiments, the sensor is positioned so that as soon as the pump motor is loaded during operation, a drive train component applies a load to the sensor. Minimizing space between the sensor and the load-applying drive train component improves the sensor's sensitivity to load fluctuations. Small changes in load may be used to detect trends, and therefore provide an early warning that a blockage is developing before the fluid delivery is stopped entirely.

In preferred embodiments, the sensor and associated electronics are intended to measure forces between 0.5 pounds (0.23 kg) and 5.0 (2.3 kg) pounds with the desired resolution of less than or equal to 0.05 pounds. Yet, the infusion pump including the sensor should survive shock levels that result in much higher forces being applied to the sensor than the intended sensor measurement range. In alternative embodiments, the sensor range is from zero to 10 pounds (4.5 kg). In other alternative embodiments, the sensor range and/or resolution may be greater or smaller depending upon the concentration of the fluid being delivered, the diameter of the reservoir, the diameter of the fluid path, the force required to operate the drive train, the level of sensor noise, the algorithms applied to detect trends from sensor measurements, or the like.

In preferred embodiments, the sensor and associated electronics provide a relatively linear voltage output in response to forces applied to the sensor by one or more drive train components. An example of measured voltages from the sensor, (and its associated electronics) in response to forces ranging from 0.5 pounds to 4.0 pounds, are shown as data points 3201-3208 in FIG. 20.

Figure 20:
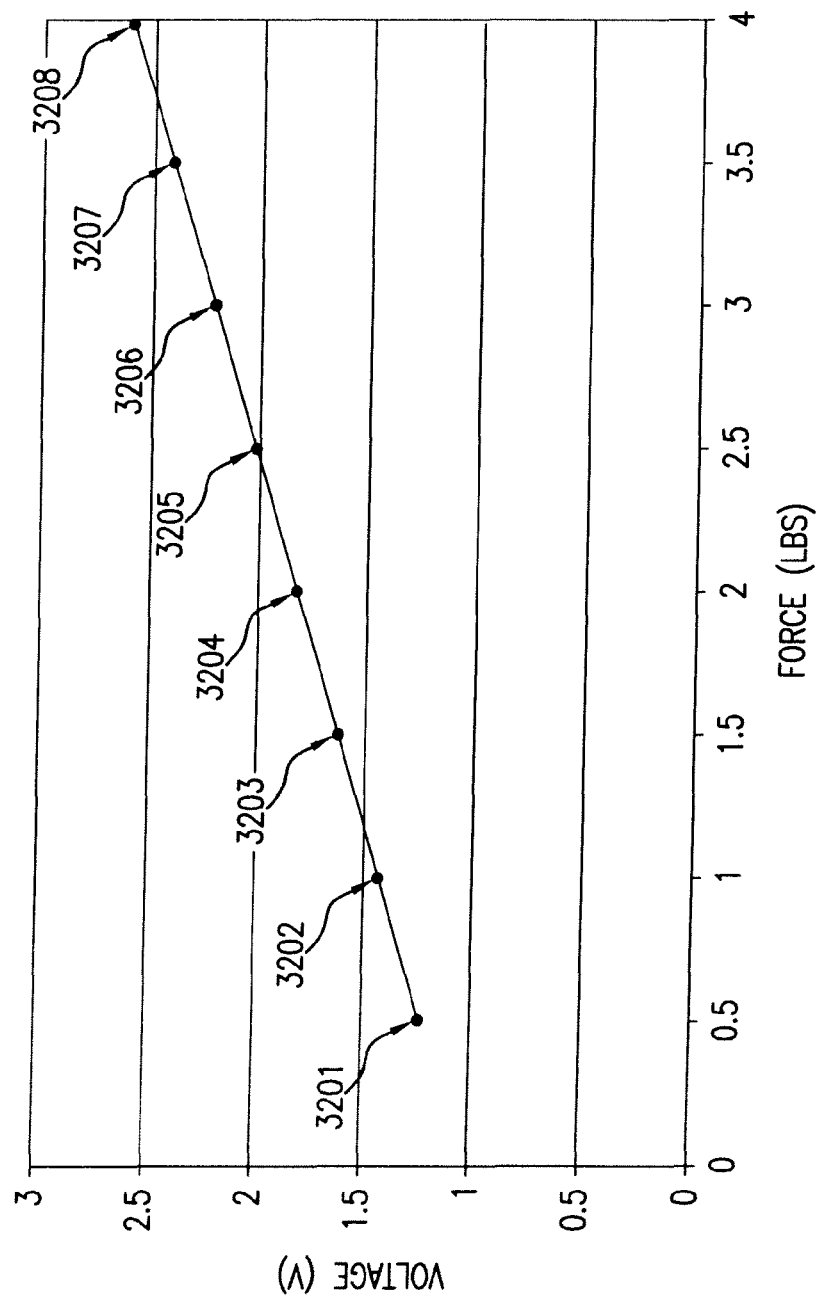
FIG. 20 is a graph showing measured voltage across a force sensitive resistor as a function of applied force.

In preferred embodiments, each sensor is calibrated by collecting calibration points throughout a specified range of known forces, such as shown in FIG. 20. A measured voltage output for each known force is stored in a calibration lookup table. Then, during pump operation, the voltage output is compared to the calibration points, and linear interpolation is used convert the voltage output to a measured force. Preferably, eight calibration points are used to create the calibration lookup table. Alternatively, more or fewer calibration points are used depending on, the sensor linearity, noise, drift rate, resolution, the required sensor accuracy, or the like. In other alternative embodiments, other calibration methods are used such as, curve fitting, a look up table without interpolation, extrapolation, single or two point calibration, or the like. In further alternative embodiments, the voltage output in response to applied forces is substantially non-linear. In further alternative embodiments, no calibrations are used.

In preferred embodiments, sensor measurements are taken just prior to commanding the drive system to deliver fluid, and soon after the drive system has stopped delivering fluid. In alternative embodiments, sensor data is collected on a continuous basis at a particular sampling rate for example 10 Hz, 3 Hz, once every 10 seconds, once a minute, once every five minutes, or the like. In further alternative embodiments, the sensor data is only collected just prior to commanding the drive system to deliver fluid. In still further alternative embodiments, sensor data is collected during fluid delivery.

In preferred embodiments, two methods are employed to declare occlusions in the fluid path, a maximum measurement threshold method, and a slope threshold method. Either method may independently declare an occlusion. If an occlusion is declared, commands for fluid delivery are stopped and the infusion pump provides a warning to the user. Warnings may include, but are not limited to, sounds, one or more synthesized voices, vibrations, displayed symbols or messages, video, lights, transmitted signals, Braille output, or the like. In response to the warnings, the user may choose to replace one or more component in the fluid path including for example the infusion set, tubing, tubing connector, reservoir, stopper, or the like. Other responses that the user might have to an occlusion warning include: running a self test of the infusion pump, recalibrating the sensor, disregarding the warning, replacing the infusion pump, sending the infusion pump in for repair, or the like. In alternative embodiments, when an occlusion is detected, attempts for fluid delivery are continued, and a warning is provided to the user or other individuals. In further preferred embodiments, a series of at least two measurements of the same variable is taken and used to determine whether there is an occlusion. An average or weighted average may be used in either the maximum measurement threshold method or the slope threshold method.

When using the maximum measurement threshold method, an occlusion is declared when the measured force exceeds a threshold. In preferred embodiments, a threshold of 2.00 pounds (0.91 kg) is compared to force values measured by the sensor before delivery of fluid. If a measured force is greater than or equal to 2.00 pounds (0.91 kg), one or more confirmation measurements are taken before fluid delivery is allowed. If four consecutive force measurements exceed 2.00 pounds (0.91 kg), an occlusion is declared. In alternative embodiments, a higher or lower threshold may be used and more or less confirmation readings may be collected before declaring an occlusion depending upon the sensor signal to noise level, the electronics signal to noise level, measurement drift, sensitivity to temperature and/or humidity, the force required to deliver fluid, the maximum allowable bolus, the sensor's susceptibility to shock and/or vibration, and the like. In further alternative embodiments, the maximum measurement threshold method is not used. In still further alternative embodiments, fluid delivery is allowed for one or more measurements that exceed a threshold, but fluid delivery is not allowed and an occlusion is declared after a predetermined number of consecutive measurements exceed the threshold.

As mentioned previously, the use of sensors, which provide a spectrum of output levels, rather than a switch, which is capable of providing only two discrete output levels, allows the use of algorithms to detect trends in the output, and thus, declare an occlusion before the maximum measurement threshold is reached. In preferred embodiments, the slope threshold method is used to evaluate trends to provide early occlusion detection. When using the slope threshold method, an occlusion is declared if a series of data points indicate that the force required for fluid delivery is increasing. A slope is calculated for a line passing through a series of consecutive data points. If the slope of the line exceeds a slope threshold, then pressure is increasing in the fluid path, and therefore, an occlusion may have developed. When nothing is blocking the fluid path, the force measured by the sensor before each delivery remains relatively constant, and the average slope is generally flat.

Figure 21:
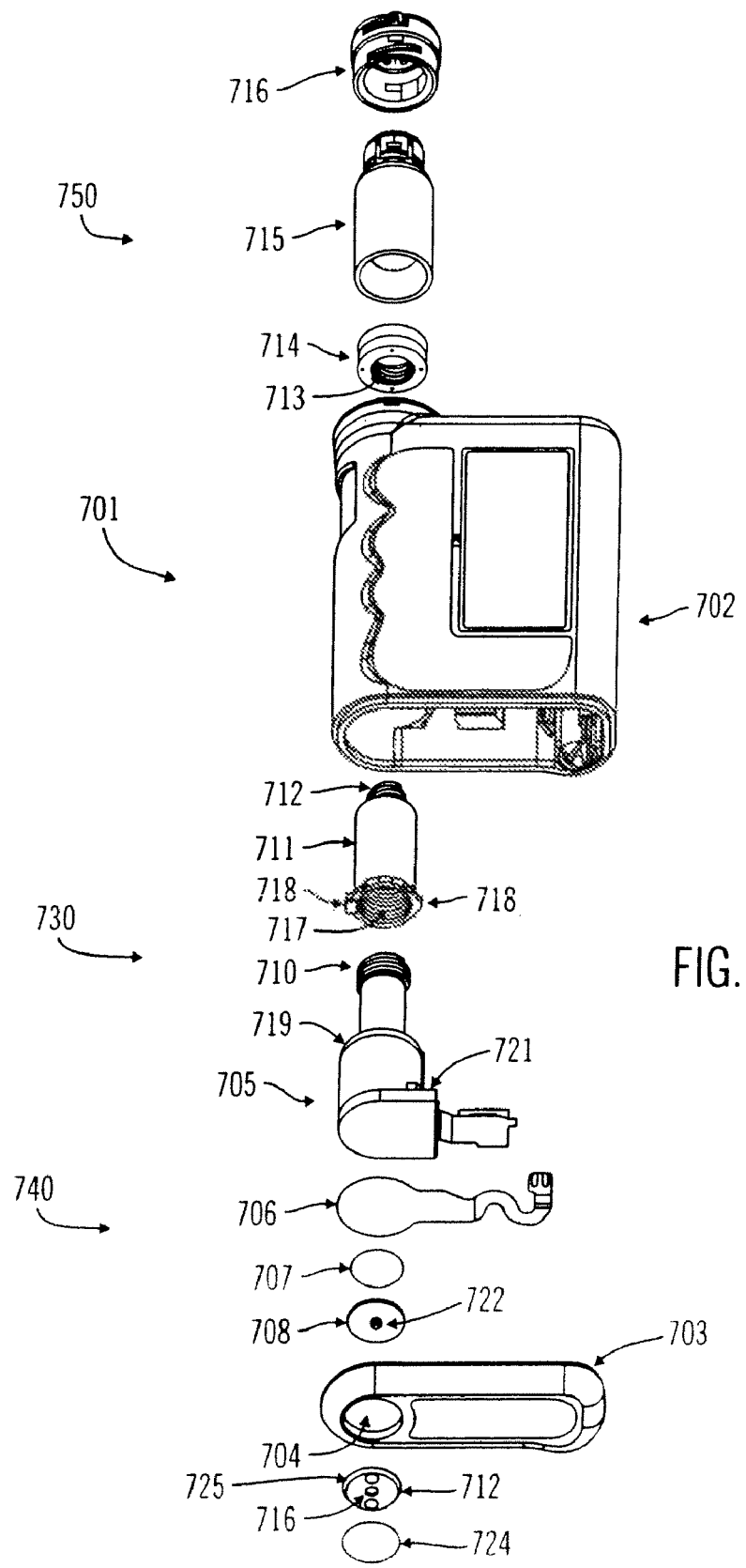
FIG. 21 is an exploded bottom/front perspective view of an infusion pump drive system, sensing system, and fluid containing assembly, incorporating a force sensor in accordance with an embodiment of the present invention.

In particular embodiments as seen in FIG. 21, a sensor 706 is used to detect when a slide 711 is properly seated with a stopper 714. The reservoir 715 containing the stopper 714 is filled with fluid before it is placed into an infusion pump 701. The stopper 714 has pliable internal threads 713 designed to grip external threads 712 on the slide 711. The stopper 714 and slide 711 do not need to rotate with respect to each other to engage the internal threads 713 with the external threads 712. In fact, in particular embodiments, the internal threads 713, and the external threads 712, have different thread pitches so that some threads cross over others when the slide 711 and stopper 714 are forced together. Once the reservoir 715 is placed into the infusion pump 701, a motor 705 is activated to move the slide 711 into the reservoir 715 to engage the stopper 714. As the threads 712 of the slide 711 first contact the threads 713 of the stopper, a sensor 706 detects an increase in force. The force continues to increase as more threads contact each other. When the slide 711 is properly seated with the stopper 714, the force measured by the sensor 706 increases to a level higher than the force needed to engage the internal threads 713 with the external threads 712. During the seating operation, if the force sensed by the sensor 706 exceeds seating threshold, the motor 705 is stopped until further commands are issued. The seating threshold is generally about 1.5 pounds (0.68 kg). In alternative embodiments higher or lower seating thresholds may be used depending on the force required to mate the slide with the stopper, the force required to force fluid from the reservoir, the speed of the motor, the sensor accuracy and resolution, or the like. In some embodiments, no force is needed to mate the slide with the stopper, because the slide only pushes on the stopper and is not gripped by the stopper.

In still other particular embodiments, other force thresholds are used for other purposes. During priming for example, a threshold of about 4 pounds (2 kg) is used. In alternative embodiments, forces greater than about 4 pounds are used to detect shock loads that may be damaging to an infusion pump.

Although the use of force sensitive resistors and capacitive sensors have been described above, it should be appreciated that the embodiments disclosed herein include any type of sensor that can provide least three different levels of output signal across the range of intended use. Sensors may be positioned within various embodiments of drive trains to measure either a force applied to a drive train component, a change in position of a drive train component, a torque applied to a drive train component, or the like.

For example, in alternative embodiments a piezoelectric sensor is used to produce varying voltages as a function of varying forces applied to a drive train component. In particular alternative embodiments, the piezoelectric sensor is made from polarized ceramic or Polyvinylidene Fluoride (PVDF) materials such as Kynar®, which are available from Amp Incorporated, Valley Forge, Pa.

The previously described embodiments generally measure fluid pressure or forces exerted in an axial direction down the drive train. Alternative embodiments of the present invention however, measure a torque applied to a drive system component as an indication of the fluid pressure within a reservoir.

Figure 22:
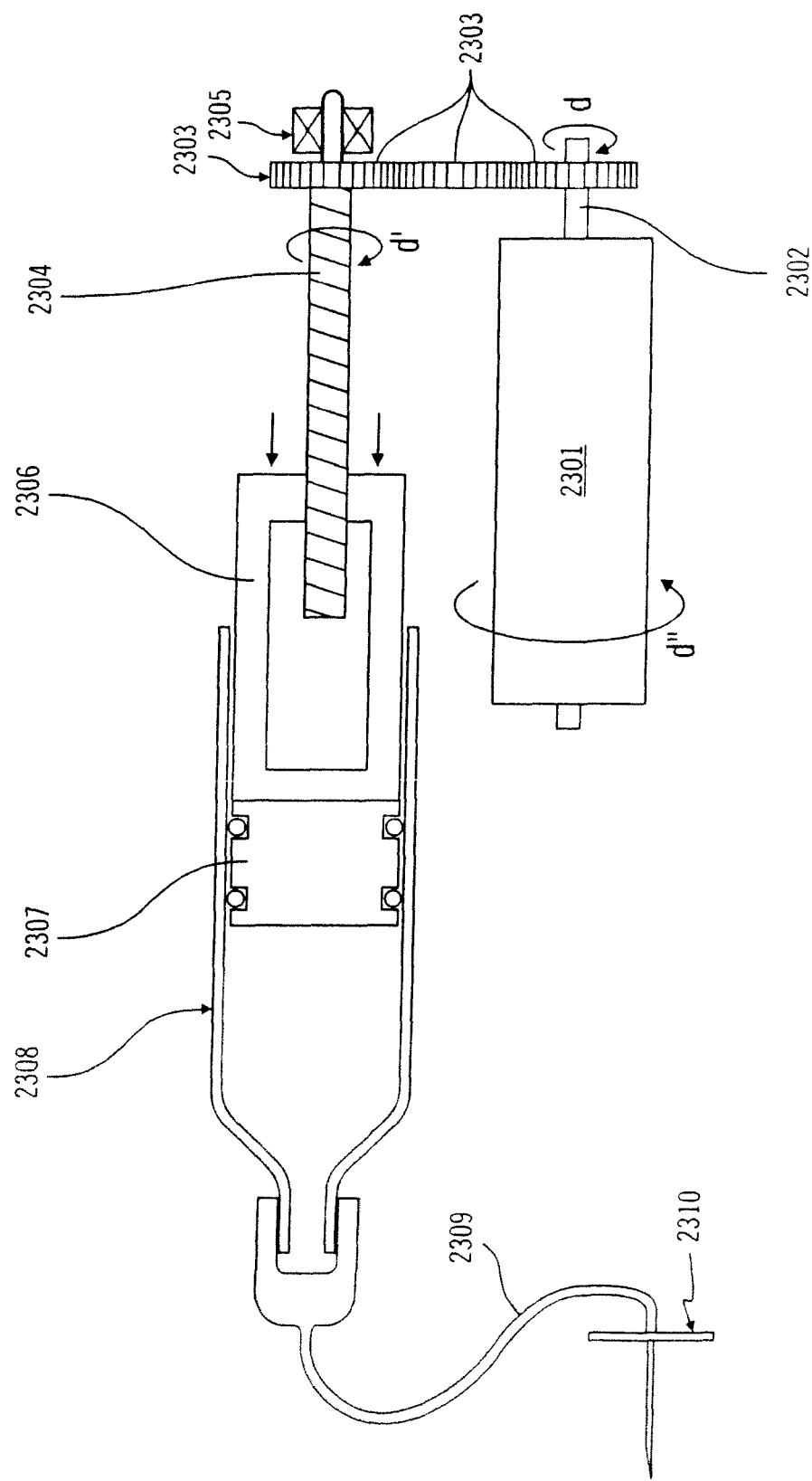
FIG. 22 is an illustration view of an infusion pump drive system with a sensor showing certain torque forces according to an embodiment of the present invention.

In other particular embodiments as seen in FIG. 22, a motor 2301 (or a motor with an attached gear box) has a drive shaft 2302 engaged to drive a set of gears 2303. The motor 2301 generates a torque powering the drive shaft 2302 in direction d. The drive shaft 2302 rotates the gears 2303 to transfer the torque to a lead screw 2304, rotating the lead screw 2304 in the direction d'. The lead screw 2304 is mounted on a bearing 2305 for support. The threads of the lead screw 2304 are engaged with threads (not shown) in a slide 2306. The slide 2306 is engaged with a slot (not shown) in the housing (not shown) to prevent the slide 2306 from rotating, but allowing it to translate along the length of the lead screw 2304. Thus, the torque d' of the lead screw 2304 is transferred to the slide 2306 causing the slide 2306 to move in an axial direction, generally parallel to the drive shaft 2302 of the motor 2301. The slide 2306 is in contact with a stopper 2307 inside a reservoir 2308. As the slide 2306 advances, the stopper 2307 is forced to travel in an axial direction inside the reservoir 2308, forcing fluid from the reservoir 2308, through tubing 2309, and into an infusion set 2310.

Should an occlusion arise, the stopper 2307 is forced to advance, and pressure in the reservoir 2308 increases. The force of the stopper 2307 pushing against the fluid results in a reaction torque d" acting on the motor 2301. In particular embodiments, sensors are used to measure the torque d" applied to the motor 2301, and the sensor measurement is used to estimate the pressure in the reservoir 2308.

In other particular embodiments as shown in FIGS. 23(a and b), a motor 2401 has a motor case 2402, a proximate bearing 2403, a distal bearing 2404, a motor shaft 2408, and a gear 2405. The motor 2401 is secured to a housing (not shown) or other fixed point by a beam 2406. One end of the beam 2406 is secured to the motor case 2402 at an anchor point 2410, and the other end of the beam 2406 is secured to the housing (not shown) at a housing anchor point 2409. A strain gauge sensor 2407 is mounted on the beam 2406.

Each end of the motor shaft 2408 is mounted on the bearings 2403 and 2404 that provide axial support but allow the motor shaft 2408 and motor 2401 to rotate. The beam 2406 supplies a counter moment in the direction d' that is equal in magnitude and opposite in direction to the motor driving torque d. As the torque produced by the motor 2401 increases, the reaction moment d" in the beam 2406 increases, thereby increasing the strain within the beam 2406 and causing the beam 2406 to deflect. The strain gauge sensor 2407 mounted on the beam 2406 is used to measure deflection of the beam 2406. The electronics system (not shown) converts the strain gauge sensor measurements to estimates of fluid pressure in a reservoir (not shown) or force acting on the drive train (not shown).

This method of measurement provides information about the pressure within the reservoir (and frictional stack-up), as well as information about the drive train. If for example, there were a failure within the drive train such as, in the gearing, bearings, or lead screw interface, the torque measured at the strain gauge sensor 2407 would detect the failure. In further embodiments, the strain gauge 2407 is used to confirm motor activation and fluid delivery. During normal fluid delivery, the measured moment increases shortly while the motor is activated, and then decreases as fluid exits the reservoir relieving pressure and therefore the moment. The electronics system is programmed to confirm that the measured moment increases during motor activation and that the moment decreases back to a resting state after the motor is no longer powered.

The above excerpts from the incorporated references (i.e. U.S. patent application Ser. No. 09/428,411, filed Oct. 28, 1999, now issued U.S. Pat. No. 6,362,591 and U.S. application Ser. No. 09/819,208 filed on Mar. 27, 2001, now issued as U.S. Pat. No. 6,485,465) described occlusion detection and fluid pressure sensing systems in ambulatory pumps using a sensor that is able to detect changes in the force required to deliver fluid from the reservoir of the infusion pump. The described circuitry detects changes in the force on the sensor, which can be used to indicate when the slide is properly seated in the reservoir or to detect when occlusions occur during the delivery of fluid from the infusion pump. The same circuitry is also described to be able to measure the current used by the drive system to deliver fluid to the user. In addition, a motor position encoder was described which can be used to detect the motor's linear or rotational displacement to assist in the occlusion detection and to measure motor torque.

According to further embodiments of the present invention, the same circuitry described above can be used to detect a failure in the force sensor by using current measurements to detect when the force sensor is malfunctioning. The force sensor a broad term that includes one or more of the sensor itself, the circuitry to interpret the data from the sensor and the physical structure to support the sensor. Any problem in the force sensor system that causes inaccurate readings from the sensor will be identified as a problem with the force sensor. Slight modifications of the circuitry in terms of increasing the gain amplifier and using a lower frequency filter to reduce high frequency noise was found effective to sample current values delivered to the motor to detect a force sensor malfunction. The force sensing system can malfunction for a variety of reasons including, but not limited to, water damage or a crack in the infusion pump casing. A critical time for detecting a force sensing system failure is during the seating of the slide with the stopper inside the reservoir (i.e., when the motor is activated for the first time after loading the reservoir within the infusion pump). As described previously, the electronics circuitry processes the sensor output levels to detect an increase in the force as the slide engages the stopper, to determine that the slide is properly seated in the stopper. However, if the force sensor system (or "force sensor" generally) is broken, then the electronics system will not detect when the slide is seated in the stopper and the slide can potentially continue to advance until it reaches end of travel and the stopper has forced virtually all fluid from the reservoir. This can have catastrophic results if the user is connected to the pump and the pump dispenses all the fluid (e.g. insulin) from the reservoir into the patient. The overdose may be enough to fatally harm or severely injure the user.

Figure 24:
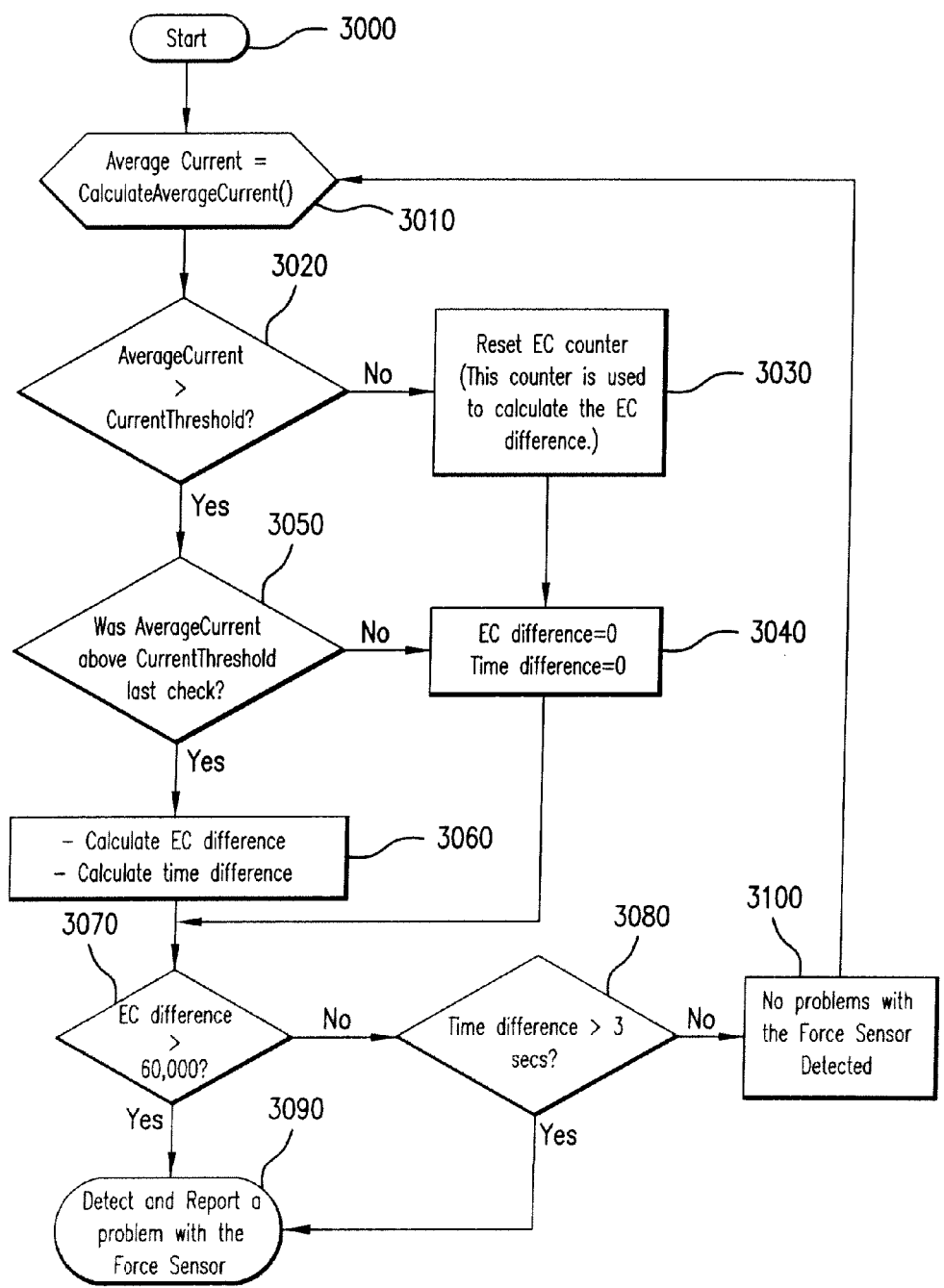
FIGS. 24 and 25 illustrate an algorithm for detecting a malfunction in a force sensor in accordance with an embodiment of the present invention.
Figure 25:
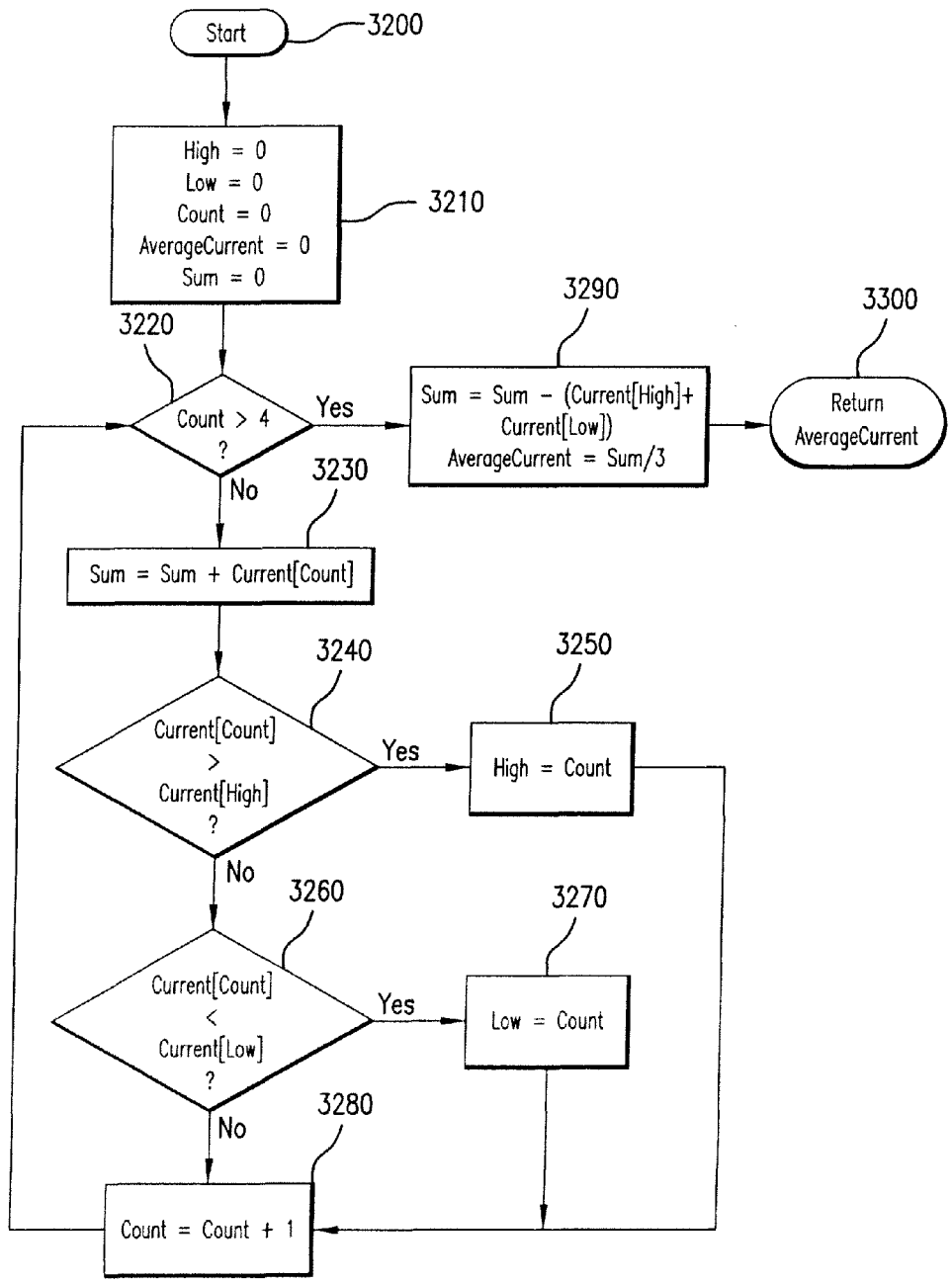

According to a preferred embodiment of the present invention, a software algorithm described in FIGS. 24 and 25 is used to detect a malfunction in the force sensor using the current measurements to drive the motor and the motor position encoder as a check for the force sensor. The software algorithms described in FIGS. 24 and 25 are run by the infusion pump controller each time the plunger slide is moved forward to seat with the stopper in the reservoir. Any time the force sensor detects an increase in force greater than a set value (i.e. detects the seating of the plunger slide in the stopper), the software algorithms of FIGS. 24 and 25 are stopped during the running of the software logic. In other words, the logic of FIGS. 24 and 25 only applies before the force sensor detects a force greater than a set threshold (i.e. never detects a seating with the stopper).

Starting at block 3000 of FIG. 24, the current used to drive the motor, the force exerted on the force sensor, and the motor position encoder counts to determine the movement of the plunger slide are measured during the seating process of the plunger slide (i.e. when the plunger slide is inserted into the stopper). At block 3010, the software calculates the average current delivered to the motor to return the value of Average Current. In preferred embodiments, a Hi-Lo Average Current (HLAC) is used. The HLAC is calculated by discarding the highest and lowest current values from the five latest values and then averaging the remaining three current values. An example of the HLAC calculation is shown in FIG. 25. However, in alternative embodiments, other methods of calculating the average current can be used including using more or less than the five latest current values and/or discarding fewer or more current values.

As seen in FIG. 25, an example of the Hi-Lo Average Current calculation starts at block 3200, when it receives a command from block 3010 of FIG. 24 to calculate the HLAC. According to preferred embodiments, the current to the drive motor is sampled until the motor is turned off. A typical sampling rate is once every 70 milliseconds. The total current that was used to run the motor is stored as a current value in a circular buffer. The current can be sampled less or more frequently. The latest five current values (i.e. Current [0], Current [1], Current [2], Current [3], and Current [4]) in the current buffer are used to determine the Average Current. At block 3210, the initial parameters used for the calculations are all set to zero except for the High and Low values, which are set to the present Current value (i.e. High=Current [present], Low=Current [present], Count=0, Average Current=0, and Sum=0).

At block 3220, the logic makes sure that five current values are available for use in the calculation (i.e. Count >4?). As stated earlier, the number of currents can be modified in alternative embodiments to be greater or less than five. Initially, there are fewer than five current values available in the circular buffer (i.e. Count ≦4), so the logic proceeds to block 3230 since the Count is not greater than four. At block 3230, all of the-current values are added together to create a Sum of the current values, with the current at the current count is added to the Sum each time the logic reaches block 3230. In the first run of the logic, the first current value (i.e. current [0]) is automatically added to the sum. The logic proceeds to block 3240 where the software identifies the highest of the latest five current values. Similarly, the logic of block 3260 identifies the lowest of the latest five current values. In the first run of the logic, the parameters Count, High, and Low were set to zero at block 3210. Thus, at block 3240, Current [0] (i.e. Current [Count]) is not greater than Current [0] (i.e. Current [High]), so the logic proceeds to block 3260. Similarly, at block 3260, Current [0] (i.e. Current [Count]) is not less than Current [0] (i.e. Current [Low]), so the logic proceeds to block 3280. At block 3280, the Count is then increased by one.

With the Count set at 1 at block 3220, the logic again proceeds to block 3230. At block 3230, the value of the Current [1] is added to the Sum at block 3230 and the logic proceeds to block 3240. At block 3240, the logic determines if Current [Count] is greater than the existing Current [High]. If Current [Count] is greater than the existing Current [High], then at block 3250, the parameter High is set equal to Count, marking that the Current [Count] is the highest current. The logic then increases the Count by 1 at block 3280 and proceeds back to block 3220. Thus, for example, if Current [1] is higher than Current [0], then the parameter High would be set to 1, marking Current [1] has the highest current received. On the other hand, if Current [Count] is lower than Current [High], then the logic proceeds to block 3260. At block 3260, the logic determines if Current [Count] is less than the existing Current [Low]. Thus if Current [Count] is less than the existing Current [Low], then at block 3270, the parameter Low is set equal to the Count, marking that the Current [Count] is the lowest current. The logic then increases the Count by 1 at block 3280 and proceeds back to block 3220. Thus, for example, if Current [1] is lower than Current [0], then the parameter Low would be set to 1, marking Current [1] as the lowest current received. Future iterations of the logic of blocks 3240, 3250, 3260 and 3270 will identify the high and low currents out of the five currents used to calculate the Average Current.

Once five currents are measured and compared to determine the high and the low currents, the logic of 3220 will then calculate the Average Current at block 3290. At block 3290, the Sum, which has added all of the five current values together, will subtract the Current [High] and Current [Low] and divide the remaining sum by 3. At block 3300, the Average Current Calculation will be returned to block 3010 of FIG. 24 and used as the Average Current in the logic of FIG. 24.

Referring back to FIG. 24, the Average Current is compared with the Current Threshold at block 3020. A value of the Average Current greater than the Current Threshold triggers the broken force sensor software algorithm. The Current Threshold is a unique value initially can be assigned to each insulin pump based on pre-testing of the pump before the insulin pump is issued to a user. It is also possible that there is a threshold set for all devices that does not require any testing of the individual device to determine. The Current Threshold is used to indicate the current used when the plunger slide seats within the reservoir. Each insulin pump will have slightly different values because the raw material used within the insulin pump will have slightly different physical characteristics resulting in differing Current Threshold values. In preferred embodiments, the following test is performed to derive the Current Threshold to ensure the software algorithm will function properly. The test applies a constant 31b force to the pump slide as the pump performs a seating, where both force and current are measured. The current values will be processed using a Hi-Lo Average Current algorithm like the one discussed earlier and will have the first and last 20 measurements thrown out. In alternative embodiments, a larger or smaller number of first and last measurements may be thrown out. These samples are thrown out to account for the system not coming to steady state for the first samples and slowing down for the last samples, making the current and force values not constant. The current values will be sampled at the same rate as it is in the application code (e.g. every 70-90 milliseconds). These values will then be averaged and stored for application code. The force measurements will also be measured and averaged, but without removing data or using the Hi-Lo averaging. The Average Force will be compared to 3 lbs and if it is not within 2.4 and 3.6 lbs an error will be flagged and the pump will state that the force calibration was not accurate. Alternatively, the Average Force can be compared to a larger or smaller force than 3 lbs, and the tolerances can be ranged from greater or less than 0.6 lbs from the force to which the Average Force is compared. If this occurs, the Current Threshold value is considered invalid and is not stored and the pump is rejected. If there is no error with the force value, both the Current Threshold and the Average Force is stored in the pump. In still further embodiments, the values of the Current Threshold and the Average Force can also be displayed after the test is complete using the user's actuation keys. Moreover in still further embodiments, the user using the same test programmed within the insulin pump can periodically recalibrate the Current Threshold.

Returning to block 3020 of FIG. 24, if the Average Current is not greater than the Current Threshold, the logic identifies that the slide has not been seated in the reservoir yet and proceeds to block 3030. At block 3030, the Encoder Count (EC) is reset. The Encoder Count is the count recorded by the motor position encoder to measure the movement of the slide. In preferred embodiments the encoder can record the rotations of the motor and the lead screw. For example, in preferred embodiments, there are 256 counts per revolution of a DC motor and approximately 221 revolutions of the motor per lead screw revolution. In the algorithm of FIG. 24, the Encoder Count is based on the number of revolutions of the DC motor times the number of revolutions of the lead screw. However, in other embodiments, the encoder can count only the revolutions of the motor, and the number of counts per revolution can vary based on the infusion pump mechanism or method of counting. In further embodiments, the use of an Encoder Count may be omitted from the software calculations.

Once the Encoder Count is reset, the logic proceeds to block 3040. At block 3040, the parameters, Encoder Count Difference and Time Difference, are set to zero. The Encoder Count Difference and Time Difference are set to zero to indicate that the plunger slide has not yet engaged the reservoir during seating, and the logic is set to repeat back to block 3010. Specifically, when the logic proceeds to block 3070, the Encoder Count Difference is compared to see if it is greater than the Encoder Count Threshold. In the preferred embodiment the Encoder Count Threshold is set at 60,000. 60,000 is the approximate value of the count if 10 units of RU-100 insulin is expelled from the reservoir once the plunger slide is seated in the reservoir. In alternative embodiments, the Encoder Count Threshold level can be set at different levels, especially with the use of different types of insulin, medications, fluids, or drug. However, in this case, where the Encoder Count Difference is set to zero, the logic proceeds to block 3080 since the Encoder Count Difference is less than the Encoder Count Threshold. At block 3080, the Time Difference is compared to the Time Threshold. In the preferred embodiments, the Time Threshold is set at 3 seconds. The Time Threshold is a backup to the Encoder Count Threshold to estimate the amount of advancement of the plunger slide based on the time the motor was actuated. In this case, the Time Difference is set to zero, and thus, the logic proceeds to block 3100 to indicate that no errors with the force sensor were detected. From block 3100, the logic loops back to block 3010 to determine the latest Average Current.

Once the Average Current exceeds the Current Threshold at block 3020, the logic recognizes that the seating of the plunger slide in the reservoir has occurred. The logic proceeds to block 3050 to determine if the Average Current was above the Current Threshold last check. The logic of block 3050 uses the current to determine whether the seating of the plunger slide has just occurred or whether the plunger slide has already been seated. If the plunger slide has just been seated (i.e. this was the first time the Average Current was above the Current Threshold at block 3050), the logic proceeds to block 3040 where the parameters EC difference and Time Difference are set to zero. The logic then loops back to block 3010 as discussed above without indicating any errors with the force sensor. On the other hand, if the logic of block 3050 determines that the seating has already occurred previously, the logic proceeds to block 3060.

At block 3060, the parameters Encoder Count Difference and Time Difference are calculated. The Encoder Count Difference determines the number of additional encoder counts since the pump first detected seating of the plunger slide (i.e. the number of encoder counts since the Average Current has risen above the Current Threshold and stays above the Current Threshold). In addition, the Time Difference determines the amount of time that has passed since the pump first detected seating of the plunger slide (i.e. the time since the Average Current has risen above the Current Threshold and stays above the Current Threshold). The calculated parameters are then compared to the Encoder Count Threshold in block 3070 and the Time Difference Threshold in block 3080. If either the Encoder Count Threshold in block 3070 or the Time Difference Threshold in block 3080 is exceeded, a failure with the force sensor is detected and reported at block 3090. Of course, as mentioned above, if the force sensor detects an increase in force any time during the algorithm of FIG. 24 that signals the proper seating of the plunger slide in the reservoir, no error will be detected for the force sensor.

Therefore, the software algorithm of FIG. 24 is designed to determine an error with the force sensor when it does not report an increase in force (i.e. a force greater than the Low Force Value preset in each infusion pump to indicate seating of the plunger slide) even though the current use would indicate that a higher force should be detected. Therefore the following two scenarios will occur with the existing algorithm. The first is the case of a good sensor when during seating the force rises above 1.4 lbs on the force sensor while the Average Current remained below the Current Threshold before the seating occurred, or the current is above the Average Current but not for the required number of encoder counts before the force of 1.4 lbs is reached. In this first case, the pump seats the plunger slide in the reservoir and flags no errors. In the second case, during seating of the plunger slide, the Average Current reaches the Current Threshold and remains above the Current Threshold while the force is never greater than Low Force Value before the specified number of Encoder Counts is reached. In this case, the force sensor is detected as having failed once the pump reaches the specified number of Encoder Counts.

In alternative embodiments, the algorithm of FIG. 24 can be modified to detect when the sensor performance is starting to fail (i.e. a marginal sensor) such that the force reading increases above the Low Force Value, but does not increase above a Force Threshold (i.e. a value preset with the infusion pump to indicate a seating of the plunger slide in the reservoir) to clearly indicate that the seating has occurred. Another alternative embodiment may modify the algorithm to account for cases where during seating the Average Current reaches its threshold but then drops back down below the threshold. Each time the Average Current drops below the threshold the Encoder Count threshold is restarted. However if this happens three or more times, on the third occurrence, the Encoder Count threshold should not be re-set and the pump should continue to seat only for the specified Encoder Count threshold. These software algorithms may also take into account the users ability to start and stop seating of the plunger slide at will so that even if they stop and then restart the seating process as long as there is no rewind, the pump will recognize if the threshold has been reached three times.

In further embodiments, the infusion pump also performs a data storage function to record data surrounding the various step-by-step functions of the infusion pump. Thus, upon each instance of seating, the data storage function records the values of force and current detected and stores that information into the long-term trace buffer. In addition, if the Current Average ever reaches the Current Threshold, each subsequent measurement of force and current should also be stored in the long-term trace buffer until the pump seats or flags an error. Moreover, every time the current threshold is passed and the alarm is flagged, end of vial reached, force threshold passed, or the pump seats the plunger slide in the reservoir, these data points are recorded and a trace can be produced from the collected data points to analyze the data.

In further embodiments, multiple variables are used to detect an occlusion or obstruction. By using two or more variables, the system avoids any problems that may occur from using one variable alone. For example, if force alone is used to detect occlusions, a broken force sensor could cause false occlusions to be detected or actual occlusions to be missed. This could result in missed doses or excessively large amounts of medication to be delivered to a patient. The same potential problems can occur by using any one parameter as the basis of occlusion detection of the system.

Using two or more variables to determine an occlusion can shorten the time to recognize an occlusion and/or increase the accuracy of occlusion detection. It is preferable to have a system that minimizes the number of false alarms but also decreases the time to indicate an occlusion. By decreasing the time to indicate an occlusion, it is possible to reduce the number of missed doses.

There are many variables that can be used in a multi-variable occlusion detection approach. Examples of such variables are properties and/or parameters of the system, pump and/or motor, such as pressure, delivery volume, force, drive current, drive voltage, drive time of the motor, coast time of the motor, energy of the delivery pulse, and variables from the closed loop delivery algorithm, such as drive count, coast count, and delta encoder count. All of these variables are possible to be measured from the circuitry described above, however it is also possible to add circuitry to measure any of these or additional variables if desired.

Force is generally measured from a force sensor, which is described in embodiments above. Also described in embodiments above is the drive current of the motor, which is the amount of current applied to the motor and can be measured from the force sensitive resistor. Drive voltage is the measure of voltage applied to the motor and can also be measured from the force sensitive resistor, which for example measures the voltage across the motor windings. Drive time of the motor is time, for example in seconds or milliseconds, for which the motor is powered on (i.e., power is supplied to the motor). Coast time of the motor is the time, for example in seconds or milliseconds, that the motor continues to coast or move after the motor was powered off until the end of the delivery pulse. The energy of the delivery pulse is a product of drive voltage and drive current, which may be calculated by a computing device.

Drive count and coast count are each encoder counts, which are discussed above. Drive count increases as the time that the motor is powered on increases, and coast count increases as the time that the motor is coasting after the motor is powered off increases. Drive count and coast count together are equal to the delta encoder count, or change in the encoder count from a delivery pulse.

Two or more of the variables described above can be combined in many different ways. For example, they may be multiplied together or added together. If more than two variables are used, some of the variables may be added in conjunction with multiplication of other variables. For example, one or more variables may be multiplied by a weighting coefficient before summing them. The rate of change of one or more variables may be increased by putting the magnitude of the variable to a power. For example, if F=measured force, it would be possible to increase the magnitude of measured force by $F^X$, where X=a desired power. Putting magnitudes of variables to powers may be used in conjunction with multiplying and/or adding variables together.

When combining the variables, it may also be useful to filter the data by using averaged values or by using averaged values taken after excluding high and low readings. For example, if one data point is far outside the range of average data points taken nearby, it may be useful to discard that data point. Additional examples of filtering data that may be used are clipping data at a maximum or minimum value, limiting rate of change between values, and calculating trend and, if the trend is consistent, using fewer values.

Normalization factors can also be used to set the magnitude of different variables to similar levels, so that they can be used in conjunction with each other. For example, in one embodiment, the non-occluded running force is about 0.5 pounds, the occluded force is about 2.0 pounds, the non-occluded drive count is approximately 47, and the occluded drive count is approximately 100. These values can be determined for an individual pump based on pre-testing of the pump before issuance to a user, or average values for certain pump configurations can be determined. Further, it is possible to vary the dependency of the occlusion detection on each variable. For example, it may be desirable to have occlusion detection depend equally on force and on current. However, it may be desirable to have occlusion detection depend more on force in those instances where force is a better indicator of occlusion.

In one embodiment of a multi-variable occlusion detection approach, the variables drive count and force are both used to detect occlusions. While the pressure increases from an occlusion, the force required to move the slide forward increases. The increased pressure results in an increased force reading by the force sensor. The increased force also results in an increased drive count necessary to reach the target encoder count for each delivery pulse. Multiplying drive count and force or adding these variables increases the magnitude of occlusion indication.

Figure 26:
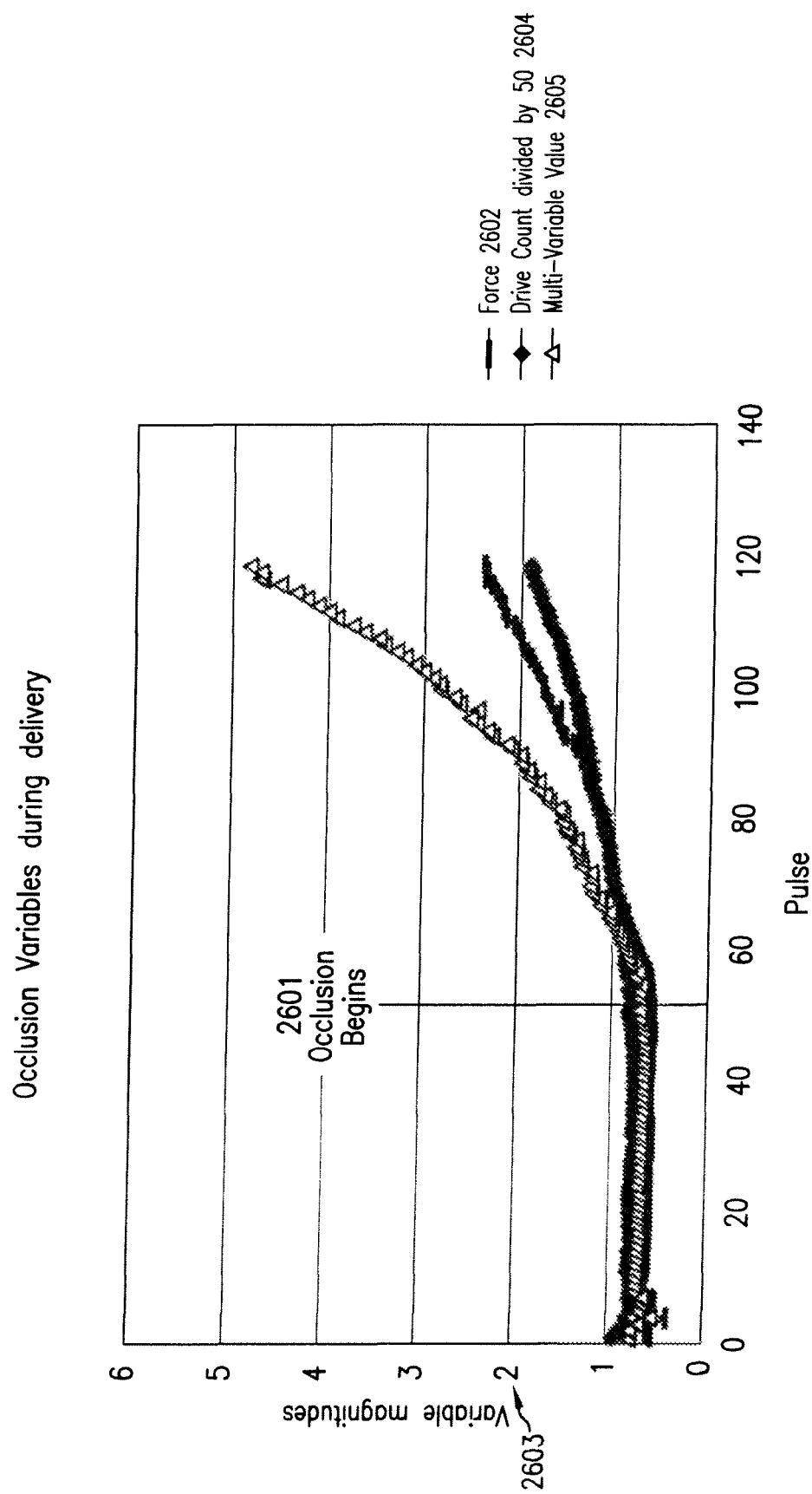
FIG. 26 is a graph showing measured force, drive count divided by 50 and multi-variable value of an embodiment of the invention shown as a function of delivery pulse.

FIG. 26 shows a graph illustrating the difference in magnitude between a single variable versus multi-variable occlusion detection approach. An occlusion 2601 begins between 40 and 60 delivery pulses. The graph shows data for two different approaches based on a single variable. The first series of data 2602 is based on the single variable—force, which is measured by the force sensor. For this single variable approach based on force, the occlusion was identified using a maximum threshold method at two variable magnitudes 2603. The second series of data 2604 is also based on a single variable—the drive count divided by a normalization factor of fifty. The third series of data 2605 is based on both of these variables—force and normalized drive count, which are multiplied together and then an offset is added to the product of the two variables. The equation used to create this particular series of data points, if F=measured force and DC=drive count, was Multi-Variable Value=(F*(DC/50))+0.25. In this equation, the normalization factor was 50 and the offset was 0.25. The normalization factor or offset may be any preferred values identified as useful for detecting occlusions with good accuracy.

The graph shows that before the occlusion 2601, the magnitude of the multi-variable value series 2605 is similar to that of the single-variable force reading 2602. This is a result of the normalization and offset of the equation. As the pump continues to deliver insulin after the occlusion begins 2601, the multi-variable value series 2605 reaches magnitudes of almost twice that of the single variable force reading 2602. Thus an occlusion could be identified much sooner in the multi-variable approach. With the multi-variable approach, the threshold for declaring an occlusion could also be raised without increasing the amount of time elapsed before an occlusion is detected, which could provide higher confidence that an occlusion had in fact occurred.

The multi-variable approach can be incorporated into algorithms used for single variable occlusion detection. Also, new algorithms can be created specifically for use with the multi-variable occlusion detection. Some algorithms that can be used, by way of example, are slope threshold and maximum threshold methods. Alternatively, variance in variables may be monitored by looking for values that are outside the general range of values for the system. If a value is more than a certain variance from the usual range of values, it may indicate an occlusion or other problem has occurred in the system.

Figure 27:
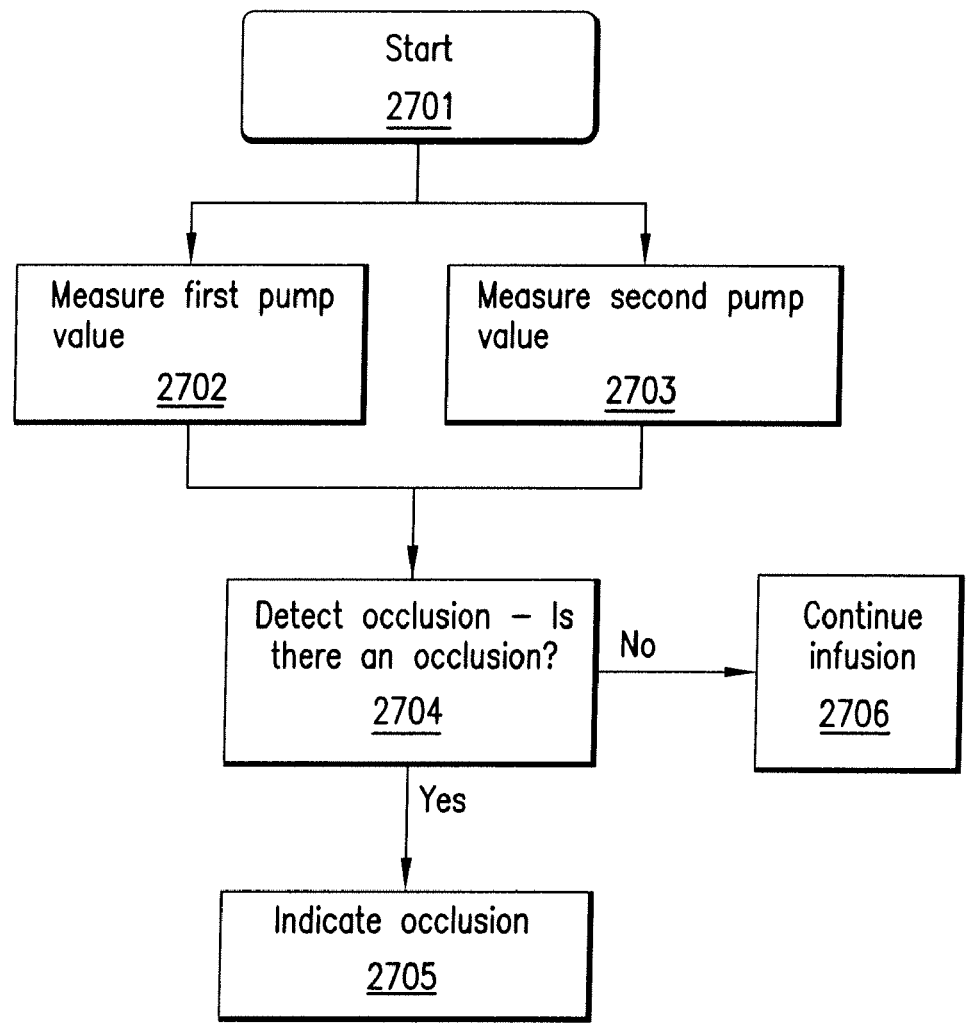
FIG. 27 illustrates an algorithm for detecting an occlusion in accordance with an embodiment of the present invention.

FIG. 27 illustrates a flow chart of the logic of embodiments using the multi-variable approach. The logic starts at 2701.

The system measures a first pump value at 2702 and a second pump value at 2703. These blocks may occur in series or in parallel. If they occur in series, the values may be measured at the same time or at different times, but it is preferred that they are measured during the same delivery pulse. The system then detects occlusions based on the measured pump values 2704. Occlusions may be detected as described above and by using the dynamic system described below. If there are no occlusions, the system continues with infusion 2706 as normal. If there is an occlusion detected, the system indicates an occlusion 2705. The system may set off an alarm to indicate the occlusion to the user.

Figure 30:
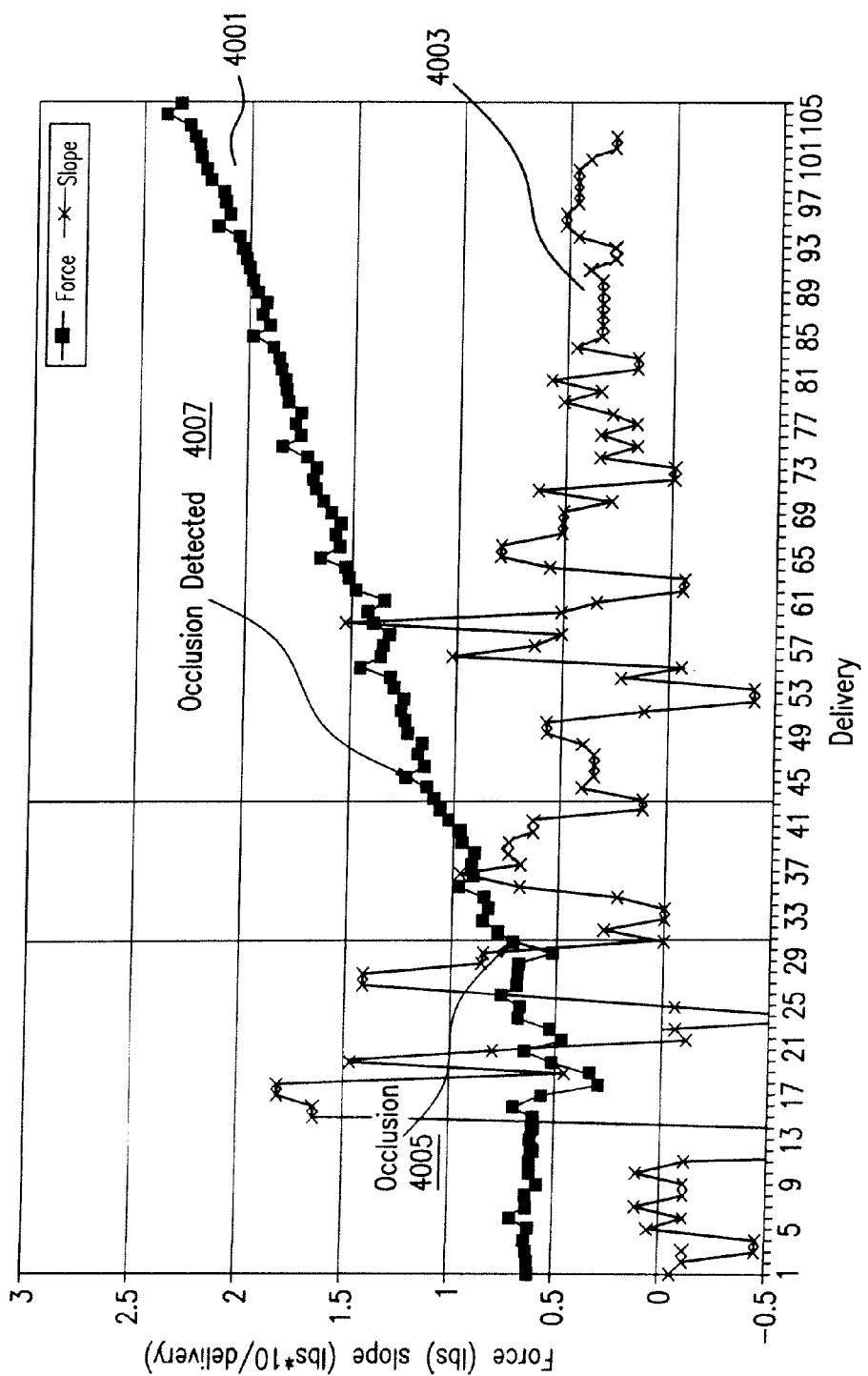
FIG. 30 is a graph showing force and slope versus delivery in an embodiment of the present invention.

Slope of one or multiple variables can be used to accelerate the detection of an occlusion as well. This is the rate of change of either one or multiple variables. During normal delivery the slope should be constant without a regular rate of change. After an occlusion has occurred, for example the force or drive count, would increase as the pressure increases. There can be lots of small changes to these variables during normal delivery, but after an occlusion the rate of change would remain fairly steady and positive. In a preferred embodiment the rate of change of the force would be positive for 10 deliveries consecutively then an occlusion would be identified. It can also be set with a threshold to verify the system is running high. The rate of change would need to be positive for 10 consecutive deliveries and the force must be greater than 1 lbs. A graph of force measurements 4001 taken during delivery is shown in FIG. 30. The line formed from points 4003 shows the slope of the force. In the example shown in FIG. 30, an occlusion occurs at 4005. After 10 consecutive positive slope values, the system is programmed to detect the occlusion 4007 and an alarm is triggered.

Figure 31:
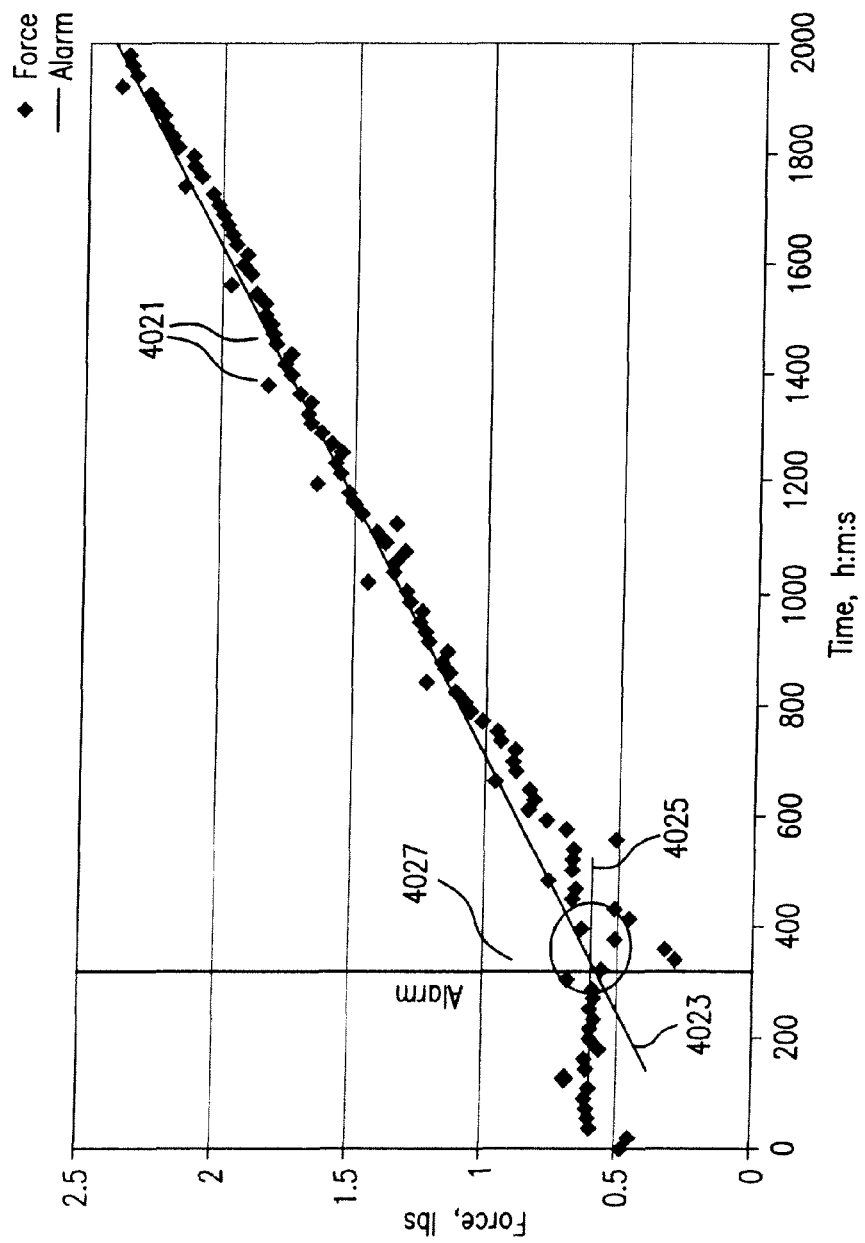
FIG. 31 is a graph showing force versus time in an embodiment of the present invention.

Another approach to determining an occlusion is looking for a point of inflection or the rate of change of the slope. This can be the change from constant force or other variable to a new rate of change. For example, FIG. 31 shows force measurements 4021 taken over time. The constant force shown by line 4023 changes to a new rate of change shown by line 4025. An alarm 4027 is triggered by this change.

In further embodiments of the invention, occlusion detection, either through use of one variable or multiple variables, is performed dynamically. There are many variables in the systems described above that cause variance in the variables mentioned for a delivery pulse. Some of these are a result of misalignment between the reservoir and the drive train, misalignment between the plunger or stopper and the drive train, compliance of the o-rings, and noise associated with the sensor. Due to these variables, the occlusion detection thresholds are set to compensate for these to assure a false detection of occlusions does not occur. As a result, these systems generally allow more delivery pulses before an occlusion is detected. For example, a maximum threshold detection method using force readings may allow sixty additional delivery pulses to be attempted after an occlusion occurs before the system alarm is activated. If a dynamic occlusion detection method is used, the number of excess delivery pulses can be reduced to a very small number, as low as three additional pulses.

In the occlusion detection methods described earlier in this description, only one measurement is generally taken per delivery pulse. This measurement may occur before, during, or after delivery. A dynamic method for occlusion detection takes multiple measurements collected during each delivery pulse. The measurements may be taken periodically at a pre-determined frequency, as often or as infrequently as desired, or measurements may be taken at particular times with respect to the delivery pulse. For example, measurements could be taken every few seconds or even once every second or partial second. It is also possible to take continuous measurements throughout the delivery pulse, for example, once every 10 seconds, once a minute, once every five minutes, or the like.

Figure 28:
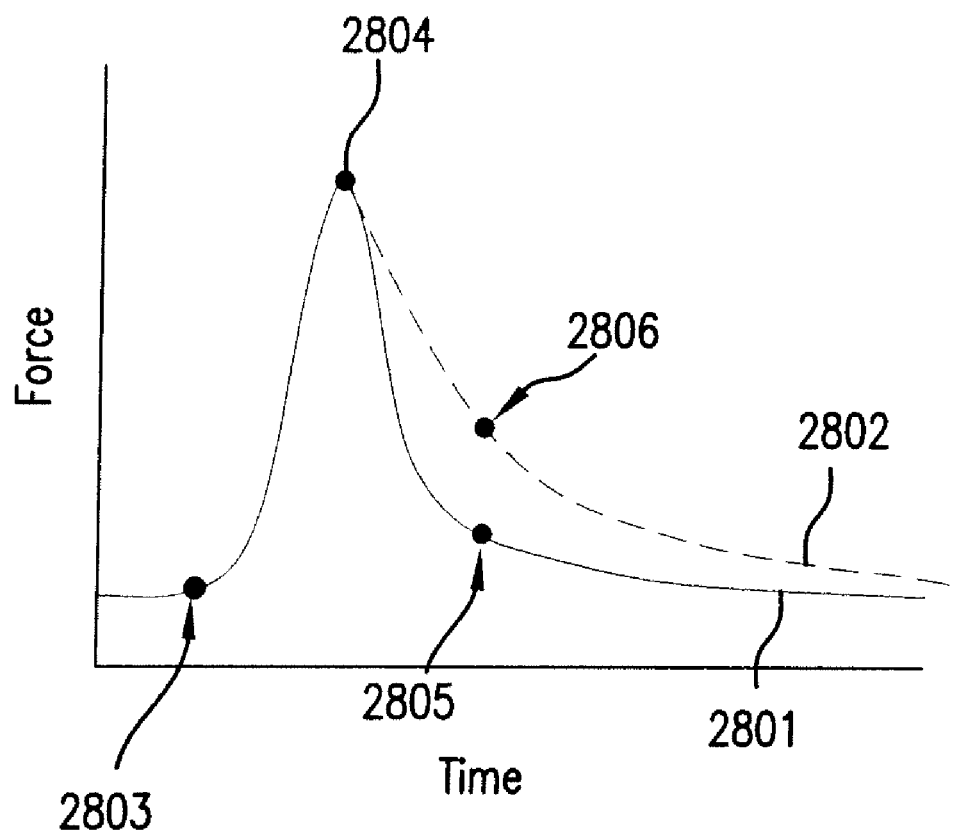
FIG. 28 is a graph showing measured force across time for a single delivery pulse in an embodiment of the present invention.

Using measurement of force as an example, generally the force increases a large amount right after a delivery pulse. After the delivery pulse, the force decreases until a steady state force is achieved. If there is an occlusion, the steady state force will be higher than if there is no occlusion, or when there is an occlusion, the steady state force will be a larger percentage of the peak force than when there is no occlusion, or if there is an occlusion the force at some time after the peak force is a larger percentage compared to the peak force than if there is no occlusion. An illustration of this is shown in FIG. 28. The graph in FIG. 28 shows force as a function of time during a delivery pulse. The bold line 2801 shows force in a non-occluded system. The dashed line 2802 shows force in an occluded system. Because the system is occluded, force decreases at a less rapid rate. Using the multiple measurements taken during delivery, it is possible to determine a peak value 2804 of the measurement. As will be further discussed below, the graph also shows an occluded system post peak value 2806 and a non-occluded system post peak value 2805. A pre-peak value 2803 is also shown.

It is possible to detect occlusions dynamically using the above principles in a number of ways using many types of variables or parameters. Although the following analysis describes using force measurement, it should be understood that the dynamic detection of occlusions may be similarly detected using any of the variables described above, including multiple-variables.

A simple algorithm can use two measurements or data points. For example, force may be measured at the peak value 2804 and at some time after the peak value 2805 or 2806. In this algorithm, the difference between the peak 2804 and post-peak values 2805 or 2806 is calculated and then compared to a difference threshold. The difference threshold may be predetermined for all pumps, determined for an individual pump based on pre-testing of the pump before issuance to a user, determined for a pump each time a new reservoir is loaded into the pump and the pump is primed (for example, the system may calculate the average difference of the first three delivery pulses after priming the pump, and use a percentage of that average difference as the difference threshold), or continually determined (for example, the system may take the average difference of a certain number of consecutive delivery pulses calculated from several pulses ago, for example, the average difference of three consecutive delivery pulses may be calculated for six pulses prior to the current delivery pulse, and use that average difference as the difference threshold). If the difference meets or exceeds that threshold, an alarm is activated. Thus, variability in the non-occluded force will not trigger an occlusion alarm. For example some variables that may cause the unoccluded force to vary include: misalignment between the plunger and the reservoir, inconsistencies in the reservoir interior profile, varying friction between the stopper and the reservoir, faster or slower delivery rates, larger or smaller delivery quantities, etc.

Alternatively, if the difference meets or exceeds a certain percentage of the threshold, for example, 90% of the threshold value, an alarm could be activated. It is also possible to keep a record of all differences or a certain number of past differences. The system may wait until a certain number of consecutive pulses, for example three, create differences that are equal or higher to the threshold value (or a percentage of the threshold value) and then activate an alarm. Additionally, to account for variables in the system, the average difference over a certain number of consecutive pulses, for example three, may be taken and compared to the difference threshold. If the average difference is equal to or higher than the difference threshold (or a percentage of the threshold), then an alarm is activated.

Further, to account for changes in the peak over each pulse, it is possible to calculate the total force as the difference between the peak value 2804 and a predetermined steady state value, and then to calculate the difference between the peak 2804 and post-peak 2805 values as a percentage value of the total force. If this percentage is below a predetermined threshold, then an alarm is activated. However, the drawback of this method is that it assumes the force returns to the similar or identical steady state value after each pulse.

Accordingly, to account for the fact that the force never returns to zero and may not return to the identical or similar steady state value, also shown in FIG. 28 is a third value 2803, which is taken before the peak value. The third value 2803 may be used in addition to the peak 2804 and post-peak 2805 values. This pre-peak value 2803 can be used to normalize the peak value 2804. The difference between the peak value 2804 and pre-peak value 2803 can be calculated as a total force value. Then, the difference between the peak value 2804 and post-peak value 2805 or 2806 would be measured as a percentage of the total force value just determined. If this percentage is below a predetermined threshold, then an alarm is activated.

Also, it is possible to calculate the rate of decay of the variable (e.g., force) when decay begins after the peak value 2804. Because the rate of decay is the same immediately after the peak 2804 and near the end of decay, it is preferable to take measurements starting at some predetermined time period after the peak 2804 and ending some predetermined time period before the end of the decay. The slope may then be calculated for a line passing through the series of measurements and compared to a slope threshold. Similar to the difference threshold described above, the slope threshold may be predetermined for all pumps, determined for an individual pump based on pre-testing of the pump before issuance to a user, determined for a pump each time a new reservoir is loaded into the pump and the pump is primed, or continually determined. If the slope of the line is equal to or greater than the slope threshold, then an alarm is activated. Alternatively, if the slope meets or exceeds a certain percentage of the slope threshold, for example 90% of the threshold, then an alarm can be activated. It is also possible to calculate average slope values and to compare the calculated average slope to the slope threshold (or a certain percentage of the threshold), as discussed above with respect to the other dynamic occlusion detection systems. If the average slope value is greater than or equal to the slope threshold, or some other predetermined percentage (e.g., 90%), of the slope threshold, the force can be considered to not be decaying normally. Therefore, an occlusion can be declared.

In further embodiments, multiple measurements of a variable (e.g., force) may be taken during each delivery pulse as described above, and a curve may be fit into the measurements or data points. Then an integral can be taken of the area beneath the curve. If the integral is above a certain threshold, an occlusion can be declared. In still further alternative embodiments, other algorithms may be employed to determine whether an occlusion has occurred by using the above variables, such as using differential values rather than actual measured values, calculating the derivative of measured values, using a subset of points across the range of points to calculate the slope, using curve fitting equations, employing smoothing, clipping or other filtering techniques, or the like.

Because there is a higher likelihood of failure, such as missed detection of an occlusion, at high flow rates (e.g., a high number of delivery pulses in a short period of time, such as for a bolus delivery), it may be preferable to use other occlusion detection methods at these high flow rates. This failure may occur, because at high flow rates there may not be enough time between pulses for the system to return to a steady state. The dynamic occlusion method may be used in conjunction with the other occlusion detection methods described above (e.g., maximum measurement threshold, slope threshold, or the like) to allow for improved occlusion detection at all times.

Figure 29:
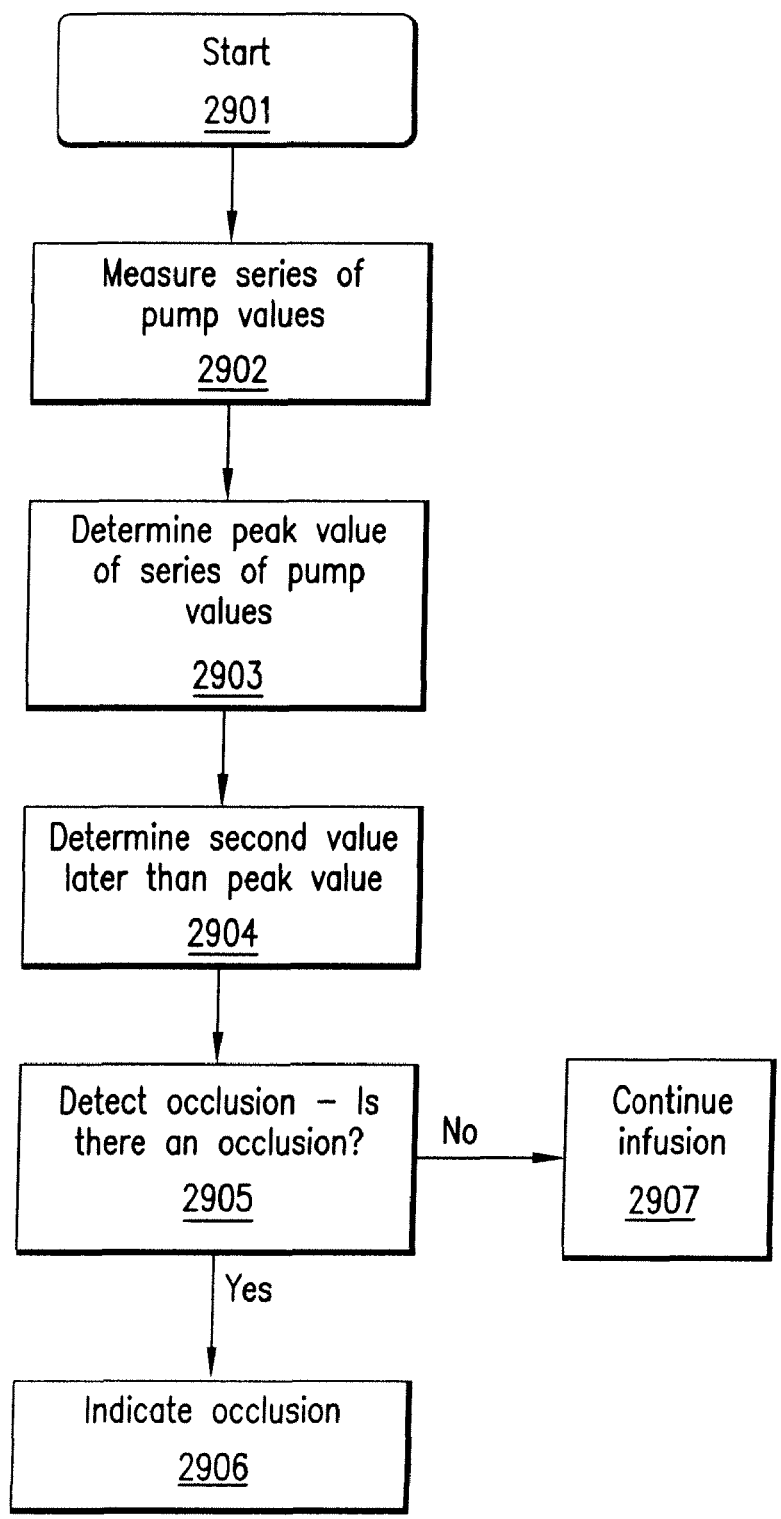
FIG. 29 illustrates an algorithm for detecting an occlusion in accordance with an embodiment of the present invention.

FIG. 29 illustrates a flow chart of the logic of embodiments using a dynamic occlusion detection approach. The logic starts at 2901. The system measures a series of pump values at 2902, preferably periodically over one delivery pulse. The system determines the peak value of the series of pump values at 2903. The system also determines a second value later than the peak value at 2904. The second value may be at a predetermined time after the peak or a predetermined number of measurements taken after the peak value. Alternatively, it may also be a predetermined time or number of measurements taken before the next delivery pulse or taken after the delivery pulse starts. The system then detects occlusions 2905. Occlusions may be detected by using the algorithms described above. If there are no occlusions, the system continues with infusion 2907 as normal. If there is an occlusion detected, the system indicates an occlusion 2906. The system may set off an alarm to indicate the occlusion to the user.

In further embodiments, a series of measurements of a pump value may be used to determine whether the system has an occlusion. By using a series of measurements of a pump value that are close together to each other, it is possible to decrease the number of false identifications of occlusions, as well as to assure that occlusions are promptly identified. The series of measurements may be taken after a delivery of infusion fluid and prior to the next delivery of infusion fluid. For example, with monitoring force, multiple things can contribute to errors in determining the pressure in the reservoir by monitoring force behind the plunger, such as: (1) friction between the plunger and the reservoir wall, (2) friction between the slide and its seal, (3) misalignment of the drive system relative to the axis of the syringe, and (4) inaccuracies of the force sensor. All of these disturbances/errors contribute to inaccuracies in determining the pressure in the reservoir.

As frictions in the system, or misalignment, cause "noise" or errors in monitoring pressure, they can also be identified by other means to compensate for the errors and correcting inaccuracies of measurements. One indicator of errors is the current of the motor. The current of the motor during delivery, seating or priming can be an indicator of error, or elevated frictions. As the current increases or varies more during readings or from reading to reading it can indicate the inaccuracies of monitoring pressure in the syringe. Another indication of errors is the time of powering the motor during delivery. As friction(s) and/or misalignment increases or the variation increases, then the time to power the motor to accomplish the same rotation will increase or vary more from delivery to delivery. Yet another indication of errors is drive count or coast count. As friction(s) and/or misalignment increases, the drive count will increase and the coast count will decrease as the delivery algorithm compensates for the changes in force. As the variation in force or misalignment increases, the drive count and coast count will vary more as well. When the force increases, it may or may not be from increased pressure. The drive count will increase as the pressure increases. For this reason, the lower the force reading, the higher the drive count would need to be to assure there is an occlusion. If the drive count is high and the force reading is high, there is even more confidence of an occlusion. If the force reading is high and the drive count is low, there is less confidence of an occlusion. Yet another indication of errors is variation compensation of force readings. The friction or electrical operations can cause noise in force readings. By monitoring multiple force readings and determining the variation, a comparison value can be changed with respect to this. As the variation increases, the compensation value may increase to compensate for the increased noise. For example, as the standard deviation of sample force readings increases, the comparison value is increased. By monitoring the magnitude or variation of one or more of these variables, a compensated value to compare force readings may be created to determine more accurately if an occlusion has occurred.

Although the above variables assist in compensating for errors in monitoring the pressure, they cannot eliminate all of the noise in the readings. For this reason, filtering and/or weighing readings may improve accuracy of occlusion detection. In embodiments of the invention, data is filtered by removing the high and low data points. Multiple readings can be taken, for example prior to a delivery, continuing from past deliveries, or between deliveries. These readings may be stored in memory in the pump. The highest and lowest readings in the data set may then removed (a minimum of three readings are required for this). For example, if the data set is 3.4, 3.5, 3.2, 5.9, and 3.6, then 3.2 and 5.9 would be removed. Throwing out the highest and lowest data will produce an average value of 3.5, while not filtering would produce an average of 3.92. Other examples of filtering include using large data sets or using a moving average.

To weigh data sets, the weighting of the data set may be done as multiple readings are taken, either consecutively between deliveries, or historically for past deliveries, weighing the most recent reading more than previous readings because there is more confidence in the most recent reading. For example, if the data set is 1.2, 1.4, 1.3, 1.5, 1.5, and 1.7, the data points may each be multiplied by values to weigh the most recent reading highest and the least recent reading the lowest. For example, the weighed data may be 0.7*1.2, 0.8*1.4, 0.9*1.3, 1.1*1.5, 1.2*1.5, and 1.3*1.7. Then a weighted average may be created by summing up the weighted data and dividing by the number of samples in the data set.

Figure 32:
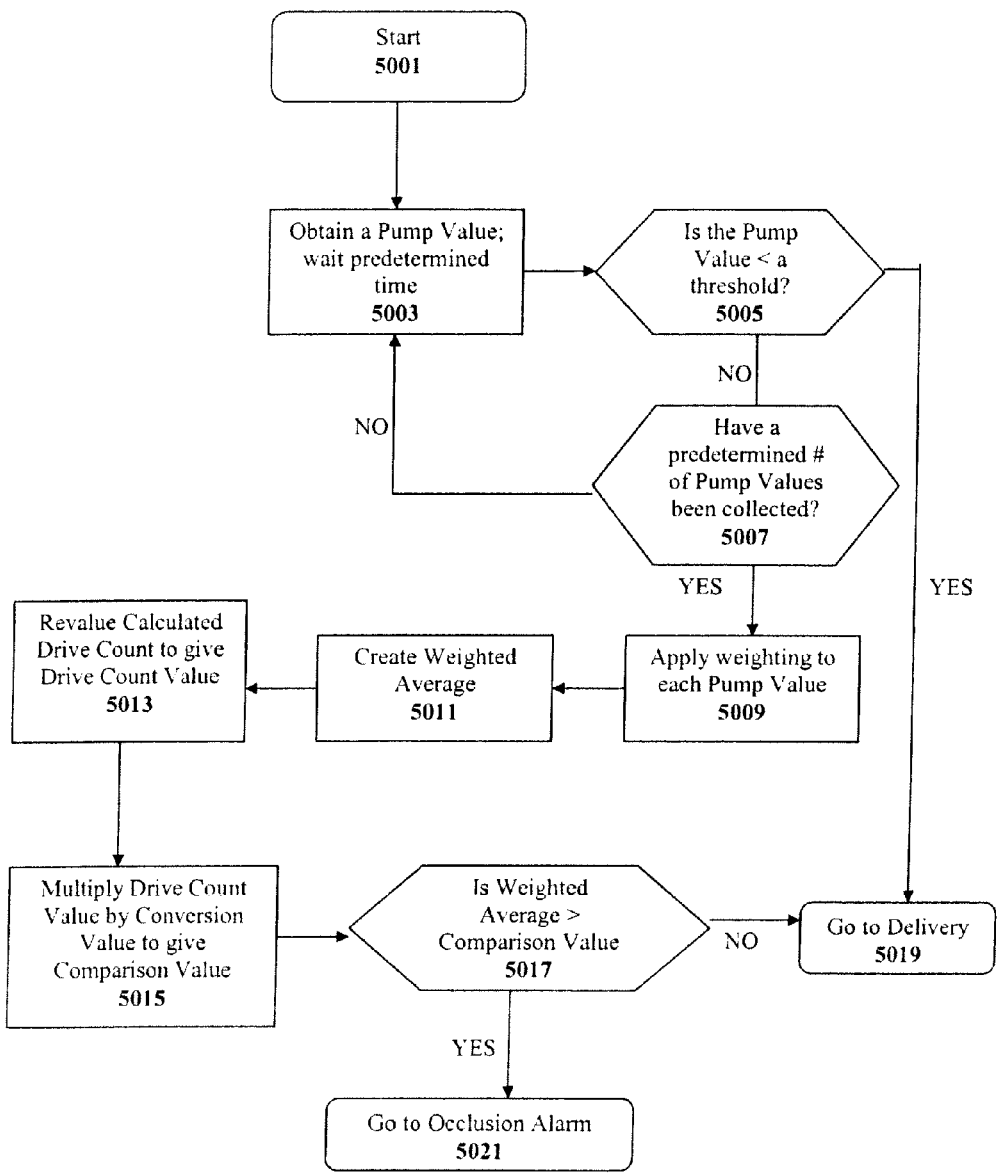
FIG. 32 illustrates an algorithm for detecting an occlusion in accordance with an embodiment of the present invention.

FIG. 32 illustrates a flow chart of the logic of embodiments using a series of measurements. In the embodiment shown in FIG. 32, the logic starts at 5001. The system measures a pump value at 5003. The pump value may be a parameter associated with the motor or one of the drive train components, such as pressure, delivery volume, force, drive current, drive voltage, motor drive time, motor coast time, delivery pulse energy, motor drive count, motor coast count, and delta encoder count. The pump value is preferably a force reading. The system then waits a predetermined amount of time, for example 10 milliseconds.

At 5005, the system determines whether the pump value is less than a predetermined maximum threshold. If the pump value is less than the predetermined maximum threshold, the system goes to delivery of an infusion cycle as normal at 5019. If the pump value is not less than the predetermined maximum threshold, the system determines whether a predetermined number of pump values has been collected, for example, five pump values at 5007. If not, the system returns to 5003 to obtain another pump value. The pump values collected are stored in memory. If the predetermined number of pump values has been collected at 5007, the system proceeds to apply a weighting to each pump value at 5009. For example, the weighting may be based on how recent the pump value was taken. The weighting may increase based on how recent the pump value was taken. Thus, a weighting factor may be assigned to each pump value, and the weighting factor may be larger for pump values taken more recently and smaller for pump values taken earlier in time. An example weighting for five pump values would be to multiply the first (oldest) reading by 0.9375, the second reading by 0.96875, the third reading by 1.0, the fourth reading by 1.03125, and the fifth (most recent) reading by 1.0625. Different weighting factors may be used as desired. It would be possible to use the same weighting factor for more than one pump value.

After the weighting has been performed at 5009, a weighted average is calculated at 5011. This may be calculated by adding the weighted pump values and dividing by the total number of weighted pump values. In further embodiments, the high and low weighted values may be removed before calculating the weighted average in lieu of or in addition to any previous removal of the high and low unweighted values. Next, the system may revalue the calculated drive count to give a drive count value at 5013. Other variables could be used. The drive count value may depend on the magnitude of the calculated drive count. The drive count values may be selected from at least two values, wherein each of the at least two values is defined to include a range of drive counts calculated. For example, in one embodiment, the drive count value is 1.1 if the calculated drive count is less than or equal to 20, the drive count value is 1.0 if the calculated drive count is greater than 20 but less than 60, and the drive count value is 0.9 if the calculated drive count is greater than or equal to 60. In further embodiments, each drive count may have its own, unique, drive count value. Next, the system multiplies the drive count value by a conversion value to obtain a comparison value (or threshold value) at 5015. The conversion value may be, for example, 2.667. At 5017, the system determines whether the weighted average is greater than the comparison value. If the weighted average is not greater than the comparison value, the system goes to a normal delivery at 5019. If the weighted average is greater than the comparison value, the system indicates that there is an occlusion by going to an occlusion alarm at 5021.

In particular, the above algorithms may compensate for increases in friction or misalignment with the comparison value. The noise is corrected by using the weighted average. A higher force is required to determine an occlusion at lower drive counts, and a lower force is required to determine occlusions at higher drive counts. By using a multivariable calculation like this, the chance of detecting false occlusions is decreased. In further embodiments, after an occlusion is declared, and, where necessary, the user instructs the pump to resume, the comparison value is set to 90% of the comparison value for a predetermined number of earlier deliveries, for example, the previous three deliveries. This eliminates lag in the system due to the system response and ensures immediate acknowledgement of the occlusion again if it has not been cleared.

As shown in FIG. 32, in particular embodiments, if a single pump value (e.g., force reading) is less than a predetermined maximum threshold at 5005, the system goes to delivery at 5019. In further embodiments, to minimize battery usage and computations between deliveries, the predetermined maximum threshold is 20% less than the conversion value. For example, if the conversion value is 2.667, the system will step out of the sampling routine and go directly to the delivery without sampling additional force readings if a single force reading is less than 2.134 (i.e., 0.8×2.667=2.1336).

While the description above refers to particular embodiments of the present inventions, it will be understood that many modifications may be made without departing from the spirit thereof. The accompanying claims are intended to cover such modifications as would fall within the true scope and spirit of the present inventions. When used in the claims, the phrase "selected from the group consisting of" followed by a list, such as "X, Y and Z," is not intended to mean that all members of the list must be present or that at least one of each of the members of the list must be present. It is intended to cover cases where one, some or all of the members of the list are present. For example, where the list is "X, Y, and Z," the claim would cover an embodiment containing just X, just Y, just Z, X and Y, X and Z, Y and Z, and X, Y, and Z. The presently disclosed embodiments are to be considered in all respects as illustrative and not restrictive, the scope of the inventions being indicated by the appended claims rather than the foregoing description, and all changes which come within the meaning and range of equivalency of the claims are therefore intended to be embraced therein.

Multiple methods have been described to enable the pump to monitor one or more parameters inherent to the system design that can be used individually or in combination to detect reduction in insulin delivery. One of these methods or multiple of these methods could be implemented into the pump software for redundancy providing multiple methods to monitor the system for potential occlusions. Additionally, one or multiple of these methods could be enabled by the user via software selection through the programmable pump user interface.

Each defined occlusion measurement method may have different effectiveness in monitoring the systems for true occlusions resulting in reduced insulin delivery without generating false alarms. In this case, more aggressive measurement techniques that may produce more false alarms due to higher sensitivity to variables could be disabled by the user through the software programmable interface. This would allow the user to adjust the system sensitivity to occlusions by the method selected. As an example, two methods may be implemented into the pump software as user selectable. The first could be the slope method with defined parameters such that it would detect occlusions with less missed insulin delivery than the second method, which would be a simple force threshold with a force value resulting in more missed delivery than the first method prior to indication of an occlusion alarm. The methods could be listed by different descriptions such as "high sensitivity" and "low sensitivity." The user could select "high sensitivity" and enable both methods or "low sensitivity" and enable only one method, for example the simple threshold method. Further, the system could implement two or more differing methods providing the user more than two selections. Further, the same measurement method could be implemented with two or more parameters that affect sensitivity to detect occlusion, whereby the selected parameter with the higher sensitivity is more likely to generate a false alarm but with the advantage of being able to detect true occlusion more rapidly. For example, the system could have a simple force threshold method for detecting occlusions, such as described in U.S. Pat. No. 6,362,591, which is herein incorporated by reference. The pump could have pre-programmed threshold trigger force values of, for example, 1.0 lbf, 2.0 lbf, and 3.0 lbf, and the user could select any of these force values. The lower the selected force value, the more sensitive the pump would be to increasing pressures due to occlusions thereby generating an occlusion alarm in less time at a given delivery rate. This higher sensitivity setting could result in a higher rate of false alarms. Alternatively, if the user were to select 3.0 lbf, the pump would be less likely to generate a false alarm at the cost of an increased time to generate an occlusion alarm for a true occlusion at a given delivery rate. Alternatively, instead of the user being given a selection of 1.0 lbf, 2.0 lbf, and 3.0 lbf, the user could be given the choice of "Low," "Med," and "High" sensitivities. Although three different selectable force values were discussed in this example, the system could be programmed with any number of selectable force values, for example, two, four or five. Additionally, this example described the simple force threshold method. Any of the discussed occlusion sensing methods described in this application could be implemented in a similar manner.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion pump for infusing fluid from a reservoir into a body of a user, the infusion pump comprising:
   a housing;
   a drive mechanism including a motor and one or more drive components contained within the housing and operatively coupled to the reservoir to deliver fluid from the reservoir through a fluid path into the body of the user;
   one or more electronic components to take a series of measurements of a parameter associated with the motor or one of the drive train components; and
   a controller contained within the housing, wherein the controller filters the series of measurements to remove the highest measurement and the lowest measurement, calculates a weighted average of the remaining measurements in the series of measurements, compares the weighted average to a maximum threshold value, and determines whether an occlusion has occurred in the fluid path of the infusion pump by determining whether the weighted average is greater than the maximum threshold value.

2. The infusion pump of claim 1, wherein each measurement after the first measurement in the series of measurements is taken a predetermined time after the previous measurement.

3. The infusion pump of claim 1, further including an alarm configured to activate if a determination is made that the weighted average is greater than the maximum threshold value.

4. The infusion pump of claim 1, wherein the parameter associated with the motor is independently selected from the group consisting of pressure, delivery volume, force, drive current, drive voltage, motor drive time, motor coast time, delivery pulse energy, motor drive count, motor coast count, and delta encoder count.

5. The infusion pump of claim 1, wherein the parameter is force.

6. The infusion pump of claim 1, wherein the electronic components include a sensor to measure force.

7. The infusion pump of claim 1, wherein the electronic components include an encoder to measure motor drive count.

8. The infusion pump of claim 1, wherein the controller determines the drive count of the motor, determines a drive count value based on the drive count of the motor, and calculates the maximum threshold value based on the drive count value.

9. The infusion pump of claim 8, wherein the drive count value is X when the drive count of the motor is within a first range of drive counts, wherein the drive count value is Y when the drive count of the motor is within a second range of drive counts, wherein the drive counts within the first range are less than the drive counts within the second range, and wherein Y is less than X.

10. The infusion pump of claim 8, wherein the controller calculates the maximum threshold value by multiplying the drive count value by a predetermined conversion value.

11. The infusion pump of claim 10, wherein the predetermined conversion value is calculated from a formula including at least one factor selected from the group consisting of current, time of powering the motor, drive count, coast count, and standard deviation of force readings.

12. The infusion pump of claim 1, wherein after each measurement in the series of measurements is taken, the controller compares the measurement to a predetermined lower threshold value before the next measurement in the series of measurements is taken, and wherein if the comparison indicates that the measurement taken is less than the predetermined lower threshold value, the controller determines that there is no occlusion.

13. The infusion pump of claim 12, wherein the predetermined lower threshold value is equal to N multiplied by a predetermined conversion value, wherein N is less than 1.0.

14. The infusion pump of claim 1, wherein the one or more electronic components take said series of measurements prior to delivery of infusion fluid.

15. The infusion pump of claim 1, wherein the one or more electronic components take said series of measurements during delivery of infusion fluid.

16. The infusion pump of claim 1, wherein the one or more electronic components take said series of measurements after delivery of infusion fluid.

17. The infusion pump of claim 1, wherein the series of measurements includes at least three measurements.

18. The infusion pump of claim 1, wherein the series of measurements includes at least five measurements, and the controller filters the series of measurements to remove at least one additional measurement before calculating the weighted average.

19. The infusion pump of claim 1, wherein the controller calculates said weighted average by applying a weighting factor to each remaining measurement in the series of measurements to determine a weighted value corresponding to each said remaining measurement and calculating the average of the weighted values.

* * * * *